US009193937B2

(12) United States Patent
Scheibel et al.

(10) Patent No.: US 9,193,937 B2
(45) Date of Patent: Nov. 24, 2015

(54) MIXTURES OF C10-C13 ALKYLPHENYL SULFONATES

(75) Inventors: Jeffrey John Scheibel, Glendale, OH (US); Phillip Richard Green, Wyoming, OH (US); Jiten Odhavji Dihora, Hamilton, OH (US); Phillip Kyle Vinson, Fairfield, OH (US); Stephanie Ann Urbin, Liberty, OH (US); Dimitris Ioannis Collias, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 29 days.

(21) Appl. No.: 13/399,338

(22) Filed: Feb. 17, 2012

(65) Prior Publication Data
US 2012/0214724 A1 Aug. 23, 2012

Related U.S. Application Data

(60) Provisional application No. 61/444,007, filed on Feb. 17, 2011.

(51) Int. Cl.
| | |
|---|---|
| *C11D 1/22* | (2006.01) |
| *A61K 8/31* | (2006.01) |
| *A61K 8/46* | (2006.01) |
| *A61Q 5/02* | (2006.01) |
| *A61Q 19/10* | (2006.01) |
| *C11D 7/24* | (2006.01) |

(52) U.S. Cl.
CPC ... *C11D 1/22* (2013.01); *A61K 8/31* (2013.01); *A61K 8/466* (2013.01); *A61Q 5/02* (2013.01); *A61Q 19/10* (2013.01); *C11D 7/247* (2013.01)

(58) Field of Classification Search
None
See application file for complete search history.

(56) References Cited

U.S. PATENT DOCUMENTS

| 2,396,278 A | 3/1946 | Lind |
| 2,438,091 A | 3/1948 | Lynch |
| 2,486,921 A | 11/1949 | Byerly |

(Continued)

FOREIGN PATENT DOCUMENTS

| BR | 9502668-1 A | 3/1996 |
| CN | 1032157 A | 4/1989 |

(Continued)

OTHER PUBLICATIONS

Hons, G., "Alkylarylsulfonates: History, Manufacture, Analysis and Environmental Properties," in Anionic Surfactants: Organic Chemistry, Stache, H. W., Ed: Surfactants, Surfactant Science Series, Marcel Dekker, Ch. 2, pp. 39-108 (1996).

(Continued)

*Primary Examiner* — Necholus Ogden, Jr.
(74) *Attorney, Agent, or Firm* — Melissa Krasovec

(57) ABSTRACT

The invention is directed to mixtures comprising $C_{10}$-$C_{13}$ alkylphenyl sulfonates having alkyl groups in a particular distribution (e.g., bimodal, peaked, and skewed). These $C_{10}$-$C_{13}$ alkylphenyl sulfonates are optionally renewable and unexpectedly provide superior results when used in consumer product cleaning and personal care compositions (e.g., dishcare, laundry, hard surface cleaners, shampoos, conditioners, and soaps). The invention is further directed to a method of making a mixture of partially or wholly renewable $C_{10}$-$C_{13}$ alkylphenyl sulfonates having a particular alkyl group distribution.

7 Claims, 13 Drawing Sheets

(56) References Cited

U.S. PATENT DOCUMENTS

| | | |
|---|---|---|
| 2,486,922 A | 11/1949 | Strain |
| 2,528,378 A | 10/1950 | Mannheimer et al. |
| 2,658,072 A | 11/1953 | Kosmin |
| 3,308,067 A | 3/1967 | Diehl |
| 3,332,880 A | 7/1967 | Kessler et al. |
| 3,427,342 A | 2/1969 | Brooks et al. |
| 3,487,023 A | 12/1969 | Sweeney |
| 3,519,570 A | 7/1970 | McCarty |
| 3,553,139 A | 1/1971 | McCarty |
| 3,600,319 A | 8/1971 | Gedge, III et al. |
| 3,646,015 A | 2/1972 | Hamilton |
| 3,664,961 A | 5/1972 | Norris |
| 3,885,155 A | 5/1975 | Anbar |
| 3,893,929 A | 7/1975 | Basadur |
| 3,929,678 A | 12/1975 | Laughlin et al. |
| 3,944,470 A | 3/1976 | Diehl et al. |
| 3,959,230 A | 5/1976 | Hays |
| 4,000,093 A | 12/1976 | Nicol et al. |
| 4,033,718 A | 7/1977 | Holcombe et al. |
| 4,062,647 A | 12/1977 | Storm et al. |
| 4,101,457 A | 7/1978 | Place et al. |
| 4,111,855 A | 9/1978 | Barrat et al. |
| 4,133,779 A | 1/1979 | Hellyer et al. |
| 4,140,641 A | 2/1979 | Ramachandran |
| 4,201,824 A | 5/1980 | Violland et al. |
| 4,240,918 A | 12/1980 | Lagasse et al. |
| 4,261,868 A | 4/1981 | Hora et al. |
| 4,287,082 A | 9/1981 | Tolfo et al. |
| 4,291,071 A | 9/1981 | Harris et al. |
| 4,305,837 A | 12/1981 | Kaminsky et al. |
| 4,316,824 A | 2/1982 | Pancheri |
| 4,375,416 A | 3/1983 | Crisp et al. |
| 4,404,115 A | 9/1983 | Tai |
| 4,412,934 A | 11/1983 | Chung et al. |
| 4,420,644 A | 12/1983 | Huibers et al. |
| 4,427,884 A | 1/1984 | Anbar et al. |
| 4,430,243 A | 2/1984 | Bragg |
| 4,452,717 A | 6/1984 | Tai et al. |
| 4,462,922 A | 7/1984 | Boskamp |
| 4,470,919 A | 9/1984 | Goffinet et al. |
| 4,483,781 A | 11/1984 | Hartman |
| 4,507,219 A | 3/1985 | Hughes |
| 4,520,214 A | 5/1985 | Vora |
| 4,523,048 A | 6/1985 | Vora |
| 4,525,524 A | 6/1985 | Tung et al. |
| 4,526,709 A | 7/1985 | Boskamp et al. |
| 4,529,525 A | 7/1985 | Dormal et al. |
| 4,530,780 A | 7/1985 | van de Pas et al. |
| 4,537,706 A | 8/1985 | Severson, Jr. |
| 4,537,707 A | 8/1985 | Severson, Jr. |
| 4,537,709 A | 8/1985 | Edge et al. |
| 4,545,941 A | 10/1985 | Rosenburg |
| 4,579,681 A | 4/1986 | Ruppert et al. |
| 4,597,898 A | 7/1986 | Vander Meer |
| 4,618,446 A | 10/1986 | Haslop et al. |
| 4,634,551 A | 1/1987 | Burns et al. |
| 4,639,321 A | 1/1987 | Barrat et al. |
| 4,647,393 A | 3/1987 | Ouhadi et al. |
| 4,648,983 A | 3/1987 | Broze et al. |
| 4,655,954 A | 4/1987 | Broze et al. |
| 4,659,497 A | 4/1987 | Akred et al. |
| 4,661,280 A | 4/1987 | Ouhadi et al. |
| 4,670,179 A | 6/1987 | Inamorato et al. |
| 4,681,704 A | 7/1987 | Bernardino et al. |
| 4,686,062 A | 8/1987 | Kermode et al. |
| 4,690,771 A | 9/1987 | Ouhadi et al. |
| 4,695,560 A | 9/1987 | Gattuso et al. |
| 4,702,857 A | 10/1987 | Gosselink |
| 4,711,730 A | 12/1987 | Gosselink et al. |
| 4,721,580 A | 1/1988 | Gosselink |
| 4,728,455 A | 3/1988 | Rerek |
| 4,732,707 A | 3/1988 | Naik et al. |
| 4,744,916 A | 5/1988 | Adams et al. |
| 4,746,456 A | 5/1988 | Kud et al. |
| 4,751,008 A | 6/1988 | Crossin |
| 4,753,750 A | 6/1988 | Ouhadi et al. |
| 4,761,509 A | 8/1988 | Vora et al. |
| 4,787,989 A | 11/1988 | Fanelli et al. |
| 4,790,856 A | 12/1988 | Wixon |
| 4,793,943 A | 12/1988 | Haslop et al. |
| 4,795,623 A | 1/1989 | Evans |
| 4,842,758 A | 6/1989 | Crutzen |
| 4,844,821 A | 7/1989 | Mermelstein et al. |
| 4,844,824 A | 7/1989 | Mermelstein et al. |
| 4,871,467 A | 10/1989 | Akred et al. |
| 4,873,001 A | 10/1989 | Ramachandran et al. |
| 4,877,896 A | 10/1989 | Maldonado et al. |
| 4,891,147 A | 1/1990 | Gray et al. |
| 4,891,160 A | 1/1990 | Vander Meer |
| 4,900,475 A | 2/1990 | Ramachandran et al. |
| 4,908,150 A | 3/1990 | Hessel et al. |
| 4,911,852 A | 3/1990 | Coffindaffer et al. |
| 4,915,854 A | 4/1990 | Mao et al. |
| 4,923,635 A | 5/1990 | Simion et al. |
| 4,924,027 A | 5/1990 | Kulprathipanja et al. |
| 4,925,588 A | 5/1990 | Berrod et al. |
| 4,943,397 A | 7/1990 | Johnson |
| 4,950,424 A | 8/1990 | van der Hoeven et al. |
| 4,966,723 A | 10/1990 | Hodge et al. |
| 4,968,451 A | 11/1990 | Scheibel et al. |
| 4,973,841 A | 11/1990 | Purser |
| 5,004,556 A | 4/1991 | Julemont et al. |
| 5,006,273 A | 4/1991 | Machin et al. |
| 5,017,296 A | 5/1991 | Nedonchelle |
| 5,021,195 A | 6/1991 | Machin et al. |
| 5,057,240 A | 10/1991 | Madore et al. |
| 5,082,585 A | 1/1992 | Hessel et al. |
| 5,082,956 A | 1/1992 | Monnier et al. |
| 5,102,574 A | 4/1992 | Russell et al. |
| 5,104,646 A | 4/1992 | Bolich, Jr. et al. |
| 5,106,609 A | 4/1992 | Bolich, Jr. et al. |
| 5,114,606 A | 5/1992 | van Vliet et al. |
| 5,114,611 A | 5/1992 | Van Kralingen et al. |
| 5,147,576 A | 9/1992 | Montague et al. |
| 5,153,161 A | 10/1992 | Kerschner et al. |
| 5,156,773 A | 10/1992 | Kochavi et al. |
| 5,160,655 A | 11/1992 | Donker et al. |
| 5,194,416 A | 3/1993 | Jureller et al. |
| 5,196,574 A | 3/1993 | Kocal |
| 5,207,941 A | 5/1993 | Kroner et al. |
| 5,227,084 A | 7/1993 | Martens et al. |
| 5,230,823 A | 7/1993 | Wise et al. |
| 5,244,594 A | 9/1993 | Favre et al. |
| 5,245,094 A | 9/1993 | Kocal |
| 5,246,566 A | 9/1993 | Miller |
| 5,246,612 A | 9/1993 | Van Dijk et al. |
| 5,246,621 A | 9/1993 | Favre et al. |
| 5,250,212 A | 10/1993 | de Buzzaccarini et al. |
| 5,256,779 A | 10/1993 | Kerschner et al. |
| 5,264,143 A | 11/1993 | Boutique |
| 5,269,960 A | 12/1993 | Gray et al. |
| 5,269,974 A | 12/1993 | Ofosu-Asante |
| 5,274,147 A | 12/1993 | Kerschner et al. |
| 5,275,753 A | 1/1994 | de Buzzaccarini et al. |
| 5,280,117 A | 1/1994 | Kerschner et al. |
| 5,284,944 A | 2/1994 | Madison et al. |
| 5,288,746 A | 2/1994 | Pramod |
| 5,298,421 A | 3/1994 | Davies et al. |
| 5,304,481 A | 4/1994 | Davies et al. |
| 5,314,635 A | 5/1994 | Hage et al. |
| 5,334,793 A | 8/1994 | Kocal |
| 5,344,771 A | 9/1994 | Davies et al. |
| 5,344,997 A | 9/1994 | Kocal |
| 5,356,554 A | 10/1994 | Delwel et al. |
| 5,376,310 A | 12/1994 | Cripe et al. |
| 5,409,632 A | 4/1995 | Showell et al. |
| 5,415,807 A | 5/1995 | Gosselink et al. |
| 5,422,030 A | 6/1995 | Panandiker et al. |
| 5,431,842 A | 7/1995 | Panandiker et al. |
| 5,431,848 A | 7/1995 | Getty |
| 5,438,194 A | 8/1995 | Koudijs et al. |
| 5,442,100 A | 8/1995 | Bjorkquist et al. |
| 5,445,756 A | 8/1995 | Didier et al. |
| 5,468,414 A | 11/1995 | Panandiker et al. |

(56) References Cited

U.S. PATENT DOCUMENTS

| | | |
|---|---|---|
| 5,489,392 A | 2/1996 | Capeci et al. |
| 5,496,487 A | 3/1996 | Capeci et al. |
| 5,500,137 A | 3/1996 | Bacon et al. |
| 5,500,138 A | 3/1996 | Bacon et al. |
| 5,500,153 A | 3/1996 | Figueroa et al. |
| 5,500,154 A | 3/1996 | Bacon et al. |
| 5,505,866 A | 4/1996 | Bacon et al. |
| 5,510,042 A | 4/1996 | Hartman et al. |
| 5,510,306 A | 4/1996 | Murray |
| 5,512,482 A | 4/1996 | Voelker et al. |
| 5,516,448 A | 5/1996 | Capeci et al. |
| 5,531,910 A | 7/1996 | Severns et al. |
| 5,540,852 A | 7/1996 | Kefauver et al. |
| 5,540,853 A | 7/1996 | Bacon et al. |
| 5,543,083 A | 8/1996 | Sivik et al. |
| 5,547,476 A | 8/1996 | Siklosi et al. |
| 5,554,587 A | 9/1996 | Capeci |
| 5,559,088 A | 9/1996 | Severns et al. |
| 5,562,847 A | 10/1996 | Waite et al. |
| 5,565,145 A | 10/1996 | Watson et al. |
| 5,565,422 A | 10/1996 | Del Greco et al. |
| 5,569,645 A | 10/1996 | Dinniwell et al. |
| 5,573,697 A | 11/1996 | Riddick et al. |
| 5,574,005 A | 11/1996 | Welch et al. |
| 5,576,282 A | 11/1996 | Miracle et al. |
| 5,576,285 A | 11/1996 | France et al. |
| 5,578,234 A | 11/1996 | Corona, III et al. |
| 5,580,485 A | 12/1996 | Feringa et al. |
| 5,580,486 A | 12/1996 | Labeque et al. |
| 5,591,236 A | 1/1997 | Roetker |
| 5,595,967 A | 1/1997 | Miracle et al. |
| 5,597,936 A | 1/1997 | Perkins et al. |
| 5,630,847 A | 5/1997 | Roetker |
| 5,630,848 A | 5/1997 | Young et al. |
| 5,632,780 A | 5/1997 | Siklosi |
| 5,641,739 A | 6/1997 | Kott et al. |
| 5,661,299 A | 8/1997 | Purser |
| 5,665,692 A | 9/1997 | Kaminsky |
| 5,696,068 A | 12/1997 | Outtrup et al. |
| 5,703,025 A | 12/1997 | Wiegand et al. |
| 5,705,474 A | 1/1998 | Severns et al. |
| 5,707,959 A | 1/1998 | Pancheri et al. |
| 5,723,435 A | 3/1998 | Sivik et al. |
| 5,767,052 A | 6/1998 | Shaw et al. |
| 5,850,022 A | 12/1998 | Dehesh et al. |
| 5,872,092 A | 2/1999 | Kong-Chan et al. |
| 5,932,202 A | 8/1999 | Guskey et al. |
| 5,942,653 A | 8/1999 | Du Plessis et al. |
| 5,952,289 A | 9/1999 | Wise et al. |
| 6,004,915 A | 12/1999 | Elliott et al. |
| 6,020,303 A | 2/2000 | Cripe et al. |
| 6,060,443 A | 5/2000 | Cripe et al. |
| 6,074,996 A | 6/2000 | Elliott et al. |
| 6,133,212 A | 10/2000 | Elliott et al. |
| 6,221,430 B1 | 4/2001 | Tompsett |
| 6,274,540 B1 | 8/2001 | Scheibel et al. |
| 6,306,817 B1 | 10/2001 | Kott et al. |
| 6,335,312 B1 | 1/2002 | Coffindaffer et al. |
| 6,514,926 B1 | 2/2003 | Kott et al. |
| 6,566,319 B1 | 5/2003 | Scheibel et al. |
| 6,583,096 B1 | 6/2003 | Kott et al. |
| 6,586,649 B1 | 7/2003 | Both et al. |
| 6,593,285 B1 | 7/2003 | Scheibel et al. |
| 6,602,840 B1 | 8/2003 | Scheibel et al. |
| 6,627,778 B2 | 9/2003 | Xu et al. |
| 6,777,582 B2 | 8/2004 | Gartside et al. |
| 6,831,184 B2 | 12/2004 | Zhang et al. |
| 6,855,680 B2 | 2/2005 | Smerznak et al. |
| 7,462,205 B2 | 12/2008 | Murphy |
| 7,501,389 B2 | 3/2009 | Hage et al. |
| 7,635,794 B2 | 12/2009 | Basset et al. |
| 7,637,968 B2 | 12/2009 | Murphy |
| 7,671,224 B2 | 3/2010 | Winde et al. |
| 7,683,224 B2 | 3/2010 | Connor |
| 7,851,438 B2 | 12/2010 | Sethurman et al. |
| 7,977,084 B2 | 7/2011 | Sun et al. |
| 8,067,623 B2 | 11/2011 | Lee |
| 8,097,439 B2 | 1/2012 | Alibhai et al. |
| 8,110,093 B2 | 2/2012 | Friedman et al. |
| 8,183,028 B2 | 5/2012 | Alibhai et al. |
| 8,268,599 B2 | 9/2012 | Schirmer et al. |
| 8,313,934 B2 | 11/2012 | Bhatia et al. |
| 8,344,052 B2 | 1/2013 | Braksmayer et al. |
| 8,487,149 B2 | 7/2013 | Gruber et al. |
| 8,501,973 B2 | 8/2013 | Schrodi et al. |
| 8,535,916 B2 | 9/2013 | Del Cardayre et al. |
| 2002/0022040 A1 | 2/2002 | Robinson et al. |
| 2003/0135080 A1 | 7/2003 | Botha et al. |
| 2004/0030209 A1 | 2/2004 | Narbeshuber et al. |
| 2005/0272134 A1 | 12/2005 | Hughes |
| 2006/0079704 A1 | 4/2006 | Lacombe et al. |
| 2006/0211905 A1 | 9/2006 | Forman et al. |
| 2007/0002022 A1 | 1/2007 | Joung et al. |
| 2007/0219521 A1 | 9/2007 | Hird et al. |
| 2008/0033026 A1 | 2/2008 | Zullo et al. |
| 2008/0221345 A1 | 9/2008 | Winde et al. |
| 2008/0255328 A1 | 10/2008 | Basset et al. |
| 2008/0293060 A1 | 11/2008 | Schirmer et al. |
| 2009/0061493 A1 | 3/2009 | Trimbur et al. |
| 2009/0119977 A1 | 5/2009 | Murphy |
| 2009/0124839 A1 | 5/2009 | Dumesic et al. |
| 2009/0126602 A1 | 5/2009 | Murphy et al. |
| 2009/0217568 A1 | 9/2009 | Murphy et al. |
| 2009/0220443 A1 | 9/2009 | Braksmayer et al. |
| 2009/0232873 A1 | 9/2009 | Glenn, Jr. et al. |
| 2009/0259065 A1 | 10/2009 | Abraham et al. |
| 2009/0264672 A1 | 10/2009 | Abraham et al. |
| 2009/0275097 A1 | 11/2009 | Sun et al. |
| 2010/0024281 A1 | 2/2010 | Lemke et al. |
| 2010/0071259 A1 | 3/2010 | Hu et al. |
| 2010/0094034 A1 | 4/2010 | Kaido et al. |
| 2010/0105955 A1 | 4/2010 | Alibhai et al. |
| 2010/0105963 A1 | 4/2010 | Hu |
| 2010/0132250 A1 | 6/2010 | Uptain et al. |
| 2010/0137649 A1 | 6/2010 | Scheibel et al. |
| 2010/0145086 A1 | 6/2010 | Schrodi et al. |
| 2010/0154293 A1 | 6/2010 | Hom et al. |
| 2010/0160506 A1 | 6/2010 | Wu et al. |
| 2010/0170826 A1 | 7/2010 | Friedman et al. |
| 2010/0191008 A1 | 7/2010 | Olson |
| 2010/0199548 A1 | 8/2010 | del Cardayre et al. |
| 2010/0205851 A1 | 8/2010 | Uptain et al. |
| 2010/0221798 A1 | 9/2010 | Schirmer et al. |
| 2010/0235934 A1 | 9/2010 | Friedman et al. |
| 2011/0160472 A1 | 6/2011 | Lemke et al. |
| 2011/0230687 A1 | 9/2011 | Luetkens, Jr. et al. |
| 2011/0237850 A1 | 9/2011 | Luetkens, Jr. et al. |
| 2011/0313180 A1 | 12/2011 | Uptain et al. |
| 2012/0258900 A1* | 10/2012 | Adams et al. .............. 510/226 |
| 2013/0029395 A1 | 1/2013 | Schirmer et al. |

FOREIGN PATENT DOCUMENTS

| | | |
|---|---|---|
| DE | 2 335 044 A1 | 1/1974 |
| EP | 0 066 915 A2 | 12/1982 |
| EP | 0 054 436 | 6/1984 |
| EP | 0 111 965 A2 | 6/1984 |
| EP | 0 111 984 A2 | 6/1984 |
| EP | 0 112 592 A2 | 7/1984 |
| EP | 0 133 354 A1 | 2/1985 |
| EP | 0 199 405 A2 | 10/1986 |
| EP | 0 200 586 A1 | 11/1986 |
| EP | 0 225 654 A1 | 6/1987 |
| EP | 0 315 126 A2 | 5/1989 |
| EP | 0 544 490 A1 | 6/1993 |
| EP | 0 549 272 A1 | 6/1993 |
| EP | 0 564 250 A2 | 10/1993 |
| EP | 0 583 534 A1 | 2/1994 |
| EP | 0 583 535 A1 | 2/1994 |
| EP | 0 598 170 A1 | 5/1994 |
| EP | 0 598 973 A1 | 6/1994 |
| EP | 0 619 368 A1 | 10/1994 |
| EP | 0 633 311 A1 | 1/1995 |
| EP | 0 694 608 A1 | 1/1996 |

(56) References Cited

FOREIGN PATENT DOCUMENTS

| | | |
|---|---|---|
| EP | 0 705 900 A1 | 4/1996 |
| EP | 0 709 449 A1 | 5/1996 |
| EP | 0 738 778 A1 | 10/1996 |
| EP | 0 739 977 A1 | 10/1996 |
| EP | 0 743 279 A1 | 11/1996 |
| EP | 0 743 280 A1 | 11/1996 |
| EP | 0 751 210 A1 | 1/1997 |
| EP | 0 751 213 A1 | 1/1997 |
| EP | 0 752-466 A1 | 1/1997 |
| EP | 0 752 469 A1 | 1/1997 |
| EP | 0 753 556 A1 | 1/1997 |
| EP | 0 753 557 A1 | 1/1997 |
| EP | 0 753 558 A1 | 1/1997 |
| EP | 0 753 559 A1 | 1/1997 |
| EP | 0 753 560 A1 | 1/1997 |
| EP | 0 753 569 A1 | 1/1997 |
| EP | 0 753 571 A1 | 1/1997 |
| EP | 0 754 749 A1 | 1/1997 |
| GB | 0 514 612 A | 11/1939 |
| GB | 1068528 * | 5/1987 |
| GB | 2 292 155 A | 2/1996 |
| GB | 2 292 562 A | 2/1996 |
| GB | 2 297-761 A | 8/1996 |
| GB | 2 297 762 A | 8/1996 |
| GB | 2 297 975 A | 8/1996 |
| WO | WO 89/08694 A1 | 9/1989 |
| WO | WO 93/07260 A1 | 4/1993 |
| WO | WO 93/07263 A2 | 4/1993 |
| WO | WO 94/23009 A1 | 10/1994 |
| WO | WO 96/02490 A1 | 2/1996 |
| WO | WO 96/04360 A1 | 2/1996 |
| WO | WO 96/10072 A1 | 4/1996 |
| WO | WO 96/15308 A1 | 5/1996 |
| WO | WO 96/17916 A1 | 6/1996 |
| WO | WO 96/22352 A1 | 7/1996 |
| WO | WO 96/23048 A1 | 8/1996 |
| WO | WO 96/34082 A1 | 10/1996 |
| WO | WO 96/37589 A1 | 11/1996 |
| WO | WO 96/37595 A1 | 11/1996 |
| WO | WO 97/00930 A1 | 1/1997 |
| WO | WO 97/00936 A1 | 1/1997 |
| WO | WO 97/00937 A1 | 1/1997 |
| WO | WO 97/00938 A1 | 1/1997 |
| WO | WO9905084 * | 2/1999 |
| WO | WO 01/02324 A1 | 1/2001 |
| WO | WO 2007/136762 A1 | 11/2007 |
| WO | WO 2007/136873 A2 | 11/2007 |
| WO | WO 2008/119082 A2 | 10/2008 |
| WO | WO 2008/140469 A2 | 11/2008 |
| WO | WO 2009/155086 A2 | 12/2009 |
| WO | WO 2010/034736 A1 | 4/2010 |

OTHER PUBLICATIONS

Alul et al., "Solvent Effects in the Alkylation of Benzene with 1-Dodecene and Trans-6-Dodecene in the Presence of Hydrogen Fluoride," *J. Org. Chem.*, 32(11):3365-3369 (1967).
Alvarez et al., "Triacylglycerols in Prokaryotic Microorganisms," *Appl. Microbiol. Biotechnol.*, 60:367-376 (2002).
Atsumi et al., "Non-Fermentative Pathways for Synthesis of Branched-Chain Higher Alcohols as Biofuels," *Nature*, 451(7174):86-89 (2008).
Bond et al., "□-Valerolactone Ring-Opening and Decarboxylation Over SiO2/Al2O3 in the Presence of Water," *Langmuir*, 2(26):16291-16298 (2010).
Bond et al., "Integrated Catalytic Conversion of □-Valerolactone to Liquid Alkenes for Transportation Fuels," *Science*, 327(5969):1110-1114 (2010).
Buchmeiser, "Polymer-Supported Well-Defined Metathesis Catalysts," *Chem. Rev.*, 109:303-321 (2009).
Cargill, "Cargill's Activities to Develop Industrial Chemicals from Plants," Plant Bio-Industrial Oils Workshop (2006).
Chiang, "Biomass Waste to Olefins Technology," PowerPoint Presentation (2005).
De Mendoza et al., "Thermal Regulation of Membrane Fluidity in *Escherichia coli*. Effects of Overproduction of Beta-ketoacyl-acyl Carrier Protein Synthase I.," *J. Biol. Chem.*, 258(4):2098-2101 (1983).
Denoya et al., "A Second Branched-Chain Alpha-Keto Acid Dehydrogenase Gene Cluster (bkdFGH) from Streptomyces Avermitilis: Its Relationship to Avermectin Biosynthesis and the Contruction of a bkdF Mutant Suitable for the Production of Novel Antiparasitic Avermectins," *J. Bacteriol.*, 177(12):3504-3511 (1995).
Diver, "Metal Carbenes in Enyne Metathesis: Synthetic and Mechanistic Studies," *Journal of Molecular Catalysis A: Chemical*, 254:29-42 (2006).
Dunning, "Review of Olefin Isomerization," *Ind. Eng. Chem.*, 45(3):551-564 (1953).
Dwyer, "Metathesis: An Industrial Perspective," ISOM XVII, Pasadena, CA, (2007).
Ewell et al., "Isomerization Equilibrium Among the Branched Chain Pentenes," *J. Am. Chem. Soc.*, 63:3460-3465 (1941).
Han et al., "A Novel Alternate Anaplerotic Pathway to the Glyoxylate Cycle in Streptomycetes," *J. Bacteriol*, 179(16):5157-5164 (1997).
Heath et al., "Lipid Biosynthesis as a Target for Antibacterial Agents," *Prog. Lipid Res.*, 40(6):467-497 (2001).
Hranueli et al., "Molecular Biology of Polyketide Biosynthesis," *Food Technol. Biotechnol.*, 39(3):203-213 (2001).
Huber et al., "Production of Liquid Alkanes by Aqueous-Phase Processing of Biomass-Derived Carbohydrates," *Science*, 308(5727):1446-1450 (2005).
Huber et al., "Renewable Alkanes by Aqueous-Phase Reforming of Biomass-Derived Oxygenates," *Angewandte Chemie, International Ed.*, 43(12):1549-1551 (2004).
Ingram et al., "Propionate-Induced Synthesis of Odd-Chain-Length Fatty Acids by *Escherichia coli*," *Journal of Bacteriology*, 131(3):1023-1025 (1977).
Kirk, "Ruthenium Based Homogeneous Olefin Metathesis," M.S. Dissertation, University of the Free State, South Africa, (2005).
Kunkes et al., "Catalytic Conversion of Biomass to Monofunctional Hydrocarbons and Targeted Liquid-Fuel Classes," *Science*, 322(5900):417-421 (2008).
Ladygina et al., "A Review on Microbial Synthesis of Hydrocarbons," *Process Biochemistry*, 41:1001-1014 (2006).
Lai, K.Y., et al in *Liquid Detergents*, Surfactant Science Series, vol. 67, Lai, K.Y. Ed., Marcel Dekker, New York, pp. 309-324 (1996).
Lennen et al., "A Process for Microbial Hydrocarbon Synthesis: Overproduction of Fatty Acids in *Escherichia coli* and Catalytic Conversion to Alkanes," *Biotechnology and Bioengineering*, 106(2):193-202 (2010).
Li et al., "Alteration of the Fatty Acid Profile of Streptomyces coelicolor by Replacement of the Initiation Enzyme 3-ketoacyl Acyl Carrier Protein Synthesis III (FabH)," *J. Bacteriol.*, 187(11):3795-3799 (2005).
Lomax, E. Amphoteric Surfactants, Surfactant Science Series, vol. 59, Second Edition, Ed., Marcel Dekker, Inc. New York (1996).
Magnuson et al., "Regulation of Fatty Acid Biosynthesis in *Escherichia coli*," *Microbiological Reviews*, 57(3):522-542 (1993).
Marrakchi et al., "A New Mechanism for Anaerobic Unsaturated Fatty Acid Formation in *Streptococcus pneumoniae*," *J. Biol. Chem.*, 277(47):44809-44816 (2002).
Marrakchi et al., "Mechanistic Diversity and Regulation of Type II Fatty Acid Synthesis," *Biochemical Society Trans.*, 30:1050-1055 (2002).
Marvy et al., "Ruthenium Carbene Mediated Meathesis of Oleate-Type Fatty Compounds," *Int. J. Mol. Sci.*, 9:615-625 (2008).
Marvy, "Sunflower-based Feedstocks in Nonfood Applications: Perspectives from Olefin Metathesis," *Int. J. Mol. Sci.*, 9:1393-1406 (2008).
Miller, "New Molecular Sieve Process for Lube Dewaxing by Wax Isomerization" *Microporous Materials*, 2(5):439-449 (1994).

(56) References Cited

OTHER PUBLICATIONS

Ngo et al., "Metathesis of Unsaturated Fatty Acids: Synthesis of Long-Chain Unsaturated-☐, ☐-Dicarboxylic Acids," *JAOCS*, 83(7):629-634 (2006).

Park et al., "Metabolic Engineering of *Escherichia coli* for the Production of L-Valine Based on Transcriptome Analysis and in Silico Gene Knockout Simulation," *Proc. Natl. Acad. Sci. USA*, 104(19):7797-7802 (2007).

Paushkin et al., "Plant Biomass as Raw Material for the Production of Olefins and Motor Fuels," *Chemistry and Technology of Fuels and Oils*, 30(5-6):249-252 (1994).

Pocklington, "Determination of the Iodine Value of Oils and Fats: Results of a Collaborative Study," *Pure & Appl. Chem.*, 62(12):2339-2343 (1990).

Rawlings, "Biosynthesis of Polyketides (Other Than Actinomycete Macrolides)," *Nat. Prod. Rep.*, 16(4):425-484 (1999).

Rock et al., "Increased Unsaturated Fatty Acid Production Associated with a Suppressor of the fabA6(Ts) Mutation in *Escherichia coli*," *J. Bacteriol.*, 178(18):5382-5387 (1996).

Scheibel, "The Evolution of Anionic Surfactant Technology to Meet the Requirements of the Laundry Detergent Industry," *Journal of Surfactants and Detergents*, 7(4):319-328 (2004).

Scheibel, "The Production of Alcohols and Alcohol Sulfates," Handbook of Detergents/Part F: Production, Zoller and Sosis Eds.pp. 117-137, CRC Press (2009).

Serrano-Ruiz et al., Conversion of Cellulose to Hydrocarbon Fuel by Progressive Removal of Oxygen, *Applied Catalysis B: Enviornmental*, 100(1-2):184-189 (2010).

Vougioukalakis et al., "Ruthenium-Based Heterocyclic Carbene-Coordinated Olefin Metathesis Catalysts," *Chem Rev.*, 110(3):1746-1787 (2010).

West et al., "Liquid Alkanes with Targeted Molecular Weights from Biomass-Derived Carbohydrates," *ChemSusChem*, 1(5):417-424 (2008).

West et al., "Production of Alkanes from Biomass Derived Carbohydrates on Bi-Functional Catalysis Employing Niobium-Based Supports," *Catalysis Communications*, 10(13):1743-1746 (2009).

Zhang et al., "The FabR (YijC) Transcription Factor Regulates Unsaturated Fatty Acid Biosynthesis in *Escherichia coli*," *J. Biol. Chem.*, 277(18):15558-15565 (2002).

International Search Report for PCT/US2012/025430 dated Apr. 19, 2012.

Cavalli L et al: "Update on LAB / LAS", Tenside, Surfactants, Detergents, Carl Hanser Verlag, Munchen, DE, vol. 36, No. 4, Jul. 1, 1999, pp. 254-258, XP000854154, ISSN: 0932-3414.

* cited by examiner

MIXTURES OF C10-C13 ALKYLPHENYL SULFONATES

CROSS REFERENCE TO RELATED APPLICATION

This application claims the benefit of U.S. Provisional Application No. 61/444,007, filed Feb. 17, 2011.

FIELD OF THE INVENTION

The invention is directed to a composition comprising a mixture of $C_{10}$-$C_{13}$ alkylphenyl sulfonates having a particular alkyl chain distribution (e.g., bimodal, peaked, skewed, and random). The invention is further directed to a method of making the mixture of $C_{10}$-$C_{13}$ alkylphenyl sulfonates.

BACKGROUND OF THE INVENTION

Surfactants are the single most important cleaning ingredient in cleaning products. Environmental regulations, consumer habits, and consumer practices have forced new developments in the surfactant industry to produce lower-cost, higher-performing, and environmentally friendly products. Examples of developments in the surfactant industry are described by J. Scheibel in the Journal of Surfactants and Detergents, "The Evolution of Anionic Surfactant Technology to Meet the Requirements of the Laundry Detergent Industry," volume 7, number 4, October, 2004 ("Scheibel JSD Article" hereinafter), which is incorporated herein by reference. Today, challenges facing the surfactant industry include colder wash temperatures, less efficient builders, liquid products without calcium control, and a push for reduced surfactant use overall because of the perceived environmental impact of surfactants.

Alkylphenyl sulfonates are surfactants derived from tetrapropylene that have very complex branching structures (e.g., 3 or 4 branches per molecule). The structure below illustrates one example of a hard alkylphenyl sulfonate molecule, which has branching near the polar head group and in the middle of the surfactant.

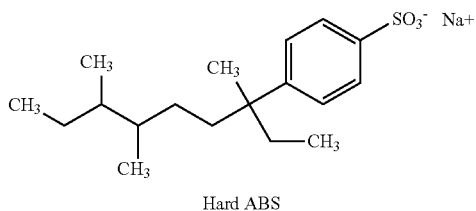

Hard ABS

ABS surfactants were prominent until the early 1960s when they were subjected to environmental regulations for being poorly biodegradable. Alkylphenyl sulfonate surfactants were then replaced with the readily biodegradable linear alkylphenyl sulfonate (LAS) surfactants, which are easily obtainable and currently in use today. Use of LAS surfactants and other similar linear surfactants is limited because they have poor solubility in cold water and hard water conditions. In fact, more than half of the LAS detergent in products may be lost during use due to the formation of multilayered vesicles that resemble large onion-like structures. Formulators can increase the solubility of linear surfactants, for example, by introducing cosurfactants or by using linear alcohol ethoxylated sulfates (AES). However, AES surfactants have lower surface activity, as well as lower mass efficiency than LAS surfactants. Further, the use of cosurfactants or AES surfactants limits formulation flexibility and can add substantial cost to the detergent. ABS, LAS, and AES surfactants are described in detail in the Scheibel JSD article.

Surfactants with light, mid-chain branching, such as highly soluble alcohol sulfate (HSAS) surfactants derived from petroleum feedstocks, were then developed for use in consumer products. HSAS surfactants are illustrated in the Scheibel JSD article, as well as U.S. Pat. Nos. 6,020,303; 6,060,443; and 6,335,312; and U.S. Patent Application Publication No. 2010/0137649, each incorporated herein by reference. The structure below illustrates one example of a HSAS surfactant, showing a single methyl branch near the mid-point of the surfactant.

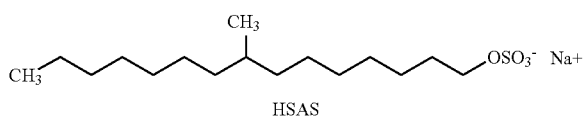

HSAS

Although the HSAS surfactants provide good cleaning ability in cold and hard water, have high solubility, good grease removal properties, and good biodegradability, too much branching prevents them from packing efficiently at the air-water interface. Also, if the total carbon chain length is too long, insufficient foam volume will be generated because bubble size will be greatly diminished. These two factors can severely limit the foamability of the technology. In some cases foamability and stability of foam are critical to the consumer goods application, such as in dishwashing liquids, hand wash detergents, and shampoos.

U.S. Pat. No. 6,306,817, incorporated herein by reference, describes alkylphenyl sulfonates that have light chain branching on their alkyl groups. According to the disclosure, these surfactants have superior cold water solubility, for example, for cold water laundering; superior hardness tolerance; and excellent detergency, especially under low temperature wash conditions. These surfactants also provide reduced build-up of old fabric softener residues from fabrics being laundered, and improved removal of lipid or greasy soils from fabrics.

U.S. Pat. No. 6,566,319, incorporated herein by reference, describes a method of making a mixture of $C_{11}$-$C_{14}$ alkylphenyl sulfonates using alkene feedstocks having particular chain lengths (e.g., an alkene feedstock with a total of 5, 6, and 7 carbon atoms, an alkene feedstock with a total of 5 and 7 carbon atoms, an alkene feedstock with a total of 6 and 7 carbon atoms, an alkene feedstock with a total of 6 or 7 carbon atoms). The process of the '319 patent is advantageous because it allows some degree of control over the chain length of the alkyl group on the alkylphenyl sulfonate. The method does not allow for specific alkyl chain distributions of the alkylphenyl sulfonate or for renewable alkylphenyl sulfonates.

Accordingly, it would be desirable to find detergent formulations that deliver even better performance and better value to the consumer, and to produce these formulations simply, efficiently, and in a controlled, cost effective manner. In view of the very large tonnages of alkylphenyl sulfonate surfactants and detergent formulations used worldwide, even modest improvements in performance of the basic alkylphenyl sulfonate detergent would have a significant impact.

SUMMARY OF THE INVENTION

In one aspect, the invention is directed to a mixture of $C_{10}$-$C_{13}$ alkenes that each independently have a total of 10-13 carbon atoms and 0-3 $C_1$-$C_2$ alkyl branches. The mixture of $C_{10}$-$C_{13}$ alkenes has a total carbon atom distribution selected from the group consisting of bimodal, peaked, skewed, and random. Further, the mixture comprises less than about 5 wt. % of alkenes with 9 or fewer carbon atoms and alkenes with 14 or more carbon atoms, based on the total weight of the mixture. Further still, the mixture of $C_{10}$-$C_{13}$ alkenes optionally comprises alkanes in an amount less than about 80 wt. %, preferably less than about 50 wt. %, more preferably less than about 25 wt. %, for example, less than about 5 wt. %. The mixture of $C_{10}$-$C_{13}$ alkenes optionally has a biobased content of at least about 5%, at least about 10%, at least about 20%, at least about 30%, at least about 40%, at least about 50%, at least about 60%, at least about 70%, at least about 80%, at least about 90%, at least about 95%, for example, about 100%. In some embodiments, the mixture of $C_{10}$-$C_{13}$ alkenes is substantially monounsaturated (i.e., less than about 10 wt. %, preferably less than about 5 wt. %, more preferably less than about 1 wt. % of polyunsaturated alkenes).

In another aspect, the invention is directed to a mixture comprising:
(a) $C_{10}$-$C_{13}$ alkylbenzenes; or
(b) $C_{10}$-$C_{13}$ alkylphenyl sulfonates.
The alkyl groups of the alkylbenzenes or alkylphenyl sulfonates each independently have a total of 10-13 carbon atoms, 0-3 $C_1$-$C_2$ alkyl branches, and comprise an alkyl chain distribution selected from the group consisting of bimodal, peaked, skewed, and random. Further, the mixture comprises less than about 5 wt. % of alkylbenzenes or alkylphenyl sulfonates that have alkyl groups with 9 or fewer carbon atoms and alkyl groups that have 14 or more carbon atoms, based on the total weight of the mixture. Further still, less than about 10 wt. % of the $C_{10}$-$C_{13}$ alkylbenzenes or the $C_{10}$-$C_{13}$ alkylphenyl sulfonates have two or more $C_{10}$-$C_{13}$ alkyl groups on the benzene or phenyl group, based on the total weight of the mixture. Even further, less than about 10 wt % of the $C_{10}$-$C_{13}$ alkylbenzenes or the $C_{10}$-$C_{13}$ alkylphenyl sulfonates have an alkyl group comprising a quaternary carbon atom, based on the total weight of the mixture. The mixture of $C_{10}$-$C_{13}$ alkylbenzenes or $C_{10}$-$C_{13}$ alkylphenyl sulfonates comprise alkyl groups that each optionally have a biobased content of at least about 5%, at least about 10%, at least about 20%, at least about 30%, at least about 40%, at least about 50%, at least about 60%, at least about 70%, at least about 80%, at least about 90%, at least about 95%, for example about 100%. The benzene portion of the $C_{10}$-$C_{13}$ alkylbenzenes or the phenyl moiety in the $C_{10}$-$C_{13}$ alkylphenyl sulfonates in the mixtures described each optionally have a biobased content of at least about 50%, preferably at least about 75%, more preferably at least about 95%, for example about 100%.

In another aspect, the invention is directed to a consumer product cleaning or personal care composition comprising about 0.001 wt. % to about 99.999 wt. %, preferably about 0.1 wt % to about 80 wt. %, of the mixture of $C_{10}$-$C_{13}$ alkylphenyl sulfonates, as described herein, based on the total weight of the composition, and 0.001 wt. % to about 99.999 wt. % of one or more additional cleaning components, or one or more additional personal care components.

In yet another aspect, the invention is directed to a method of making a mixture of partially or wholly renewable $C_{10}$-$C_{13}$ alkenes that have a controlled total carbon atom distribution (i.e., bimodal, peaked, skewed, and random). In this method, a fatty acid, a fatty ester, a fat, an oil, or mixtures thereof is reacted with an alkene having a total of 2 to 8 carbon atoms in the presence of a catalytically effective amount of a metathesis catalyst and under standard metathesis conditions. The fatty acid, fatty ester, fat, oil, or mixture thereof has an iodine value of at least about 15, as determined by the AOAC Official Method of Analysis (1984), Chapter 28.023. The mixture of alkenes produced by the metathesis method described herein has a biobased content of at least about 20 wt. %.

The mixture of $C_{10}$-$C_{13}$ alkenes that has a controlled total carbon atom distribution can be used to alkylate benzene to form the mixture $C_{10}$-$C_{13}$ alkylbenzenes described herein. The mixture of $C_{10}$-$C_{13}$ alkylbenzenes can be sulfonated to form the mixture of $C_{10}$-$C_{13}$ alkylphenyl sulfonates described herein.

All percentages, ratios and proportions herein are by weight, unless otherwise specified. All temperatures are in degrees Celsius (° C.) unless otherwise specified. All documents cited are in relevant part, incorporated herein by reference.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

The invention is directed to a composition comprising a mixture $C_{10}$-$C_{13}$ alkylphenyl sulfonates having a particular alkyl chain distribution (e.g., bimodal, peaked, skewed, random, and flat, as shown in FIGS. 1-5). The mixtures of $C_{10}$-$C_{13}$ alkylphenyl sulfonates are advantageous because they can be partially or wholly derived from renewable materials. Further, they are biodegradable, completely tunable (e.g., by altering the alkyl chain distribution), and provide superior performance when used alone or in consumer product cleaning and personal care cleaning compositions.

It has unexpectedly been found that the optionally renewable $C_{10}$-$C_{13}$ alkylphenyl sulfonates of the invention having particular alkyl chain distributions, when used alone or in consumer product cleaning or personal care compositions, have unpredicted, superior properties, such as improved solubility, sudsing performance, grease oil cleaning, and formulability. These mixtures of $C_{10}$-$C_{13}$ alkylphenyl sulfonates, or the $C_{10}$-$C_{13}$ alkylbenzene intermediates used to make the $C_{10}$-$C_{13}$ alkylphenyl sulfonates, also can be spiked into existing, petroleum-derived alkylbenzenes or alkylphenyl sulfonates that have random alkyl chain distributions to result in compositions with superior performance results. The particular alkyl chain distributions of the invention, particularly the bimodal distribution, have never before been recognized as valued distributions by the art.

Figure 6:
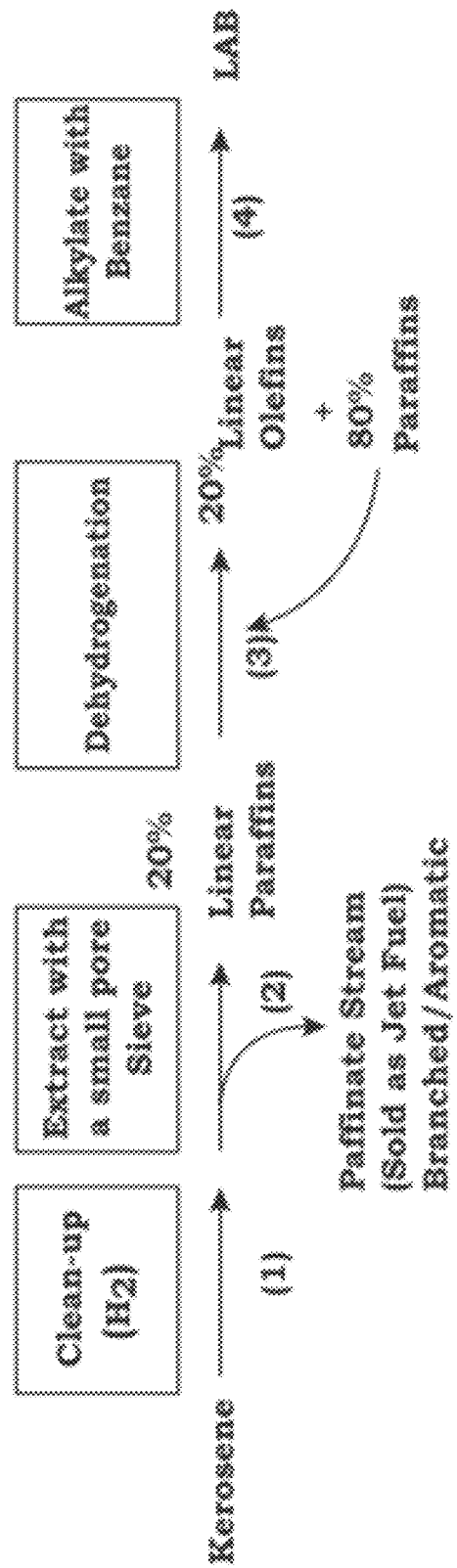
FIG. 6 depicts a five step commercial process for the production of linear alkylphenyl sulfonates. In this process, kerosene is hydrogenated to result in a raffinate stream that contains linear paraffins (20 wt. %). The linear paraffins are extracted using a small pore sieve and subjected to dehydrogenation to form linear alkenes (20 wt. %) and paraffins (80 wt. %). The linear alkene/paraffin mixtures are then used to alkylate benzene to form linear alkylbenzene and linear paraffin mixtures. The linear paraffin fraction is removed by distillation, as is the linear alkylbenzene fraction. The linear alkylbenzene fraction is subsequently sulfonated to form linear alkylphenyl sulfonate.

Further, no other commercially viable and cost effect approach had previously been industrially available or reported in literature for the synthesis of mixtures of optionally renewable $C_{10}$-$C_{13}$ alkylphenyl sulfonates having a particular alkyl distribution, as described herein. These distributions (e.g., a bimodal alkyl chain distribution with an average total carbon number of 10.9) previously have been unattainable using the traditional production source of alkylbenzenes and alkylphenyl sulfonates (e.g., petroleum distillates, such as kerosene, polyolefins from ethylene, and gas-to-liquid paraffins). For example, the commercial process for the production of linear alkylphenyl sulfonates is a five step process, as shown in FIG. 6. In this process, kerosene is hydrogenated to result in a raffinate stream that contains linear paraffins (20 wt. %). The linear paraffins are extracted using a small pore sieve and subjected to dehydrogenation to form linear alkenes (20 wt. %) and paraffins (80 wt. %). The linear alkene/paraffin mixtures are then used to alkylate benzene to form linear alkylbenzene and linear paraffin mixtures. The linear paraffin fraction is removed by distillation, as is the linear alkylbenzene fraction. The linear alkylbenzene fraction is subsequently sulfonated to form linear alkylphenyl sulfonate. This process cannot be used to form alkylbenzenes and alkylphenyl sulfonates that have $C_{10}$-$C_{13}$ alkyl chains in particular distributions because it is derived from a crude kerosene stream that contains all of the chain lengths present in refined kerosene. This process also is disadvantageous because the first three steps are costly and complex and the resulting products are derived from petroleum sources.

Further still, nature cannot provide mixtures of alkenes having the distributions of the invention, which can be used to form alkylbenzenes and alkylphenyl sulfonates. Nature does provide alkenes with predominantly even chain length distributions in fats and oils, but these distributions contain only $C_8$, $C_{10}$, $C_{12}$, $C_{14}$, $C_{16}$, and $C_{18}$ fatty acid moieties and cannot easily be manipulated to form the particular distributions of the invention, which have a narrower range of total carbon number, as well as moieties with both an even and an odd number of carbon atoms. Further still, these fats and oils are not naturally in a form that can be used for the alkylation of benzene because they are too functionalized and require expensive, high temperature, decarboxylation chemistry, which disadvantageously increases the environmental footprint of the product due to the carbon dioxide that is produced. Although Neste Oil's process theoretically can be used to produce a mixture of $C_{10}$, $C_{12}$, and $C_{14}$ alkanes with some low levels of odd chain lengths from a limited and expensive supply of palm kernel oil, current specifications for alkylbenzenes require less than 1 wt. % of $C_{14}$ content, based on the total weight of the alkylbenzenes. Thus, an outlet for the $C_{14}$ paraffin fraction is required, adding to the expense of making the desired mixtures of optionally renewable alkylbenzenes. Similarly, tallow also includes chain lengths outside the scope of the invention, and does not include odd numbered chains. Odd chain or even chain fatty acid biosynthesis can be used to make even chain or odd chain olefins and alkanes, respectively, starting with propionyl-CoA instead or acetyl-CoA, respectively (Ingram et al., J. of Bacteriology 131(3):1023-1025 (1977), incorporated herein by reference), but cannot achieve mixtures of odd and even chain olefins and alkanes having the specific distributions of the invention.

Existing technologies for the conversion of natural feedstocks (e.g., fats, oils) into alkylbenzenes and alkylphenyl sulfonates cannot provide the control or diversity necessary to result in the alkylbenzenes and alkylphenyl sulfonates of the invention, which have a particular alkyl chain distribution, without increasing the environmental footprint of the product, adding expensive processing costs, or using processes that require high energy (e.g., temperatures greater than about 300° C.).

This invention also provides a method of making mixtures of partially or wholly renewable $C_{10}$-$C_{13}$ alkylphenyl sulfonates having a particular alkyl chain distribution. These mixtures were previously unattainable using traditional methods of synthesis in a cost effective manner. In the method of the invention, a mixture of partially or wholly renewable $C_{10}$-$C_{13}$ alkenes having a particular alkyl chain distribution is synthesized by the metathesis of fatty acids, fatty esters, fats, and/or oils with optionally renewable short chain alkenes. The resulting mixture of $C_{10}$-$C_{13}$ alkenes is used to alkylate benzene to form a mixture of partially or wholly renewable $C_{10}$-$C_{13}$ alkylbenzenes having a particular alkyl chain distribution. These alkylbenzenes then are sulfonated to form the mixture of $C_{10}$-$C_{13}$ alkylphenyl sulfonates of the invention.

The metathesis process of the invention can be used to replace traditional methods for the production of alkylphenyl sulfonates that use kerosene feedstock. The traditional kerosene process is inefficient and requires multiple process steps to convert kerosene to linear paraffins (see FIG. 6). Further, only about 20% of the alkenes that are produced by the process undergo alkylation, requiring recycling of the paraffin back into the dehydrogenation process. Because plants that produce linear alkylbenzenes are large with large recycle streams, about 1000 KMTA of kerosene is needed to run the plant, while only about 150 KMTA of alkylbenzenes are produced. In contrast, the metathesis process of the invention has increased throughput in alkylation per unit of starting material, making the cost savings that is available for new plants economically competitive with the traditional system. Further, simple stirred batch reactors can be used for the method of the invention without any special steel requirement. As a result, an affordable multiple reactor system can be used that allows the composition of the products of metathesis to be tailored by running multiple batch reactors with different short chain alkene feeds, and then post-blending the resulting alkenes to economically make up the mixtures of the invention. The ability to use multiple batch reactors with different short chain alkene feeds currently is not feasible with the previously described petroleum-based process because the kerosene is a gross mixture of components that have different chain lengths and different branching. Controlling or selecting either the total number of carbon atoms in the chain or type of branching of the chain is challenging and costly.

The metathesis process to produce the alkenes of the invention is advantageous because the feedstock can include crude starting materials that contain, for example, paraffin, isoparaffin, and aromatic contaminants because these contaminants are unreactive during the metathesis process, yet can easily be distilled from the product. Further still, the metathesis route has a simple reaction design with a minimum number of reaction steps, avoiding the use of complex fractionation of fuel feedstocks, which is cost prohibitive, as well as three of the complex and costly steps that are commercially used to synthesize petroleum-based alkylphenyl sulfonates (i.e., hydrogenation of kerosene, extraction of linear paraffins, and dehydrogenation of linear paraffins), as described above. It results in a clean mixture of $C_{10}$-$C_{13}$ alkenes that are easily separable from the triglyceride side products through simple distillation, without requiring fractional distillation. This clean mixture of alkenes can, in some situations, be directly reacted in the alkylation reaction to form alkylbenzenes without substantial work-up or purification (e.g., sieving, concentration). In other situations, the metathesis derived alkenes can contain some di- or tri-alkenes, possibly requiring partial hydrogenation to mono-alkenes to limit the formation of undesirable tetralins and/or indans during the alkylation process. These impurities (e.g., tetralins and indans) are not as biodegradable as linear alkylbenzenes and linear alkylphenyl sulfonates. The alkenes that result from the metathesis reaction are also useful for other purposes beside the alkylation of benzene, such as for the formation of alcohols by hydroformylation and subsequent reduction.

Using metathesis chemistry to produce a mixture of $C_{10}$-$C_{13}$ alkenes with a controlled total carbon atom distribution allows for tunability of the $C_{10}$-$C_{13}$ alkene distribution through the selection of the short chain alkene starting material. For example, a formulator can select short chain alkene starting materials having a particular chain length distribution to meet the criteria of different cleaning composition formulations (e.g., dishwashing liquids, liquid laundry detergent, granular detergent). The formulator also can select alkyl chains having a particular degree and location of branching to meet biodegradability needs (e.g., some branched alkylbenzenes and alkylphenyl sulfonates have improved biodegradability).

The feedstock for the metathesis reaction of the invention (e.g., fatty acids, fatty esters, fats, oils, short chain alkenes) is also advantageous over petroleum feedstocks for the formation of mixtures of $C_{10}$-$C_{13}$ alkenes. Current feedstocks from petroleum resources have some short chain contamination (e.g, $C_8$, $C_9$). This short chain contamination is carried through the subsequent alkylation step to form alkylbenzenes having short chain contaminants. If incomplete sulfonation occurs during the surfactant making process, these short chains can affect the volatile organic carbon (VOC) in spray tower detergent processing. Some states require substantial emission control to limit release of such VOC and can be subject to fines if these limits are exceeded in a processing plant performing sulfonation or spray tower drying of surfactants. In contrast, short chain contamination cannot exist in the process of the invention. Furthermore, the feedstock for this metathesis process (e.g., fatty acids, fatty ester, fats, oils, short chain alkenes) can be obtained at low cost.

The metathesis process of the invention generates three value added products: glycerin, alkene-terminated and near terminal olefinic acids and esters, and bio-alkene feedstock. Glycerin is commercially used, for example, for solvents and foods. Alkene-terminated and near terminal olefinic acids and esters can be commercially used for specialty applications, such as antimicrobials, polymer crosslinkers, and the generation of unique diacids, as described in the following presentations: Cargill, "Cargill's Activities to Develop Industrial Chemicals From Plants," Plant Bio-Industrial Oils Workshop, February 2006, and Elevance, "Novel Renewable Chemicals, Transforming Markets with New Building Blocks, March 2010, each incorporated herein by reference. Bio-alkene feedstock can be used to form the alkylphenyl sulfonates of the invention or to form linear or branched bio-alcohols via hydroformylation and subsequent reduction.

The particular alkyl chain distributions of the mixtures of $C_{10}$-$C_{13}$ alkylbenzenes and alkylphenyl sulfonates of the invention are themselves advantageous during the formation of $C_{10}$-$C_{13}$ alkylphenyl sulfonates because they simplify the purification process. Typically, a difference in chain length of three carbon atoms (e.g., $C_8$ versus $C_{11}$) is necessary to allow purification by simple distillation. Separating chains without a difference in length of three carbon atoms (e.g., $C_9$ versus $C_{10}$) is not only extremely difficult, but also cost prohibitive. The alkyl distributions of the invention have a great enough difference in chain length to avoid difficult and costly separation techniques.

As used herein, "biobased content" refers to the amount of bio-carbon in a material as a percent of the weight (mass) of the total organic carbon in the product. For example, ethylene contains two carbon atoms. If ethylene is derived from a renewable resource, it has a biobased content of 100% because all of the carbon atoms are derived from a renewable resource. As another example, undecylbenzene contains 17 carbon atoms (i.e., 11 from the undecyl alkyl chain and 6 from the phenyl group). If the undecyl group is derived from a renewable resource, but the phenyl group is derived from a petroleum-based resource, the theoretical biobased content of the undecylbenzene is about 65%.

As used herein, a "renewable" compound or material is one that is partially or wholly derived from a renewable resource. In a partially renewable compound or material, at least one, but not all of its carbon atoms is derived from a renewable resource. In a wholly renewable compound or material, all of its carbon atoms are derived from a renewable resource.

As used herein, a "renewable resource" is one that is produced by a natural process at a rate comparable to its rate of consumption (e.g., within a 100 year time frame). The resource can be replenished naturally, or via agricultural techniques. Renewable resources include plants (e.g., sugar cane, beets, corn, potatoes, citrus fruit, woody plants, lignocellulosics, hemicellulosics, cellulosic waste), animals, fish, bacteria, fungi, and forestry products. These resources can be naturally occurring, hybrids, or genetically engineered organisms. Natural resources such as crude oil, coal, and peat, which take longer than 100 years to form, are not considered renewable resources. Nonlimiting examples of renewable polymers include polymers produced directly from organisms, such as polyhydroxyalkanoates (e.g., poly(beta-hydroxyalkanoate), poly(3-hydroxybutyrate-co-3-hydroxyvalerate, NODAX™), and bacterial cellulose; polymers extracted from plants and biomass, such as polysaccharides and derivatives thereof (e.g., gums, cellulose, cellulose esters, chitin, chitosan, starch, chemically modified starch), proteins (e.g., zein, whey, gluten, collagen), lipids, lignins, and natural rubber; and polymers derived from naturally sourced monomers and derivatives, such as bio-polyethylene, polytrimethylene terephthalate, polylactic acid, NYLON 11, alkyd resins, and succinic acid-based polyesters.

The term "bio-" placed as a prefix means that at least a portion of the carbon atoms of the component are derived from a renewable resource. Also included within this definition are those components that are produced naturally in plants. For example, bio-limonene and bio-isobornyl alcohol can be harvested from various plants. While the component may be capable of being derived from petroleum feedstock, the prefix is intended to exclude those components that specifically derive all of their carbon atoms from petroleum feedstock. As an example, "bio-ethanol" means ethanol that is formed from renewable resources. Catalysts, solvents, or other adjuvants that are used to facilitate the reaction, but do not form a part of the final bio-component, do not necessarily need to be derived from a renewable resource.

As used herein, the term "biodegradable" refers to compounds and materials that are capable of undergoing natural decomposition into carbon dioxide, methane, water, inorganic compounds, biomass, or a mixture thereof, in which the predominant mechanism is the enzymatic action of microorganisms that can be measured by standardized tests, in a specified time, reflecting relevant disposal conditions. In the presence of oxygen (aerobic biodegradation), these metabolic processes yield carbon dioxide, water, biomass, and minerals. Under anaerobic conditions (anaerobic biodegradation), methane may additionally be produced.

As used herein, the term "alkyl" refers to straight chain and branched chain saturated hydrocarbon groups, nonlimiting examples of which include methyl, ethyl, and straight and branched propyl, butyl, pentyl, hexyl, heptyl, and octyl groups containing the indicated number of carbon atoms. The term $C_n$ means the alkyl group has "n" carbon atoms. For example, $(C_1-C_7)$alkyl refers to an alkyl groups having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms).

As used herein, a "$C_{10}$-$C_{13}$ alkene" is a monounsaturated or unconjugated, polyunsaturated hydrocarbon having 10 to 13 total carbon atoms (e.g., 10, 11, 12, or 13 total carbon atoms, as well as all subgroups, such as 10-13, 10-12, 10-11, 11-13, 11-12, 12-13 total carbon atoms).

Mixtures of Optionally Renewable $C_{10}$-$C_{13}$ Alkenes

In one aspect, the invention relates to a mixture of alkenes. Each alkene in the mixture independently has a total of 10, 11, 12, or 13 carbon atoms and that can optionally include up to 3 (e.g., 0, 1, 2, or 3) methyl branches, ethyl branches, or a mixture of methyl and ethyl branches. In some embodiments, the mixture of alkenes is substantially monounsaturated (i.e., at least about 90 wt. %, preferably at least about 95 wt. %, more preferably at least about 99 wt. % of monounsaturated alkenes).

The mixture of $C_{10}$-$C_{13}$ alkenes comprises less than about 5 wt. %, preferably less than about 3 wt. %, more preferably less than about 1 wt. %, for example about 0 wt. % of alkenes that have 9 or fewer carbon atoms and alkenes that have 14 or more carbon atoms, based on the total weight of the mixture. In some embodiments, the mixture of $C_{10}$-$C_{13}$ alkenes comprises about 0.1 wt. % to about 5 wt. % of alkenes that have a total of 14 carbon atoms, based on the total weight of the mixture. Alkenes having 9 or fewer carbon atoms are undesirable because alkylphenyl sulfonates that have alkyl groups with 9 or fewer carbon atoms are volatile during detergent processing conditions. Alkenes having 14 or more carbon atoms are undesirable because they produce alkylphenyl sulfonates that have a higher toxicity concentration with organisms in the environment than alkylphenyl sulfonates that have alkyl groups with a total of 10, 11, 12, or 13 carbon atoms, which also are more easily biodegradable.

Further, the mixture of $C_{10}$-$C_{13}$ alkenes optionally comprises alkanes in an amount less than about 80 wt. %, preferably less than about 50 wt. %, more preferably less than about 25 wt. %, for example, less than about 5 wt. %. Further still, the mixture of $C_{10}$-$C_{13}$ alkenes comprises less than about 10 wt. %, preferably less than about 5 wt. %, more preferably less than about 1 wt. % of oxygen-containing compounds (e.g., fatty esters). The mixture of $C_{10}$-$C_{13}$ alkenes optionally has a biobased content of at least about 5%, at least about 10%, at least about 20%, at least about 30%, at least about 40%, at least about 50%, at least about 60%, at least about 70%, at least about 80%, at least about 90%, at least about 95%, for example about 100%.

Figure 1A:
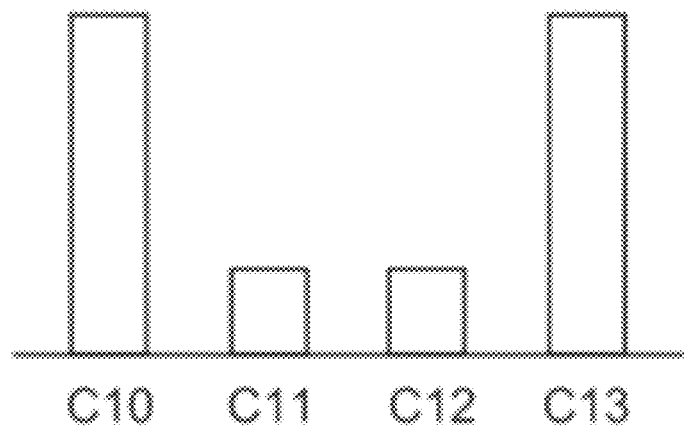
FIGS. 1A-C pictorially represent examples of alkenes and/or alkyl chains having bimodal distributions.
Figure 1B:
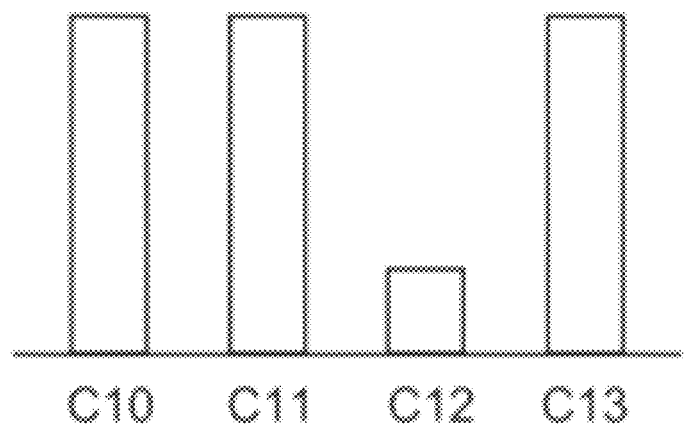
Figure 1C:
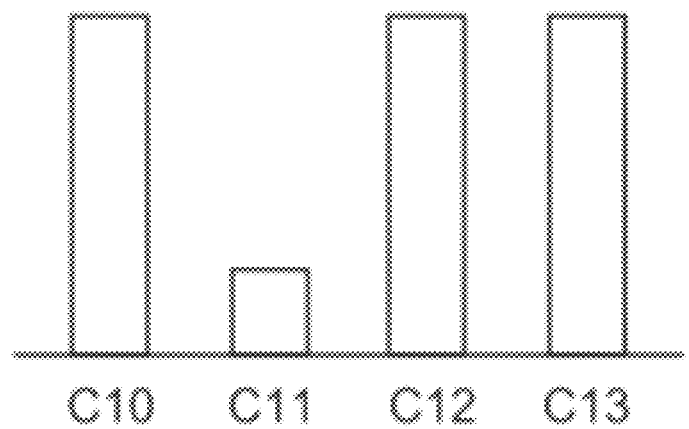
Figure 2A:
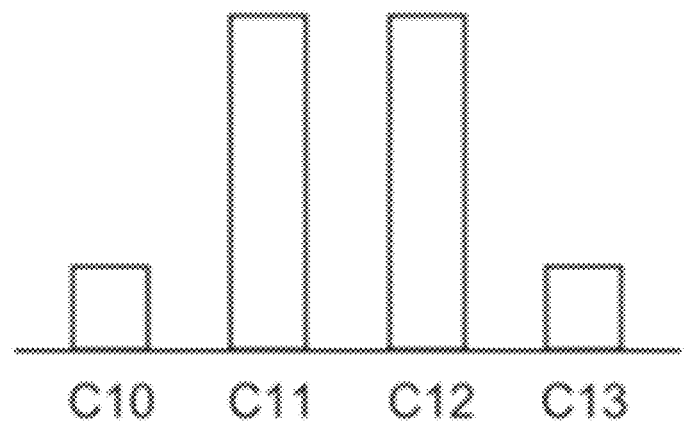
FIGS. 2A-C pictorially represents an example of alkenes and/or alkyl chains having a peaked distribution.
Figure 2B:
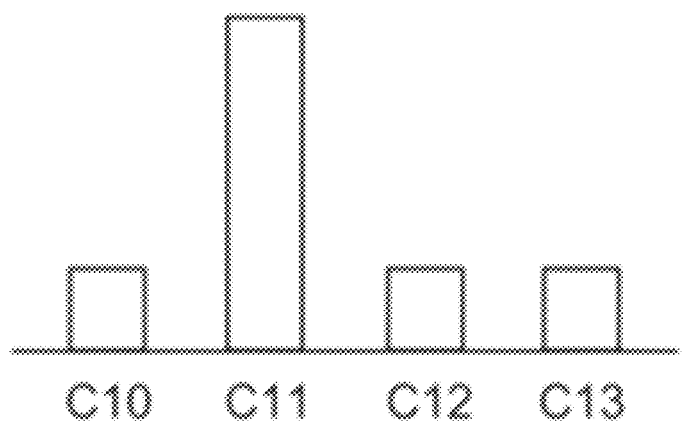
Figure 2C:
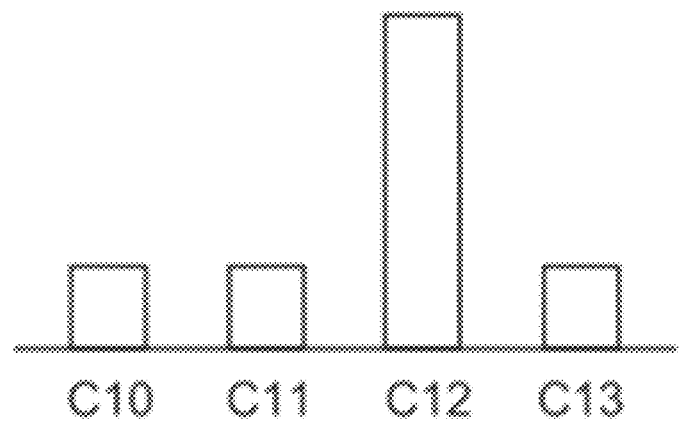
Figure 3A:
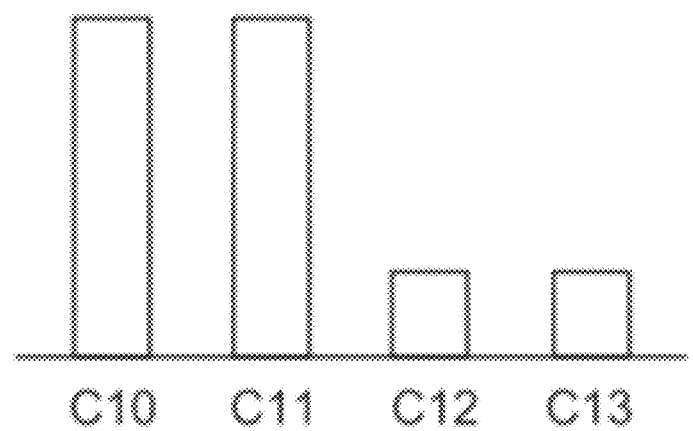
FIGS. 3A-D pictorially represents examples of alkenes and/or alkyl chains having skewed distributions.
Figure 3B:
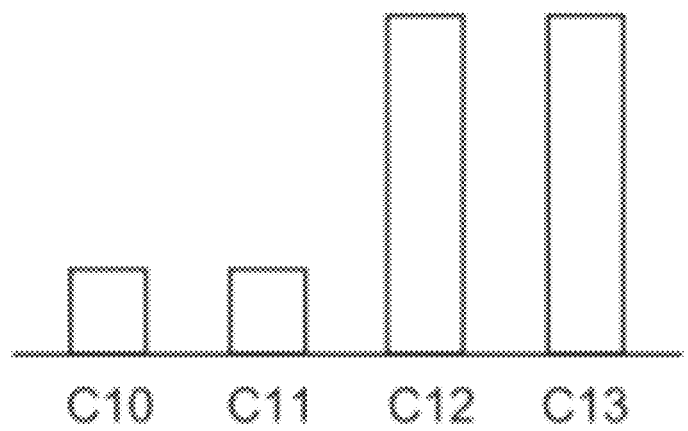
Figure 3C:
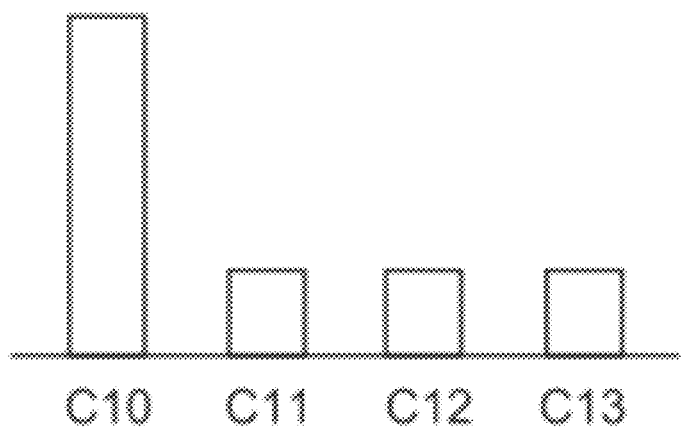
Figure 3D:
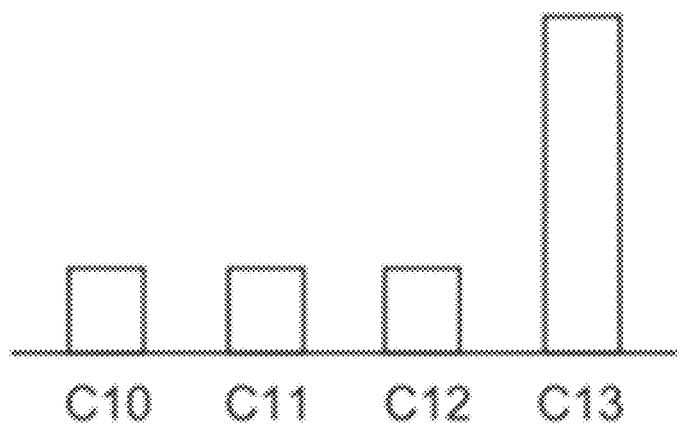
Figure 4:
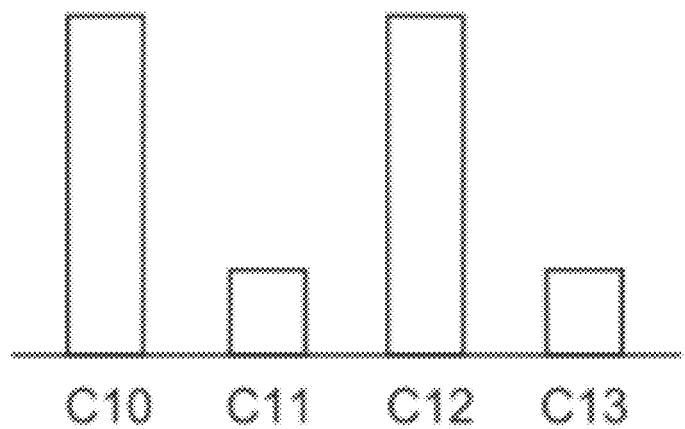
FIG. 4 pictorially represents an example of alkene sand/or alkyl chains having a random distribution.
Figure 5:
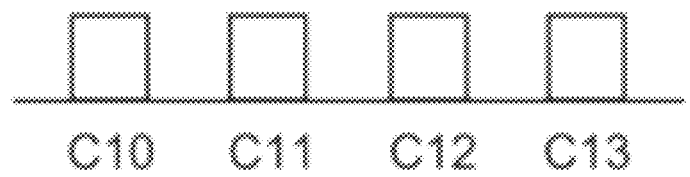
FIG. 5 pictorially represents an example of alkenes and/or alkyl chains having a flat distribution.

The $C_{10}$-$C_{13}$ alkenes in the mixture have a total carbon atom distribution that is bimodal (i.e., two peaks, see, e.g., FIG. 1), peaked (i.e., one symmetrical peak, see, e.g., FIG. 2), skewed (i.e., one unsymmetrical peak, see, e.g., FIG. 3), random (see, e.g., FIG. 4), or flat (see, e.g., FIG. 5).

Bimodal Distribution

In embodiments when the mixture of $C_{10}$-$C_{13}$ alkenes has a total carbon atom distribution that is bimodal, the mixture comprises:
  (a) $C_{10}$ and $C_{13}$ alkenes to $C_{11}$ and $C_{12}$ alkenes; or
  (b) $C_{10}$, $C_{11}$, and $C_{13}$ alkenes to $C_{12}$ alkenes; or
  (c) $C_{10}$, $C_{12}$, and $C_{13}$ alkenes to $C_{11}$ alkenes
in a weight ratio of at least about 60 to about 40, preferably at least about 80 to about 20, more preferably at least about 90 to about 10, for example at least about 99 to about 1. In some specific bimodal distribution embodiments, the average number of total carbon atoms is about 10.9.

Optionally renewable $C_{10}$-$C_{13}$ alkenes having a bimodal distribution can be used to alkylate benzene, which after subsequent sulfonation, provide optionally renewable $C_{10}$-$C_{13}$ alkylphenyl sulfonates that have unexpectedly superior performance properties when used alone or in consumer product cleaning and personal care compositions. Some of these improved properties include solubility, sudsing performance, grease oil cleaning, and formulability.

Peaked Distribution

In embodiments when the mixture of $C_{10}$-$C_{13}$ alkenes has a total carbon atom distribution that is peaked, the mixture comprises $C_{11}$ and $C_{12}$ alkenes to $C_{10}$ and $C_{13}$ alkenes in a weight ratio of at least about 60 to about 40, preferably at least about 80 to about 20, more preferably at least about 90 to about 10, for example at least about 99 to about 1. In some specific embodiments, the average number of total carbon atoms is about 11.5.

Optionally renewable $C_{10}$-$C_{13}$ alkenes having a peaked distribution can be used to alkylate benzene, which after subsequent sulfonation, provide optionally renewable $C_{10}$-$C_{13}$ alkylphenyl sulfonates that have unexpectedly superior performance properties (e.g., grease removal properties) when used alone or in consumer product cleaning and personal care compositions.

Skewed Distribution

In embodiments when the mixture of $C_{10}$-$C_{13}$ alkenes has a total carbon atom distribution that is skewed, the mixture comprises:
  (a) $C_{10}$ and $C_{11}$ alkenes to $C_{12}$ and $C_{13}$ alkenes; or
  (b) $C_{12}$ and $C_{13}$ alkenes to $C_{10}$ and $C_{11}$ alkenes; or
  (c) $C_{10}$ alkenes to $C_{11}$, $C_{12}$, and $C_{13}$ alkenes; or
  (d) $C_{13}$ alkenes to $C_{10}$, $C_{11}$, and $C_{12}$ alkenes.
in a weight ratio of at least about 60 to about 40, preferably at least about 80 to about 20, more preferably at least about 90 to about 10, for example at least about 99 to about 1.

Optionally renewable $C_{10}$-$C_{13}$ alkenes having a skewed distribution can be used to alkylate benzene, which after subsequent sulfonation, provide optionally renewable $C_{10}$-$C_{13}$ alkylphenyl sulfonates that have unexpectedly superior performance properties, such as improved solubility, sudsing ability, and grease removal on fabrics, when used alone or in consumer product cleaning and personal care compositions.

Random Distribution

In some embodiments, the mixtures of optionally renewable $C_{10}$-$C_{13}$ alkenes have total a carbon atom distribution that is a random distribution. These mixtures are advantageous because they can be used as a direct replacement for, or in combination with, traditional, petroleum-based alkenes without altering existing supplier processes, changing existing specifications, or reassessing environmental performance. As direct replacements, the optionally renewable $C_{10}$-$C_{13}$ alkenes will process identically in terms of formulatibility in a detergent matrix, and will not require further optimization in terms of other attributes, such as sudsing and viscosity of the detergent formulation.

Features

The mixture of $C_{10}$-$C_{13}$ alkenes can comprise linear alkenes, branched alkenes, or both linear and branched alkenes. In some embodiments when the mixture comprises both linear and branched alkenes, the linear alkenes can be present in an amount of at least about 40 wt. %, at least about 50 wt. %, at least about 60 wt. %, at least about 70 wt. %, at least about 80 wt. %, at least about 90 wt. %, or about 100 wt. %, based on the total weight of the mixture. In some embodiments when the mixture comprises both linear and branched alkenes, the mixture comprises at least about 40 wt. %, at least about 50 wt. %, at least about 60 wt. %, at least about 70 wt. %, at least about 80 wt. %, at least about 90 wt. %, or about 100 wt. %, branched alkenes, based on the total weight of the mixture.

Other nonlimiting examples of the $C_{10}$-$C_{13}$ alkenes include those listed in the below tables.

| # Branches | Total of 10 Carbon Atoms |
|---|---|
| 0 | 1-decene; 2-decene; 3-decene; 4-decene; 5-decene |
| 1 | 2-methyl-1-nonene; 3-methyl-1-nonene; 2-methyl-2-nonene; 3-methyl-2-nonene; 2-methyl-3-nonene; 3-methyl-3-nonene; 2-methyl-4-nonene; 3-methyl-4-nonene; 2-methyl-5-nonene; 3-methyl-5-nonene; 3-ethyl-1-octene; 3-ethyl-2-octene; 3-ethyl-3-octene; 3-ethyl-4-octene |
| 2 | 2,3-dimethyl-1-octene; 2,3-dimethyl-2-octene; 2,3-dimethyl-3-octene;2,3-dimethyl-4-octene |

| # Branches | Total of 11 Carbon Atoms |
|---|---|
| 0 | 1-undecene; 2-undecene; 3-undecene; 4-undecene; 5-undecene |
| 1 | 2-methyl-1-decene; 3-methyl-1-decene; 4-methyl-1-decene; 2-methyl-2-decene; 3-methyl-2-decene; 4-methyl-2-decene; 2-methyl-3-decene; 3-methyl-3-decene; 4-methyl-3-decene; 2-methyl-4-decene; 3-methyl-4-decene; 4-methyl-4-decene; 2-methyl-5-decene; 3-methyl-5-decene; 4-methyl-5-decene; 3-ethyl-1-nonene |
| 2 | 2,3-dimethyl-1-nonene; 2,3-dimethyl-2-nonene; 2,3-dimethyl-3-nonene; 2,3-dimethyl-4-nonene |

| # Branches | Total of 12 Carbon Atoms |
|---|---|
| 0 | 1-dodecene; 2-dodecene; 3-dodecene; 4-dodecene; 5-dodecene; 6-dodecene |
| 1 | 2-methyl-1-undecene; 3-methyl-1-undecene; 4-methyl-1-undecene; 2-methyl-2-undecene; 3-methyl-2-undecene;4-methyl-2-undecene; 2-methyl-3-undecene; 3-methyl-3-undecene; 4-methyl-3-undecene; 2-methyl-4-undecene; 3-methyl-4-undecene; 4-methyl-4-undecene; 2-methyl-5-undecene; 3-methyl-5-undecene; 4-methyl-5-undecene; 3-ethyl-1-decene, 4-ethyl-1-decene; 3-ethyl-2-decene, 4-ethyl-2-decene; |
| 2 | 3-ethyl-3-decene, 4-ethyl-3-decene; 3-ethyl-4-decene, 4-ethyl-4-decene; 3-ethyl-5-decene, 4-ethyl-5-decene 2,3-dimethyl-1-decene; 3,4-dimethyl-1-decene; 2,3-dimethyl-2-decene;3,4-dimethyl-2-decene; 2,3-dimethyl-3-decene; 3,4-dimethyl-3-decene; 2,3-dimethyl-4-decene; 3,4-dimethyl-4-decene; 2,3-dimethyl-5-decene;3,4-dimethyl-5-decene; 3-ethyl-2-methyl-1-nonene; 3-ethyl-2-methyl-2-nonene; 3-ethyl-2-methyl-3-nonene; 3-ethyl-2-methyl-4-nonene |

| # Branches | Total of 13 Carbon Atoms |
|---|---|
| 0 | 1-tridecene; 2-tridecene; 3-tridecene; 4-tridecene; 5-tridecene; 6-tridecene |
| 1 | 2-methyl-1-dodecene; 3-methyl-1-dodecene; 4-methyl-1-dodecene; 2-methyl-2-dodecene; 3-methyl-2-dodecene; 4-methyl-2-dodecene; 2-methyl-3-dodecene; 3-methyl-3-dodecene; 4-methyl-3-dodecene; 2-methyl-4-dodecene; 3-methyl-4-dodecene; 4-methyl-4-dodecene; 2-methyl-5-dodecene; 3-methyl-5-dodecene; 4-methyl-5-dodecene; 2-methyl-6-dodecene; 3-methyl-6-dodecene; 4-methyl-6-dodecene; 3-ethyl-1-dodecene; 4-ethyl-1-dodecene; 3-ethyl-2-dodecene; 4-ethyl-2-dodecene; 3-ethyl-3-dodecene; 4-ethyl-3-dodecene; 3-ethyl-4-dodecene; 4-ethyl-4-dodecene; 3-ethyl-5-dodecene; 4-ethyl-5-dodecene; 3-ethyl-6-dodecene; 4-ethyl-6-dodecene |
| 2 | 2,3-dimethyl-1-undecene; 3,4-dimethyl-1-undecene; 2,3-dimethyl-2-undecene; 3,4-dimethyl-2-undecene; 2,3-dimethyl-3-undecene; 3,4-dimethyl-3-undecene; 2,3-dimethyl-4-undecene; 3,4-dimethyl-4-undecene; 2,3-dimethyl-5-undecene; 3,4-dimethyl-5-undecene; 3-ethyl-2-methyl-1-decene; 3-ethyl-4-methyl-1-decene; 4-ethyl-2-methyl-1-decene; 4-ethyl-3-methyl-1-decene; 3-ethyl-2-methyl-2-decene; 3-ethyl-4-methyl-2-decene; 4-ethyl-2-methyl-2-decene; 4-ethyl-3-methyl-2-decene; 3-ethyl-2-methyl-3-decene; 3-ethyl-4-methyl-3-decene; 4-ethyl-2-methyl-3-decene; 4-ethyl-3-methyl-3-decene; 3-ethyl-2-methyl-4-decene; 3-ethyl-4-methyl-4-decene; 4-ethyl-2-methyl-4-decene; 4-ethyl-3-methyl-4-decene; 3-ethyl-2-methyl-5-decene; 3-ethyl-4-methyl-5-decene; 4-ethyl-2-methyl-5-decene; 4-ethyl-3-methyl-5-decene |
| 3 | 2,3,4-trimethyl-1-decene; 2,3,4-trimethyl-2-decene; 2,3,4-trimethyl-3-decene; 2,3,4-trimethyl-4-decene; 2,3,4-trimethyl-5-decene |

Mixtures of Optionally Renewable $C_{10}$-$C_{13}$ Alkylbenzenes

In another aspect, the invention relates to a mixture of $C_{10}$-$C_{13}$ alkylbenzenes having a controlled alkyl chain distribution. The alkyl groups on the alkylbenzenes each independently have a total of 10, 11, 12, or 13 carbon atoms, and can optionally include up to 3 (e.g., 0, 1, 2, or 3) methyl branches, ethyl branches, or a mixture of methyl and ethyl branches. The mixtures of $C_{10}$-$C_{13}$ alkylbenzenes comprise less than about 5 wt. %, preferably less than about 3 wt. %, more preferably less than about 1 wt. %, for example about 0 wt. % of alkylbenzenes with alkyl groups that have 9 or fewer carbon atoms and alkylbenzenes with alkyl groups that have 14 or more carbon atoms, based on the total weight of the mixture. In some embodiments, the mixture of $C_{10}$-$C_{13}$ alkylbenzenes comprises about 0.1 wt. % to about 5 wt. % of alkylbenzenes with alkyl groups that have a total of 14 carbon atoms, based on the total weight of the mixture. Alkylbenzenes having alkyl groups with 9 or fewer carbon atoms are undesirable because they produce alkylphenyl sulfonates that have alkyl groups with 9 or fewer carbon atoms, which are volatile during detergent processing conditions. Alkylbenzenes having alkyl groups with 14 or more carbon atoms are undesirable because they produce alkylphenyl sulfonates that have a higher toxicity concentration with organisms in the environment than alkylphenyl sulfonates that have alkyl chains with a total of 10, 11, 12, or 13 carbon atoms, which also are more easily biodegradable.

Further, the mixture of $C_{10}$-$C_{13}$ alkylbenzenes comprises less than about 10 wt. %, preferably less than about 7 wt. %, more preferably less than about 5 wt. %, even more preferably less than about 3 wt. %, for example, less than about 1 wt. % of $C_{10}$-$C_{13}$ alkylbenzenes having two or more $C_{10}$-$C_{13}$ alkyl groups on benzene, based on the total weight of the mixture. Still further, the mixture of $C_{10}$-$C_{13}$ alkylbenzenes comprises less than about 10 wt. %, preferably less than about 7 wt. %, more preferably less than about 5 wt. %, even more preferably less than about 3 wt. %, for example, less than about 1 wt. % of $C_{10}$-$C_{13}$ alkylbenzenes having an alkyl group comprising a quaternary carbon atom, based on the total weight of the mixture.

The mixture of $C_{10}$-$C_{13}$ alkylbenzenes comprise alkyl groups that each optionally have a biobased content of at least about 5%, at least about 10%, at least about 20%, at least about 30%, at least about 40%, at least about 50%, at least about 60%, at least about 70%, at least about 80%, at least about 90%, at least about 95%, for example about 100%. The benzene portion of the $C_{10}$-$C_{13}$ alkylbenzenes in the mixtures described each optionally have a biobased content of at least about 50%, preferably at least about 75%, more preferably at least about 95%, for example about 100%.

The mixture of $C_{10}$-$C_{13}$ alkylbenzenes have an alkyl chain distribution that is bimodal, peaked, skewed, random, or flat.

Bimodal Alkyl Chain Distribution

In embodiments when the alkyl chain distribution is bimodal, the mixture comprises $C_{10}$-$C_{13}$ alkylbenzenes having:
(a) $C_{10}$ and $C_{13}$ alkyl groups to $C_{11}$ and $C_{12}$ alkyl groups; or
(b) $C_{10}$, $C_{11}$, and $C_{13}$ alkyl groups to $C_{12}$ alkyl groups; or
(c) $C_{10}$, $C_{12}$, and $C_{13}$ alkyl groups to $C_{11}$ alkyl groups.
in a weight ratio of at least about 60 to about 40, preferably at least about 80 to about 20, more preferably at least about 90 to about 10, for example at least about 99 to about 1. In some specific bimodal alkyl chain distribution embodiments, the average number of carbon atoms of the alkyl chain is about 10.9.

Optionally renewable $C_{10}$-$C_{13}$ alkylbenzenes having a bimodal alkyl chain distribution can be sulfonated to provide optionally renewable $C_{10}$-$C_{13}$ alkylphenyl sulfonates that have unexpectedly superior performance properties when used alone or in consumer product cleaning or personal care compositions. Some of these improved properties include solubility, sudsing performance, grease oil cleaning, and formulability.

Peaked Alkyl Chain Distribution

In embodiments when the $C_{10}$-$C_{13}$ alkylbenzenes have an alkyl distribution that is peaked, the mixture comprises $C_{10}$-$C_{13}$ alkylbenzenes having $C_{11}$ and $C_{12}$ alkyl groups to $C_{10}$ and $C_{13}$ alkyl groups in a weight ratio of at least about 60 to about 40, preferably at least about 80 to about 20, more preferably at least about 90 to about 10, for example at least about 99 to about 1. In some specific peaked alkyl chain distribution embodiments, the average number of carbon atoms of the alkyl chain is about 11.5.

Optionally renewable $C_{10}$-$C_{13}$ alkylbenzenes having a peaked alkyl chain distribution can be sulfonated to provide optionally renewable $C_{10}$-$C_{13}$ alkylphenyl sulfonates that have unexpectedly superior performance properties (e.g., grease removal properties) when used alone or in consumer product cleaning or personal care compositions.

Skewed Alkyl Chain Distribution

In embodiments when the $C_{10}$-$C_{13}$ alkylbenzenes have an alkyl chain distribution that is skewed, the mixture comprises $C_{10}$-$C_{13}$ alkylbenzenes having:
(a) $C_{10}$ and $C_{11}$ alkyl groups to $C_{12}$ and $C_{13}$ alkyl groups; or
(b) $C_{12}$ and $C_{13}$ alkyl groups to $C_{10}$ and $C_{11}$ alkyl groups; or
(c) $C_{10}$ alkyl groups to $C_{11}$, $C_{12}$, and $C_{13}$ alkyl groups; or
(d) $C_{13}$ alkyl groups to $C_{10}$, $C_{11}$, and $C_{12}$ alkyl groups
in a weight ratio of at least about 60 to about 40, preferably at least about 80 to about 20, more preferably at least about 90 to about 10, for example at least about 99 to about 1.

Optionally renewable $C_{10}$-$C_{13}$ alkylbenzenes having a skewed alkyl chain distribution can be sulfonated to provide optionally renewable $C_{10}$-$C_{13}$ alkylphenyl sulfonates that have unexpectedly superior performance properties, such as sudsing in hand wash applications, when used alone or in consumer product cleaning and personal care compositions.

Random Alkyl Chain Distribution

In some embodiments, the mixtures of optionally renewable $C_{10}$-$C_{13}$ alkylbenzenes have a random alkyl chain distribution. These mixtures are advantageous because they can be used as a direct replacement for, or in combination with, traditional, petroleum-based alkylbenzenes without altering existing supplier processes, existing changing specifications, or reassessing environmental performance. As direct replacements, the optionally renewable $C_{10}$-$C_{13}$ alkylbenzenes will process identically in terms of formulatibility in a detergent matrix, and will not require further optimization in terms of other attributes, such as sudsing and viscosity of the detergent formulation.

Features

The alkyl groups of the $C_{10}$-$C_{13}$ alkylbenzenes can be linear or branched. In some embodiments when the mixture comprises $C_{10}$-$C_{13}$ alkylbenzenes with both linear and branched alkyl groups, the $C_{10}$-$C_{13}$ alkylbenzenes with linear alkyl groups can be present in an amount of at least about 40 wt. %, at least about 50 wt. %, at least about 60 wt. %, at least about 70 wt. %, at least about 80 wt. %, at least about 90 wt. %, or about 100 wt. %, based on the total weight of the mixture. In some embodiments, the mixture of $C_{10}$-$C_{13}$ alkylbenzenes comprises at least about 40 wt. %, at least about 50 wt. %, at least about 60 wt. %, at least about 70 wt. %, at least about 80 wt. %, at least about 90 wt. %, or about 100 wt. % of $C_{10}$-$C_{13}$ alkylbenzenes with branched alkyl groups, based on the total weight of the mixture.

Nonlimiting examples of the $C_{10}$-$C_{13}$ alkylbenzenes include linear $C_{10}$-$C_{13}$ alkylbenzenes, as shown below.

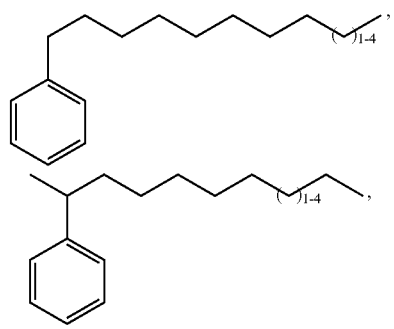

Other nonlimiting examples of $C_{10}$-$C_{13}$ alkylbenzenes (linear and branched) are listed in the below table.
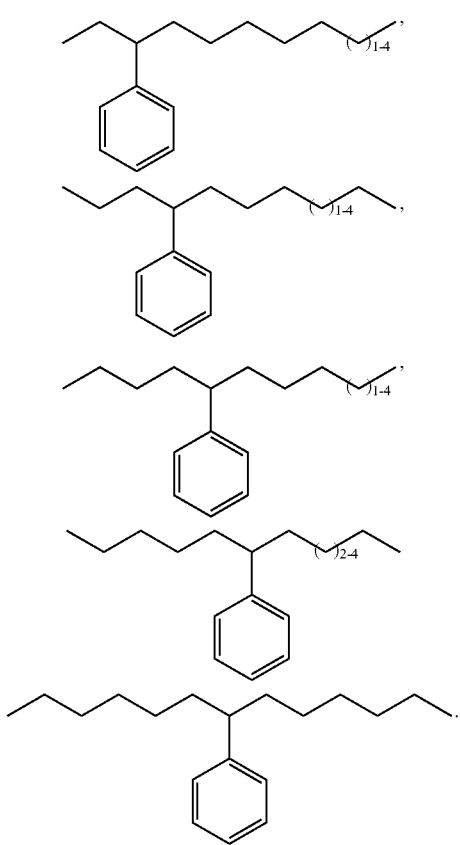

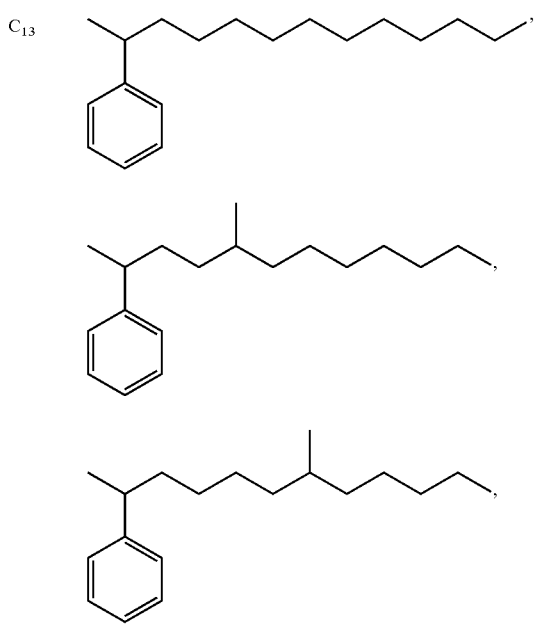

The mixtures of optionally renewable $C_{10}$-$C_{13}$ alkylbenzenes having a controlled alkyl chain distribution can be sulfonated to produce mixtures of optionally renewable $C_{10}$-$C_{13}$ alkylphenyl sulfonates. The mixtures of optionally renewable $C_{10}$-$C_{13}$ alkylbenzenes of the invention are also useful in cleaning compositions and as oil drilling fluids, lubricants, and alternative fuel compositions.

Mixtures of Optionally Renewable $C_{10}$-$C_{13}$ Alkylphenyl Sulfonates

In another aspect, the invention relates to a mixture of $C_{10}$-$C_{13}$ alkylphenyl sulfonates. The alkyl groups on the alkylphenyl sulfonates each independently have a total of 10, 11, 12, or 13 carbon atoms, and can optionally include up to 3 (e.g., 0, 1, 2, or 3) methyl branches, ethyl branches, or a mixture of methyl and ethyl branches. The alkyl groups on the alkylphenyl sulfonates optionally have a biobased content of at least about 5%, at least about 10%, at least about 20%, at least about 30%, at least about 40%, at least about 50%, at least about 60%, at least about 70%, at least about 80%, at least about 90%, at least about 95%, for example about 100%. The phenyl moieties of the $C_{10}$-$C_{13}$ alkylphenyl sulfonates each optionally have a biobased content of at least about 50%, preferably at least about 75%, more preferably at least about 95%, for example about 100%.

The mixture of $C_{10}$-$C_{13}$ alkylphenyl sulfonates comprises less than about 5 wt. %, preferably less than about 3 wt. %, more preferably less than about 1 wt. %, for example about 0 wt. % of alkylphenyl sulfonates with alkyl groups that have 9 or fewer carbon atoms and alkyl groups that have 14 or more carbon atoms, based on the total weight of the mixture. In some embodiments, the mixture of $C_{10}$-$C_{13}$ alkylphenyl sulfonates comprises about 0.1 wt. % to about 5 wt. % of alkylphenyl sulfonates with alkyl groups that have a total of 14 carbon atoms, based on the total weight of the mixture. Alkylphenyl sulfonates having alkyl groups with 9 or fewer carbon atoms and 14 or more carbon atoms are undesirable, as previously described.

Further, the mixture of $C_{10}$-$C_{13}$ alkylphenyl sulfonates comprises less than about 10 wt. %, preferably less than about 7 wt. %, more preferably less than about 5 wt. %, even more preferably less than about 3 wt. %, for example, less than about 1 wt. % of $C_{10}$-$C_{13}$ alkylphenyl sulfonates having two or more $C_{10}$-$C_{13}$ alkyl groups on the phenyl group, based on the total weight of the mixture. Still further, the mixture of $C_{10}$-$C_{13}$ alkylphenyl sulfonates comprises less than about 10 wt. %, preferably less than about 7 wt. %, more preferably less than about 5 wt. %, even more preferably less than about 3 wt. %, for example, less than about 1 wt. % of $C_{10}$-$C_{13}$ alkylphenyl sulfonates having an alkyl group comprising a quaternary carbon atom, based on the total weight of the mixture. The mixture of $C_{10}$-$C_{13}$ alkylphenyl sulfonates can have an alkyl chain distribution that is bimodal, peaked, skewed, random, or flat.

Bimodal Alkyl Chain Distribution

In embodiments when the alkyl chain distribution is bimodal, the mixture comprises $C_{10}$-$C_{13}$ alkylbenzenes having:
(a) $C_{10}$ and $C_{13}$ alkyl groups to $C_{11}$ and $C_{12}$ alkyl groups; or
(b) $C_{10}$, $C_{11}$, and $C_{13}$ alkyl groups to $C_{12}$ alkyl groups; or
(c) $C_{10}$, $C_{12}$, and $C_{13}$ alkyl groups to $C_{11}$ alkyl groups.
in a weight ratio of at least about 60 to about 40, preferably at least about 80 to about 20, more preferably at least about 90 to about 10, for example at least about 99 to about 1. In some specific bimodal alkyl chain distribution embodiments, the average number of carbon atoms of the alkyl chain is about 10.9.

Optionally renewable $C_{10}$-$C_{13}$ alkylphenyl sulfonates having a bimodal alkyl chain distribution provide unexpectedly superior performance properties, such as improved solubility, sudsing performance, grease oil cleaning, and formulability when used alone or in a consumer product cleaning or personal care composition. Data herein shows that mixture of linear $C_{10}$-$C_{13}$ alkylphenyl sulfonates having a bimodal alkyl chain distribution and an average alkyl chain length of 10.9 results in superior properties over a mixture of linear $C_{10}$-$C_{13}$ alkylphenyl sulfonates having an average alkyl chain length of 11.7 and no bimodal distribution. These results were unexpected because it was known to one skilled in the art at the time of the invention that linear alkylphenyl sulfonates with an average alkyl chain length of 11.0 have severely decreased performance when compared to linear alkylphenyl sulfonates with an average chain length of 11.7. Without intending to be bound by any particular theory, one skilled in the art would have reasoned that the less surface active the chain length, the lower the performance. Unexpectedly, the mixture of linear $C_{10}$-$C_{13}$ alkylphenyl sulfonates having a bimodal alkyl chain distribution and an average number of total carbon atoms of 10.9 results in a unique synergy in solution. Without intending to be bound by any particular theory, it is believed that the $C_{10}$ alkylphenyl sulfonate of the novel blend of $C_{10}$, $C_{12}$, and $C_{13}$ alkylphenyl sulfonates provides solubilization in the presence of hard water and rapid kinetics to produce good sudsing, and the $C_{12}$ and $C_{13}$ alkylphenyl sulfonates of this blend provide cleaning power at the soil interface.

Peaked Alkyl Chain Distribution

In embodiments when the alkyl groups of the $C_{10}$-$C_{13}$ alkylphenyl sulfonates have an alkyl chain distribution that is peaked, the mixture comprises $C_{10}$-$C_{13}$ alkylphenyl sulfonates having a weight ratio of at least about 60 to about 40, preferably at least about 80 to about 20, more preferably at least about 90 to about 10, for example at least about 99 to about 1, of $C_{11}$ and $C_{12}$ alkyl groups to $C_{10}$ and $C_{13}$ alkyl groups. In some specific peaked alkyl chain distribution embodiments, the average number of carbon atoms of the alkyl chain is about 11.5.

Optionally renewable $C_{10}$-$C_{13}$ alkylphenyl sulfonates having alkyl chains in a peaked distribution provide unexpectedly superior performance properties, such as improved grease cleaning when used alone or in a consumer product cleaning or personal care composition.

Skewed Alkyl Chain Distribution

In embodiments when the alkyl groups of the $C_{10}$-$C_{13}$ alkylphenyl sulfonates have an alkyl chain distribution that is skewed, the mixture comprises $C_{10}$-$C_{13}$ alkylphenyl sulfonates having:
(a) $C_{10}$ and $C_{11}$ alkyl groups to $C_{12}$ and $C_{13}$ alkyl groups; or
(b) $C_{12}$ and $C_{13}$ alkyl groups to $C_{10}$ and $C_{11}$ alkyl groups; or
(c) $C_{10}$ alkyl groups to $C_{11}$, $C_{12}$, and $C_{13}$ alkyl groups; or
(d) $C_{13}$ alkyl groups to $C_{10}$, $C_{11}$, and $C_{12}$ alkyl groups.
in a weight ratio of at least about 60 to about 40, preferably at least about 80 to about 20, more preferably at least about 90 to about 10, for example at least about 99 to about 1.

Optionally renewable $C_{10}$-$C_{13}$ alkylphenyl sulfonates having a skewed alkyl chain distribution provide unexpectedly superior performance properties, such as improved sudsing and grease cleaning, when used alone or in a consumer product cleaning or personal care composition.

Random Alkyl Chain Distribution

In some embodiments, the mixtures of optionally renewable $C_{10}$-$C_{13}$ alkylphenyl sulfonates have a random alkyl chain distribution. These mixtures are advantageous because they can be used as a direct replacement for, or in combination with, traditional, petroleum-based alkylphenyl sulfonates without altering existing supplier processes, changing existing specifications, or reassessing environmental performance. As direct replacements, the optionally renewable $C_{10}$-$C_{13}$ alkylphenyl sulfonates will process identically in terms of formulatibility in a detergent matrix, and will not require further optimization in terms of other attributes, such as sudsing and viscosity of the detergent formulation.

In some exemplary embodiments, the optionally renewable $C_{10}$-$C_{13}$ alkylphenyl sulfonates have a random alkyl chain distribution with an average total number of carbon atoms in their alkyl chains of 12.2-12.3. Further, these $C_{10}$-$C_{13}$ alkylphenyl sulfonates have less than 5 wt. % of $C_{14}$ alkylphenyl sulfonates, based on the total weight of the mixture. Traditional alkylphenyl sulfonates that have an average total number of carbon atoms of 12.2-12.3 include a much higher weight percentage of $C_{14}$ alkylphenyl sulfonates (e.g., greater than 10 wt. %). The higher the weight percentage of $C_{14}$ alkylphenyl sulfonates, the greater the toxicity of the mixture. Thus, the invention provides for the first time an environmentally improved mixture of optionally renewable alkylphenyl sulfonates having an average total number of carbon atoms in their alkyl chains of 12.2-12.3. Further, the invention provides methods for obtaining this mixture that are not cost prohibitive. A table showing the alkyl chain distributions in commercial alkylphenyl sulfonates having an average number of total carbon atoms of 12.2-12.3 and the mixture of alkylphenyl sulfonates of the invention having an average number of total carbon atoms of 12.2-12.3 is provided below.

Comparison of the Alkyl Chain Distribution in a Commercial Mixture with a Mixture of the Invention Having a Random Distribution.

| Chain Length | Commercial Mixture (wt. %) | Inventive Mixture (wt. %) |
|---|---|---|
| 10 | 9.3 | 0 |
| 11 | 21.0 | 17.1 |
| 12 | 25.6 | 40.3 |

-continued

| Chain Length | Commercial Mixture (wt. %) | Inventive Mixture (wt. %) |
|---|---|---|
| 13 | 30.7 | 42.6 |
| 14 | 13.5 | 0 |

Features

The alkyl groups of the $C_{10}$-$C_{13}$ alkylphenyl sulfonates can be linear or branched, as described for the $C_{10}$-$C_{13}$ alkylbenzenes. Nonlimiting examples of the $C_{10}$-$C_{13}$ alkylphenyl sulfonates include linear $C_{10}$-$C_{13}$ alkylphenyl sulfonates, where the alkyl chain can be attached to any position on the benzene ring, as shown below, where M is hydrogen or an metal ion, such as an alkali metal (e.g., sodium, lithium, potassium), an alkaline earth metal (e.g., calcium, magnesium), or the like.

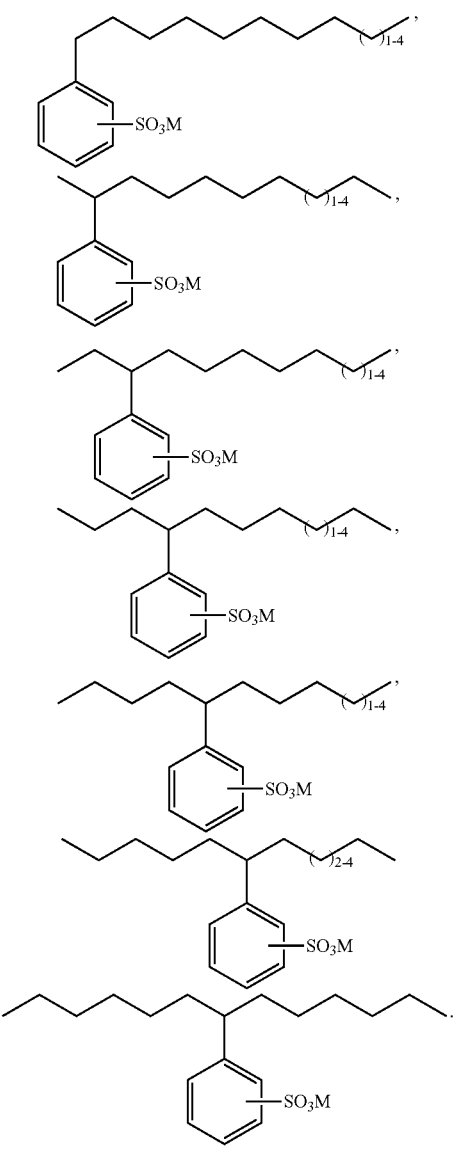

Other nonlimiting examples of $C_{10}$-$C_{13}$ alkylphenyl sulfonates (linear and branched) are listed in the below table.

| Total C # | Structure |
|---|---|
| $C_{10}$ | 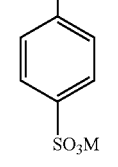 |
| | 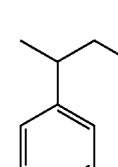 |
| | 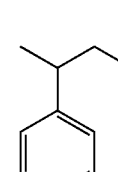 |
| $C_{11}$ | 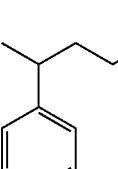 |
| | 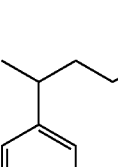 |

| Total C # | Structure |
|---|---|
| | 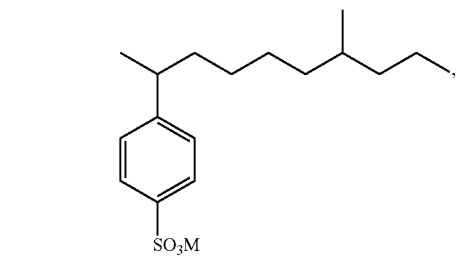 |
| | 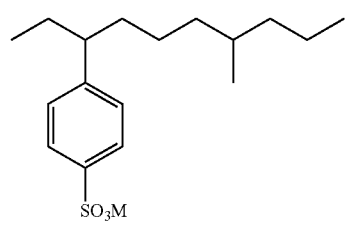 |
| $C_{12}$ | 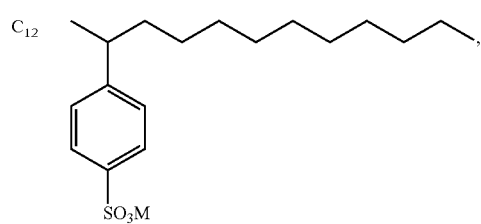 |
| | 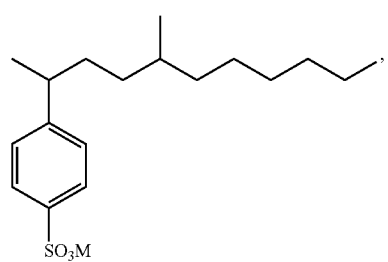 |
| | 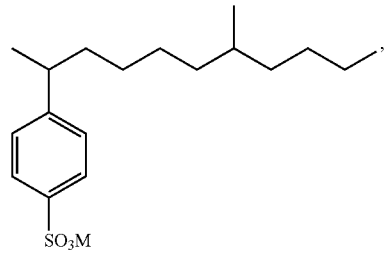 |
| | 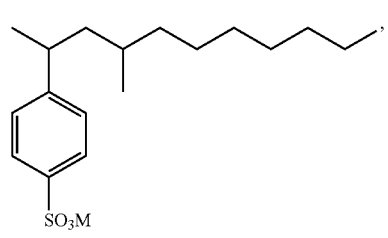 |
| Total C # | Structure |
|---|---|
| | 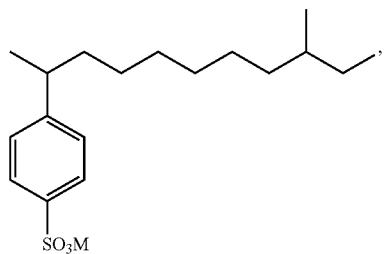 |
| | 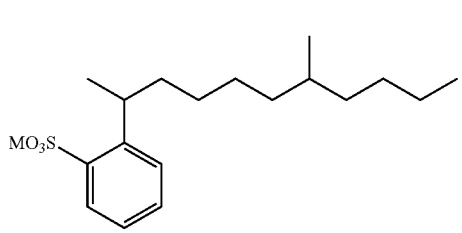 |
| $C_{13}$ | 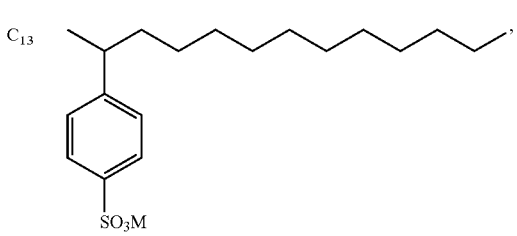 |
| | 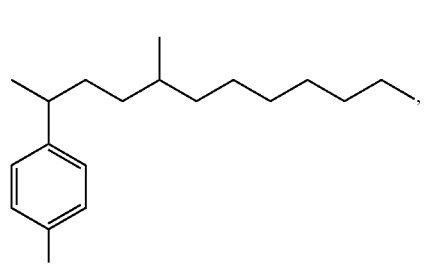 |
| | 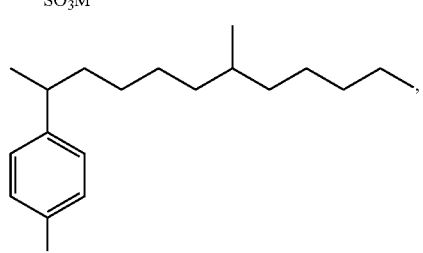 |
| | 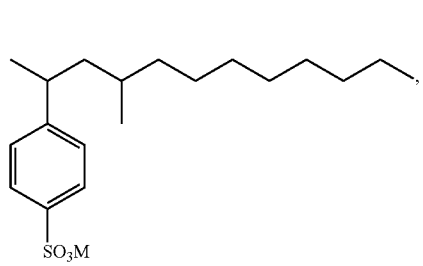 |

-continued

| Total C # | Structure |
|---|---|
| | 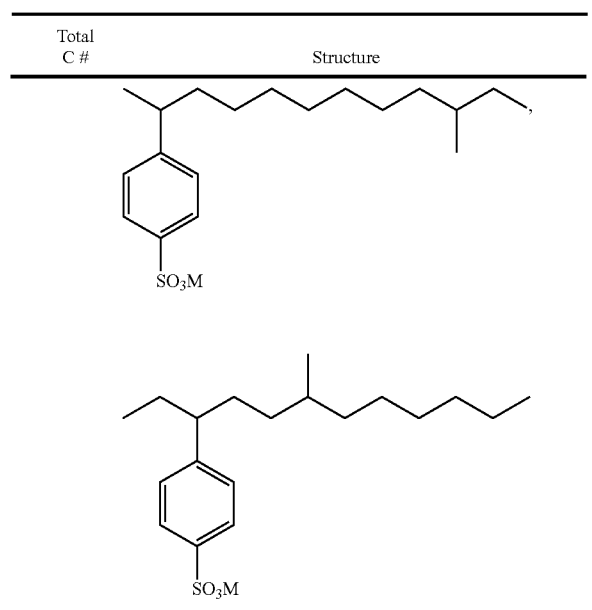 |

The mixtures of $C_{10}$-$C_{13}$ alkylphenyl sulfonates are preferably substantially free (i.e., the amounts of said impurity is insufficient to contribute positively or negatively to the effectiveness of the mixture) from dialkyl tetralin impurities. Typically, the mixture comprises less than about wt. %, preferably less than about 1 wt. %, more preferably less than about 0.1 wt. % of dialkyl tetralin, based on the total weight of the mixture.

Blended Embodiments

The optionally renewable $C_{10}$-$C_{13}$ alkenes, $C_{10}$-$C_{13}$ alkylbenzenes, and $C_{10}$-$C_{13}$ alkylphenyl sulfonates of the invention optionally can be blended with petroleum-based $C_{10}$-$C_{13}$ alkenes, $C_{10}$-$C_{13}$ alkylbenzenes, $C_{10}$-$C_{13}$ alkylphenyl sulfonates, and mixtures thereof. In these blended embodiments, blends can be made at any weight ratio of the optionally renewable to petroleum based compounds, such as, for example, 100:1 to 1:100, 10:90 to 50:50, 51:49 to 92:8.

Further, the particular distributions of optionally renewable $C_{10}$-$C_{13}$ alkenes can be blended with alkenes that have traditional distributions. Likewise, the $C_{10}$-$C_{13}$ alkylbenzenes, and $C_{10}$-$C_{13}$ alkylphenyl sulfonates of the invention can be blended with alkylbenzenes and alkylphenyl sulfonates having traditional alkyl chain distributions to result in compositions having improved performance. For example, a mixture of $C_{10}$-$C_{13}$ alkylphenyl sulfonate of the invention having a peaked alkyl chain distribution can be spiked into a composition comprising alkylphenyl sulfonates with a traditional alkyl chain to result in improved grease cleaning.

Preparation of the Mixtures of Renewable $C_{10}$-$C_{13}$ Alkenes

Alkene Metathesis

Mixtures of renewable $C_{10}$-$C_{13}$ alkenes of the invention having a particular distribution can be prepared using metathesis chemistry. Metathesis involves the reaction of one alkene with another in the presence of a metathesis catalyst to form a new alkene mixture with complete conservation of carbons as illustrated:

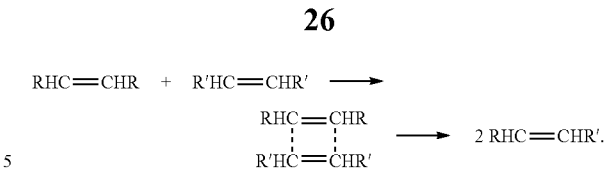

Metathesis chemistry is well known to one skilled in the art (see, e.g., Kirk, "Ruthenium Based Homogeneous Olefin Metathesis," M.S. Dissertation, University of the Free State, South Africa, 2005, Vougioukalakis and Grubbs, Chem. Rev., 110(3):1746-1787 (2010), and U.S. Pat. No. 4,943,397, each incorporated herein by reference).

PCT Application Publication No. WO 2001/02324, incorporated herein by reference, discloses a high temperature (e.g., 300-600° C., 1-30 bar or higher) process for the metathesis of Fischer-Tropsch $C_5$-$C_{15}$ alkenes (i.e., SASOL process) using a tungsten or molybdenum catalyst (e.g., WO3 or MoO$_3$), supported (e.g., by SiO$_2$, Al$_2$O$_3$, ZrO$_2$, TiO$_2$, or mixtures thereof) or unsupported, and with or without co-catalysts, to produce $C_9$-$C_{18}$ linear and mono-methyl branched alkenes. A method for converting short chain alkenes (e.g., $C_4$-$C_{10}$ alkenes) from Fischer-Tropsch derived feedstock to longer chain alkenes (e.g., $C_6$-$C_{18}$) using a heterogeneous metal-alkyliene catalyst, such as tungsten, ruthenium (e.g., Grubb's catalyst), osmium, and iridium is disclosed in PCT Application Publication No. WO 2001/046096 and U.S. Patent Application Publication No. 2003/0135080, each incorporated herein by reference. U.S. Pat. No. 5,942,653 discloses the metathesis of alkenes in the presence of a catalyst system comprising silica, alumina, and an alkyl tin compound, but no transition metal. Further descriptions of alkene metatheses using linear or branched alkene starting materials and a tungsten catalyst on a support (e.g., aluminum oxide) can be found in U.S. Patent Application Publication No. 2008/0255328, and U.S. Pat. No. 7,635,794, each incorporated herein by reference.

Metathesis chemistry using fats and/or oils as starting materials is also known in the art. U.S. Pat. No. 4,545,941 and U.S. Patent Application Publication No. 2010/0160506, which are each incorporated herein by reference, disclose the metathesis of unsaturated triglycerides and alkenes, in the presence of a catalytically effective amount of a metathesis catalyst, to produce modified triglycerides and α-alkenes. U.S. Patent Application Publication No. 2010/0191008, incorporated herein by reference, discloses the metathesis of fatty acid esters of oils (e.g., oleic acid, linoleic acid, linolenic acid, vegetable oil, tung oil, meadowfoam oil, coriander oil, camelina oil, jatropha oil, crambe oil, high erucic rapeseed oil, algal oil) and suitable alkenes. U.S. Patent Application Publication No. 2006/0079704, incorporated herein by reference, discloses the metathesis of ethylene with unsaturated fats and oils (e.g., oleic sunflower oils, oleic rapeseed oils, and monoalcohol esters thereof) in the presence of a ruthenium metathesis catalyst and at least one non-aqueous ionic liquid.

Ngo et al., JAOCS 83(7):629-634 (2006), incorporated herein by reference, describes the solvent-free, self-metathesis of monounsaturated fatty acids of varying purity using the second-generation Grubbs catalyst to form monounsaturated dicarboxylic acids and hydrocarbons in high molecular conversions. Marvey et al., "Ruthenium Carbene Mediated Metathesis of Oleate-Type Fatty Compounds," Int. J. Mol. Sci. 9, 615-625 (2008), incorporated herein by reference, discloses the self-metathesis of unsaturated fatty acids and esters, and cross-metathesis of the fatty acids and esters with ethylene using Grubb's catalysts (e.g., RuCl$_2$(PCy$_3$)$_2$(=CHPh), RuCl$_2$(PCy$_3$)(H$_2$IMes)(=CHPh)), SASOL's phoban-indenylidene ruthenium catalyst [(PhobCy)$_2$Cl$_2$Ru=C$_{15}$H$_{10}$], and Hoveyda-Grubbs catalysts. Further, the metathesis of C$_2$-C$_{10}$ alkenes with natural feedstocks, such as natural oils (e.g., vegetable oils, fish oil, animal fat) and derivatives of natural oils, such as fatty acids and fatty acid alkyl esters is described in PCT Application Publication No. WO 2010/062958, incorporated herein by reference. U.S. Patent Application No. 2010/0145086, incorporated herein by reference, discloses the metathesis of internal alkenes with α-alkenes to form terminal alkenes using a ruthenium catalyst. The internal alkene can include seed oils (e.g., soybean oil, sunflower oil, canola oil, safflower oil, cottonseed oil, castor oil, rapeseed oil, peanut oil, corn oil, olive oil, palm oil, sesame oil, grape seed oil), or compounds that are derived from seed oils. The α-alkene can include 1-propene, 1-butene, 1-pentene, 1-hexene, 1-heptene, 1-octene, and higher alkenes. PCT Patent Application No. WO 2008/046106, incorporated herein by reference, discloses the metathesis of terminal alkenes with fats and oils (e.g., soybean oil, sunflower oil, canola oil, safflower oil, cottonseed oil, castor oil, rapeseed oil, peanut oil, corn oil, olive oil, palm oil, sesame oil, grape seed oil) to form linear metathesis products using a ruthenium alkylidene catalyst. PCT Patent Application No. WO 2009/020667, incorporated herein by reference, discloses a method for improving catalyst efficiency by chemically treating a natural feedstock before introducing the metathesis catalyst to reduce the amount of catalyst poison.

In yet another aspect, the invention relates to a method of making a mixture of partially or wholly renewable C$_{10}$-C$_{13}$ alkenes, as described in the section "Mixtures of Optionally Renewable C$_{10}$-C$_{13}$ Alkenes" using metathesis chemistry. The mixtures of C$_{10}$-C$_{13}$ alkenes have a controlled total carbon atom distribution and a biobased content of at least about 20%, at least about 30%, at least about 40%, at least about 50%, at least about 60%, at least about 70%, at least about 80%, at least about 90%, at least about 95%, for example about 100%. This method comprises reacting in the presence of a catalytically effective amount of a metathesis catalyst and under standard metathesis conditions:

(a) a fatty acid, a fatty ester, a fat, an oil, or a mixture thereof; and, (b) an alkene having a total of 2 to 8 carbon atoms.

The fatty acid, fatty ester, fat, and/or oil has an iodine value of at least about 15, preferably at least about 50, more preferably at least about 180. The iodine value, which can be determined using the AOAC Official Method of Analysis (1984), Chapter 28.023, is the mass of iodine in grams that is consumed by 100 grams of a chemical substance (see, e.g., Pocklington, Pure & Appl. Chem. 62(12):2339-2343 (1990), incorporated herein by reference). The higher the iodine number, the greater the unsaturation in the fatty acid, fatty ester, fat and/or oil. If the iodine number is below about 15, then less of the desired C$_{10}$-C$_{13}$ bio-alkene product is produced. Further, the fatty acid, fatty ester, fat, and/or oil comprises at least about 10 wt. %, preferably at least about 20 wt. % of fatty acids, fatty esters, fats, and/oils that have at least 10 carbon atoms, based on the total weight of the fatty acids, fatty esters, fats, and/or oils.

In any of the methods of making the mixture of C$_{10}$-C$_{13}$ alkenes disclosed herein, the mixture can be made in one pot. In these methods, the starting materials are selected to result in alkene products having particular concentrations of particular chain lengths (e.g., bimodal distribution having a average number of total carbon atoms of 10.9). In some embodiments, the mixture of C$_{10}$-C$_{13}$ alkenes disclosed herein is produced by synthesizing separate batches of alkenes having one particular number of total carbon atoms (e.g., a C$_{10}$ batch, a C$_{11}$ batch, a C$_{12}$ batch, and/or a C$_{13}$ batch) using alkene metathesis, and then combining the batches to form a mixture having a particular distribution.

In some optional embodiments, the fatty acid, fatty ester, fat, and/or oil is partially skeletally isomerized before the metathesis reaction. Skeletal isomerization can occur by any method known to one skilled in the art, such as those methods described in U.S. Pat. Nos. 6,831,184; 6,777,582; 6,602,840; 5,510,306; 5,082,956; 6,593,285; and PCT Patent Application Publication No. WO 2000/014038, each incorporated herein by reference. Preferably, the starting material for skeletal isomerization is an α-alkene. The alkene starting material can contain varying amounts of non-monoolefinic material, such as paraffins, as long as such materials do not materially interfere with the isomerization process. If an alkene raw material contains unacceptable impurities, such as materials which cause poisoning or other difficulties with the isomerization catalyst, the alkene can be purified by known techniques, such as distillation. If diene impurities are present in the alkene, they may be removed by UOP's DEFINE™ process.

Suitable constrained isomerization catalysts are known for various purposes and include those selected from the group consisting of zeolites and silicoaluminophosphates, which are also termed "aluminophosphates" having one-dimensional pore structures with a pore size of about 4.2 Angstrom to about 7 Angstrom. Preferred examples of such catalysts include: (i) zeolites having ferrierite isotypic framework structure (more preferably H-ferrierites); and (ii) non-zeolite types such as the silicoaluminophosphates including, but not limited to ALPO-31, SAPO-11, SAPO-31 and SAPO-41. Ferrierite types and SAPO-11 or any suitable isotype are especially preferred. The term "isotype" as used herein refers to a catalyst having substantially equivalent framework structure, particularly with respect to pore dimensions. For example, U.S. Pat. No. 5,510,306 describes an active and stable catalyst for isomerizing linear alkenes to methyl branched isoalkenes. In this process, a zeolite powder containing at least one zeolite is mixed with (i) at least one one-dimensional pore structure having pore size small enough to retard by-product dimerization and coke formation, and large enough to permit entry of the linear alkene and allow formation of the methyl branched isoalkene; (ii) an alumina-containing binder; (iii) water; (iv) at least one acid selected from monocarboxylic acids and inorganic acids and (v) at least one polycarboxylic acid. Pellets of the mixture are formed, which then undergo calcination.

The preferred skeletal isomerization catalysts comprise substantially only zeolites with the specified pore size in one dimension. Specifically, nonlimiting examples of zeolites and aluminophosphates that can be used for skeletal isomerization of the alkenes specified herein are the hydrogen form of ferrierite, AlPO-31, SAPO-11, SAPO-31, SAPO-41, FU-9, NU-10, NU-23, ZSM-12, ZSM-22, ZSM-23, ZSM-35, ZSM-48, ZSM-50, ZSM-57, MeAPO-11, MeAPO-31, MeAPO-41, MeAPSO-11, MeAPSO-31, MeAPSO-41, MeAPSO-46, ELAPO-11, ELAPO-31, ELAPO-41, ELAPSO-11, ELAPSO-31, ELAPSO-41, laumontite, cancrinite, offretite, the hydrogen form of stilbite, the magnesium or calcium form of mordenite and partheite. Many natural zeolites, such as ferrierite, having an initially reduced pore size can be converted to those forms suitable for alkene skeletal isomerization in the instant invention, for example, by removing associated alkali metal or alkaline earth metal by ammonium ion exchange and calcination to produce the substantially hydrogen form as taught in U.S. Pat. No. 4,795,623 and U.S. Pat. No. 4,924,027, each incorporated herein by reference. Note that H-form mordenite is unsuitable for this process step but is useful in the later step of alkylation as taught hereinafter.

Dunning et al., Ind. Eng. Chem., 45(3):551-564 (1953), incorporated herein by reference, describes methods for isomerizing alkenes at temperatures of, e.g., 357° C., and a liquid hourly space velocity (LHSV) of about 137 per catalyst to provide a high yield of internal alkenes, while minimizing branching. Ewell et al., J. Am. Chem. Soc. 63:3460 (1941), incorporated herein by reference, also describes methods for alkene isomerization.

In some embodiments, the short chain alkene is contacted with about 10% to about 20% weight/weight of an acidic Y zeolite. The mixture is placed in a sealed reactor under a blanket of nitrogen and is heated to 120-130° C. for several hours. After cooling, the resulting isomerized alkene is removed by distillation at atmospheric pressure. The resulting alkene mixtures contain both terminal and internal alkenes, which are useful for metathesis with, e.g., unsaturated esters. For example, when 1-butene, 1-pentene, or 1-hexene are subjected to this process, a mixture of 1- and 2-butene, 1- and 2-pentene, or 1-, 2-, and 3-hexene results.

The fatty acid, fatty acid ester, fat (e.g., animal fat), or oil (e.g., terpenes, monoglycerides, diglycerides, triglycerides, and mixtures thereof) can be derived from renewable resources, such as animals or plants. "Fatty acid" refers to a straight chain monocarboxylic acid having a chain length of 8 to 22 carbon atoms, preferably, 12 to 22 carbon atoms, more preferably 16 to 18 carbon atoms.

"Monoglycerides," "diglycerides," and "triglycerides" refer to mono-, di- and tri-esters, respectively, of (i) glycerol and (ii) the same or mixed fatty acids. Nonlimiting examples of fatty acids include oleic acid, myristoleic acid, palmitoleic acid, sapienic acid, linoleic acid, linolenic acid, arachidonic acid, eicosapentaenoic acid, and docosahexaenoic acid. Nonlimiting examples of monoglycerides include monoglycerides of any of the fatty acids described herein. Nonlimiting examples of diglycerides include diglycerides of any of the fatty acids described herein. Nonlimiting examples of the triglycerides include triglycerides of any of the fatty acids described herein, such as, for example, tall oil, corn oil, soybean oil, sunflower oil, safflower oil, linseed oil, perilla oil, cotton seed oil, tung oil, peanut oil, oiticica oil, hempseed oil, marine oil (e.g., alkali-refined fish oil), dehydrated castor oil, and mixtures thereof.

Preferably, the fatty acid, fatty ester, fat, or oil is selected from or derived from the group consisting of palm oil, kernel oil, coconut oil, rapeseed oil, canola oil, soybean oil, algae oil, cottonseed oil, Jatropha oil, babasu oil, fish oil, linseed oil, tall oil, tallow, poultry fat, camolina, *cuphea*, a microorganism (e.g., bacteria, yeast, and a mixture thereof), and mixtures thereof. Even more preferably the fatty acid, fatty ester, fat, or oil is selected from or derived from the group consisting of palm oil, rapeseed oil, canola oil, soybean oil, cottonseed oil, jatropha oil, babasu oil, tallow, poultry fat, *cuphea*, and mixtures thereof. In some embodiments, the fatty acid, fatty ester, fat, or oil is obtained from plants with very high levels of monounsaturated fatty acid, such as from DuPont's PLENISH™ or Monsanto's VISTAGOLD™ high oleic soybean, or the USDA's HA458, HA459 and HA460 high oleic sunflower.

The fatty acids, fatty esters, fats, and oils of the invention can be obtained from their natural sources, as previously described. In some embodiments, the fatty acid, fatty ester, fat, or oil of the invention having a particular chain length also can be produced using engineered oil seed plants. For example, the mid-chain fatty acyl-ACP thioesterase genes, such as from several species in the genus *Cuphea* including *procumbens, lutea, hookeriana, hyssopifolia, wrightii* and *inflate*, the Lauraceae family, e.g., the California Bay (*Umbellularia californica*), Pisa (*Actinodophne hookeri*), Sweet Bay (*Laurus nobilis*) and *Cinnamomum camphora* (camphor), and other plant sources, such as Ulmaceae (elm), Myristicaceae, Simarubaceae, Vochysiaceae, and Salvadoraceae can be expressed in oil seed plants, such as Canola, which then accumulate medium chain (e.g., $C_{12}$, $C_{14}$) fatty acid containing lipids (see, e.g, U.S. Pat. Nos. 5,298,421; 5,304,481; 5,344,771; 5,512,482; and 5,850,022, each incorporated herein by reference). The fatty acid, fatty ester, fat, or oil of the invention also can be produced by any other method known to one skilled in the art, such as through polyketide synthesis (see e.g., Rawlings, Nat. Prod. Rep. 16:425-484 (1999) and Hranueli et al., Food Technol. Biotechnol 39(3): 203-213 (2001), each incorporated herein by reference).

In some embodiments, the fatty acids, fatty esters, fats, and oils of the invention have been modified from a natural form into an unnatural form (e.g., skeletally isomerized, double-bond isomerized, and/or partially hydrogenated to remove di- and tri-unsaturation) before being subjected to the metathesis reaction.

The alkene having a total of 2 to 8 carbon atoms can include any alkene having 2 to 8 carbon atoms, such as, for example, ethylene, propylene, 1-butene, 2-butene, 2-methylpropene, 1-pentene, 2-pentene, 2-methyl-1-butene, 2-methyl-2-butene, 3-methyl-1-butene, 1-hexene, 2-hexene, 3-hexene, 2-methyl-1-pentene, 2-methyl-2-pentene, 4-methyl-2-pentene, 4-methyl-1-pentene, 3-methyl-1-pentene, 3-methyl-2-pentene, 2-ethyl-1-butene, 1-heptene, 2-heptene, 3-heptene, 2-methyl-1-hexene, 2-methyl-2-hexene, 2-methyl-3-hexene, 5-methyl-2-hexene, 5-methyl-1-hexene, 3-methyl-1-hexene, 3-methyl-2-hexene, 4-methyl-3-hexene, 4-methyl-2-hexene, 4-methyl-1-hexene, 2-ethyl-1-pentene, 1-octene, 2-octene, 3-octene, 2-methyl-1-heptene, 2-methyl-2-heptene, 2-methyl-3-heptene, 6-methyl-3-heptene, 6-methyl-2-heptene, 6-methyl-1-heptene, 3-methyl-1-heptene, 3-methyl-2-heptene, 3-methyl-3-heptene, 5-methyl-3-heptene, 5-methyl-2-heptene, 5-methyl-1-heptene, 4-methyl-1-heptene, 4-methyl-2-heptene, 4-methyl-3-heptene, 2-propyl-1-pentene and mixtures thereof. Preferably the alkene having a total of 2 to 8 carbon atoms is selected from the group consisting of ethylene, propylene, a linear butene, a linear pentene, a linear hexene, a linear heptene, a linear octene, and mixtures thereof. More preferably the alkene having a total of 2 to 8 carbon atoms is selected from the group consisting of ethylene, propylene, 1-butene, 2-butene, 1-pentene, 2-pentene, 3-hexene, 3-heptene, and mixtures thereof. In some optional embodiments, the alkene having a total of 2 to 8 carbon is 1-pentene and 2-pentene. In some embodiments the $C_2$-$C_8$ alkene is wholly or partially derived from a renewable resource. In alternative embodiments, the $C_2$-$C_8$ alkene is not derived from renewable resource (e.g., is petroleum-based).

The mixture of $C_{10}$-$C_{13}$ alkenes that results from the metathesis reaction is as previously described in the section "Mixtures of Optionally Renewable $C_{10}$-$C_{13}$ Alkenes." The mixture of $C_{10}$-$C_{13}$ alkenes produced from alkene metathesis comprises alkenes that have a biobased content of at least about 20%, at least about 30%, at least about 40%, at least about 50%, at least about 60%, at least about 70%, at least about 80%, at least about 90%, at least about 95%, for example about 100%. The alkenes each independently have a total of 10 to 13 carbon atoms and can optionally include up to 3 methyl branches, ethyl branches, or a mixture of methyl and ethyl branches. The mixture comprises less than about 5 wt. %, preferably less than about 3 wt. %, more preferably less than about 1 wt. %, for example about 0 wt. % of alkenes that have 9 or fewer carbon atoms and alkenes that have 14 or more carbon atoms, based on the total weight of the mixture. In some embodiments, the mixture of $C_{10}$-$C_{13}$ alkenes comprises about 0.1 wt. % to about 5 wt. % of alkenes that have a total of 14 carbon atoms. Further, the mixture of $C_{10}$-$C_{13}$ alkenes optionally comprises alkanes in an amount less than about 50 wt. %, preferably less than about 25 wt. %, more preferably less than about 5 wt. %, for example, less than about 1 wt. %. Further still, the mixture of $C_{10}$-$C_{13}$ alkenes optionally comprises less than about 10 wt. %, preferably less than about 5 wt. %, more preferably less than about 1 wt. % of oxygen-containing compounds (e.g., fatty esters, glycerin). The $C_{10}$-$C_{13}$ alkenes in the mixture have a total carbon atom distribution that is bimodal, peaked, skewed, random, or flat, as previously described. The mixture can comprise linear alkenes, branched alkenes, or both linear and branched alkenes, as previously described.

In some embodiments, the mixture of $C_{10}$-$C_{13}$ alkenes produced from alkene metathesis is substantially monounsaturated. In some optional embodiments, the mixture of $C_{10}$-$C_{13}$ alkenes is partially hydrogenated to form a mixture of substantially monounsaturated $C_{10}$-$C_{13}$ alkenes. Partial hydrogenation can occur by any method known to one skilled in the art. U.S. Pat. No. 6,627,778, incorporated herein by reference, describes catalysts and reaction conditions that can be used to convert tri-alkenes and di-alkenes into mono-alkenes. This method also can be applied to polyunsaturated fatty acids, fatty esters, fat and oil starting materials to form mono-saturated compounds. For example, the mixture of $C_{10}$-$C_{13}$ alkenes can be treated with hydrogen and a catalyst, such as a platinum, palladium, rhodium, ruthenium, or nickel (e.g., Raney nickel, Urushibara nickel) catalyst. Other suitable catalysts for partial hydrogenation are described in U.S. Pat. Nos. 4,695,560; 4,523,048; 4,520,214; and 4,761,509 and Chinese Patent No. CN 1032157, each incorporated herein by reference.

In some embodiments, the partial hydrogenation catalyst can contain about 1.0 wt. % to about 25 wt. % of nickel, about 0.05 wt. % to about 1.5 wt % of sulfur with a support comprising small $Al_2O_3$ balls made by the oil-drop method. These balls have a pore volume of about 1.44 to about 3.0 cm$^3$/g, a surface area larger than 150 m$^2$/g, have no precious metals, and essentially no halogens, alkali earth metals and alkali metals (e.g., less than about 0.1 wt %). Because the main active element of the catalyst used in this process is nickel, selective hydrogenation is conducted at a temperature greater than about 200° C. Further, the catalyst can be sulfurized to suppress its activity to increase the selectivity of tri-alkenes and di-alkenes, to mono-alkenes.

The step of partial hydrogenation can reduce the amount of dialkenes that are optionally present in the mixture to avoid the formation of tetralins during benzene alkylation, which are not biodegradable.

In some optional embodiments, the mixture of $C_{10}$-$C_{13}$ alkenes or substantially monounsaturated $C_{10}$-$C_{13}$ alkenes is isolated from a crude reaction mixture. Isolation can occur by any method known to one skilled in the art, such as fractional distillation, and simple distillation. Preferably, the mixture of $C_{10}$-$C_{13}$ alkenes or substantially monounsaturated $C_{10}$-$C_{13}$ alkenes is isolated by simple distillation. In some embodiments, the isolated mixture of $C_{10}$-$C_{13}$ alkenes has a purity of at least about 80%, preferably at least about 90%, more preferably at least about 95%, as determined by gas chromatography (GC).

The catalyst used in the metathesis reaction can be any metathesis catalyst or catalyst system useful to catalyze the metathesis reaction of the invention to the desired extent. Any known or future metathesis catalyst can be employed alone, or in combination, with one or more additional catalysts. In some embodiments, the catalyst is quenched and distilled before use. Quenching can be carried out by methyl vinyl ether or removal of the catalyst by absorption onto, e.g., clays. Examples of suitable metathesis catalysts include metal carbene catalysts based on transition metals, such as, for example, ruthenium, chromium, rhenium, tungsten/tin, molybdenum, osmium, titanium, and mixtures thereof. Preferred metathesis catalysts can be based on transition metals selected from the group consisting of a ruthenium catalyst, a molybdenum catalyst, a tungsten/tin catalyst, a rhenium catalyst, a titanium catalyst, and mixtures thereof.

Nonlimiting, specific examples of catalysts appropriate for the production of the mixtures of renewable $C_{10}$-$C_{13}$ α-alkenes of the invention include the Tebbe complex, a tungsten dicarbonyl complex (e.g., $W(CO)_5CPhOCH_3$, $W(CO)_5CPh_2$) Grubbs first generation catalyst [$Ru(Cl)_2(PCy_3)_2CHPh$], Grubbs second generation catalyst [$Ru(Cl)_2(PCy_3)_2(NHC)$ CHPh], where NHC is a bulky N-heterocyclic carbene ligand $H_2IMes$, a Schrock carbene complex (e.g., Ta=CH-t-Bu $(CH_2\text{-t-Bu})_3$, [$W(O)(=CH\text{-t-Bu})(PEt_3)_2Cl_2$]), or any of the catalysts described in Vougioukalakis and Grubbs, Chem. Rev., 110(3):1746-1787 (2010), and U.S. Patent Application Nos. 2009/0217568 and 2010/0145086, each incorporated herein by reference. Other examples of suitable catalysts include SASOL's Ru-alkylidene catalyst that contains a phosphorus containing ligand, such as phosphabicylononane, as described in U.S. Pat. No. 7,671,224, U.S. Patent Application Publication No. 2008/0221345, and PCT Patent Application Publication No. 2007/010453, each incorporated herein by reference, examples of which are shown below.

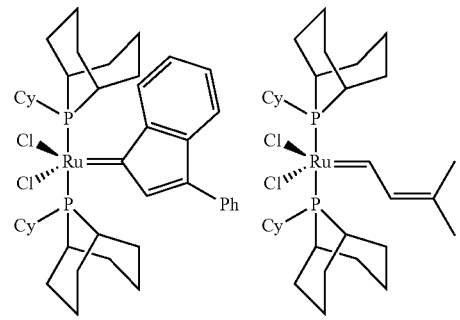

Hoveyda-Grubbs catalysts are also suitable catalysts for the invention, as described in Marvey et al., "Ruthenium Carbene Mediated Metathesis of Oleate-Type Fatty Compounds," Int. J. Mol. Sci. 9, 615-625 (2008), and WO 2010/062958, each incorporated herein by reference. An example of a Hoveyda-Grubbs catalyst is shown below.

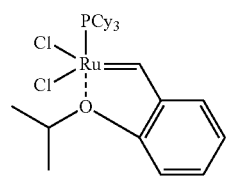

Polymer-bound catalysts, examples of which are described in Buchmeiser, "Polymer-Supported Well-Defined Metathesis Catalysts," Chem. Rev., 109, 303-321, 2009, incorporated herein by reference, also can be used for the metathesis reaction of the invention.

In some embodiments, the metathesis reaction is carried out in the presence of a phenolic compound (e.g., phenol, substituted phenol), as described in U.S. Patent Application Publication No. 2006/0211905, which is incorporated herein by reference. The phenolic compound enhances the turnover of the catalyst, which slows down deactivation of the catalyst.

Metathesis Reaction Conditions

The metathesis reaction can be carried out neat or in an organic solvent. The presence of a solvent improves mixing and, if added to the fatty acid, fatty ester, fat, and/or oil and partially distilled off before reaction, helps remove traces of water which can poison some metathesis catalysts (e.g., tungsten hexachloride). The more commonly used solvents in metathesis reactions include aliphatic solvents (e.g., saturated hydrocarbons) and aromatic solvents (e.g., benzene, chlorobenzene, and toluene). The aliphatic solvents are preferred over the aromatic solvents because of a reduced tendency to interact with the reactants. In some preferred embodiments, the solvent is a saturated hydrocarbon that boils in the range of about 50° C. to about 120° C. (e.g., commercial hexane).

In some embodiments, the metathesis reaction is carried out at a temperature of about 35° C. to about 260° C., preferably about 50° C. to about 120° C. The reaction does not proceed to a noticeable degree at temperatures below about 35° C. The rate of the reaction increases with increasing temperature. Temperatures above about 260° C., however, are undesirable because the starting materials begin to degrade.

Sources of Renewable Alkenes for the Metathesis Reaction of the Invention

The renewable alkenes of the invention can be produced from any renewable source, such as the decarboxylation of natural fats and oils under low or no hydrogen conditions (e.g., $C_8$-$C_{22}$ fatty acids, monoglycerides and diglycerides of $C_8$-$C_{22}$ fatty acids, $C_1$-$C_4$ alkyl esters of $C_8$-$C_{22}$ fatty acids) using an activated acidic catalyst free of Group VIII metals (e.g., Sn/Pt), as described in PCT Patent Application No. WO 2007/136873, incorporated herein by reference. For example, alkenes produced from seed oil derived soy fatty acid methyl esters using 1-propene or 1-butene would result in 9.8% of 1-decene, 5.4% of 2-undecene, 17.5% of methyl 9-decenoate, and 13.9% of methyl 9-undecenoate, or 10.5% of 1-decene, 8.2% of 3-dodecene, 19.6% of methyl 9-decenoate, and 14.6% of methyl 9-dodecenoate, as described in PCT Application Publication No 2008/046106. PCT Application No. WO 2008/046106, incorporated herein by reference, also describes the metathesis of 1-butene with soy oil derived fatty acid methyl esters.

Short chain renewable $C_2$-$C_4$ alkenes can be used as co-reactants in the metathesis reactions to provide longer chain alkene products that are 100% biobased. These bio-short chain alkenes can be produced from plant biomass, as described in Paushkin, et al., Chemistry and Technology of Fuels and Oils 30(4-5):249-252 (1994) and Khokhlachev et al., Khimiya i Tekhnologiaya Topliv i Masel 6:3-5 (1994), each incorporated herein by reference. In this process, plant raw material undergoes steam gasification at 1000-1200° C., as shown in the below scheme. The products of gasification containing carbon monoxide and hydrogen are then reacted with a Co catalyst (200° C., 1 MPa) to form liquid hydrocarbons. These liquid hydrocarbons are purified and subjected to pyrolysis over a $KVO_4$ catalyst at 790° C. to form the $C_2$-$C_4$ alkenes.

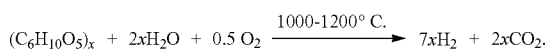

Renewable $C_2$-$C_8$ alkenes also can be produced using the SASOL process. In this process, renewable 1-butene is isomerized in situ to 2-butene, which undergoes metathesis with the remaining 1-butene to produce propene and 2-pentene. Self-metathesis of the 1-butene produces 3-hexene and ethene. The ethene can undergo metathesis with the 2-butene and 2-pentene to form additional propene.

Another source of renewable $C_4$-$C_8$ alkenes is lignocellulosic wastes. Alkenes can be produced from this waste by subjecting the waste to acid hydrolysis to form levulinic acid. The levulinic acid is then catalytically upgraded to 5-nonane with the intermediate formation of γ-valerolactone (GVL) (Bond et al., Science 327:110-114 (2010) and Bond et al., Langmuir 26(21):16291-16298 (2010), each incorporated herein by reference). Specifically, the GVL is produced by the hydrogenation of levulinic acid. GVL can be processed with a combined decarboxylation and oligomerization strategy to form alkenes. In this process, GVL undergoes a ring opening to produce an isomeric mixture of unsaturated pentenoic acids, which then undergo decarboxylation to produce butane isomers and a stoichiometric quantity of carbon dioxide. This reaction can be carried out over a solid acid catalyst, $SiO_2/Al_2O_3$, in the presence of water and at a pressure of ambient up to 36 bar. A separation step occurs where water is condensed to the liquid state and the butane undergoes acid-catalyzed oligomerization to higher molecular weight alkenes. This oligomerization process is favored at elevated pressures and can be tuned to yield alkenes with a targeted range of molecular weights and varied degrees of branching.

The GVL process for the preparation of alkenes is advantageous because it provides a mixture of alkenes that is not random. In addition, it produces a carbon dioxide stream at elevated pressure (e.g., 36 bar), which is appropriate for sequestration, conversion to methanol upon reaction with a renewable source of hydrogen, or copolymerization with epoxides to yield polycarbonates. By contrast, the production of carbon dioxide during fermentation of glucose to ethanol is carried out at atmospheric pressure in the presence of air.

Renewable $C_2$-$C_8$ alkenes also can be produced from sugars. For example, bio-ethylene and bio-propylene can be formed from the dehydration of bio-ethanol and bio-propanol, respectively. Bio-ethanol and bio-propanol can be derived from, for example, (i) the fermentation of sugar from sugar cane, sugar beet, or sorghum; (ii) the saccharification of starch from maize, wheat, or manioc; and (iii) the hydrolysis of cellulosic materials. U.S. Patent Application Publication No. 2005/0272134, incorporated herein by reference, describes the fermentation of sugars to form alcohols and acids.

Suitable sugars used to form ethanol and propanol include monosaccharides, disaccharides, trisaccharides, and oligosaccharides. Sugars, such as sucrose, glucose, fructose, and maltose, are readily produced from renewable resources, such as sugar cane and sugar beets. Sugars also can be derived (e.g., via enzymatic cleavage) from other agricultural products (i.e., renewable resources resulting from the cultivation of land or the husbandry of animals). For example, glucose can be prepared on a commercial scale by enzymatic hydrolysis of corn starch. Other common agricultural crops that can be used as the base starch for conversion into glucose include wheat, buckwheat, arracaha, potato, barley, kudzu, cassava, sorghum, sweet potato, yam, arrowroot, sago, and other like starchy fruit, seeds, or tubers. The sugars produced by these renewable resources (e.g., corn starch from corn) can be used to produce alcohols, such as propanol, ethanol, and methanol. For example, corn starch can be enzymatically hydrolyzed to yield glucose and/or other sugars. The resultant sugars can be converted into ethanol and propanol by fermentation.

Bio-propanol also can be derived from bio-ethylene. In this pathway, bio-ethylene is converted into propionaldehyde by hydroformylation using carbon monoxide and hydrogen in the presence of a catalyst, such as cobalt octacarbonyl or a rhodium complex. Hydrogenation of the propionaldehyde in the presence of a catalyst, such as sodium borohydride and lithium aluminum hydride, yields propan-1-ol, which can be dehydrated in an acid catalyzed reaction to yield propylene, as described in U.S. Patent Application Publication No. 2007/0219521, incorporated herein by reference.

In some embodiments, bio-ethanol dehydrated to ethylene can then be oligomerized via the Shell Higher Olefin Process (SHOP®, Shell Chemicals), as described in Scheibel, Journal of Surfactants and Detergents, "The Evolution of Anionic Surfactant Technology to Meet the Requirements of the Laundry Detergent Industry", 7(4):319-328 (2004), incorporated herein by reference, to form alpha bio-alkenes with an even chain length. These alpha bio-alkenes can be further processed in the internal olefin unit to form both even and odd internal alkenes. These types of bio-alkenes can then be metathesized to produced mixed bio-internal alkenes with even and odd chains.

Bio-ethylene and bio-propylene also can be produced from biomass waste (e.g., wood, agricultural waste, municipal waste) using the methanol-to-oil (MTO) process, as described in a PowerPoint presentation, "Biomass Waste to Olefin Technology," MIT (2005) by Chiang, incorporated herein by reference. In the pretreatment step of this process, the biomass waste is chipped or grinded to a proper size and dried. The resulting product is subjected to steam, oxygen, and heat in a gasification step, to result in hydrogen, water, carbon monoxide, carbon dioxide, methane, ethane, and other by-products, which are subsequently removed. The methane and ethane are converted to carbon monoxide and hydrogen using a nickel-based catalyst. The amount of carbon monoxide is adjusted using the water-gas shift reaction ($H_2O + CO \rightarrow CO_2 + H_2O$), and the amount of carbon dioxide is adjusted using chemical absorption to result in a $H_2$:CO ratio of 2:1, with relatively small amounts of carbon dioxide. The hydrogen then reacts with carbon monoxide and carbon dioxide to form methanol. The methanol is fed into a reactor, a catalyst is added, product gas (e.g., methane, ethane, propane, carbon dioxide, water) is cooled and some water is condensed. The carbon dioxide is removed, as well as the remaining water. Ethylene and propylene are recovered. Three tones of methanol is required to produce each tonne of ethylene/propylene. The process can yield 0.8 to 1.3 tonnes of propylene per ton of ethylene.

Other sources of bio-ethylene are as follows. In higher plants, bio-ethylene can be produced via amino-cyclopropane-1-carboxylic acid (ACC) according to the ACC pathway. In microorganisms, bio-ethylene can be synthesized according to the KMBA pathway. In fungi *Penicillium cyclopium, P. digitatum, F. oxisporum* and in bacteria *P. syringae*, bio-ethylene can be produced using 2-oxoglutaric acid as a precursor and the multifunction enzyme termed "ethylene-forming enzyme" (EFE).

Although less preferred, the alkene starting materials of the invention can be prepared from the partial or complete dehydrogenation of renewable paraffin feedstock using any method known to one skilled in the art. In general, dehydrogenation of the paraffin can be accomplished using any of the well-known dehydrogenation catalyst systems or "conventional dehydrogenation catalysts" including those described in the Surfactant Science Series references previously cited as well as in "Detergent Manufacture Including Zeolite Builders and Other New Materials", Ed. Sittig, Noyes Data Corp., New Jersey, 1979, incorporated herein by reference, and other dehydrogenation catalyst systems, for example those commercially available though UOP Corp. Dehydrogenation can be conducted in presence of hydrogen gas and, commonly, a precious metal catalyst. Alternatively, non-hydrogen, precious-metal free dehydrogenation systems such as a zeolite/air system can be used. As is well known, dehydrogenation can be complete or partial, more typically partial. When dehydrogenation is partial, a mixture of alkenes and unreacted paraffin results. Such mixture is a suitable feed for the alkylation step of the invention, as long as the mixture includes less than about 50 wt. %, preferably less than about 25 wt. %, more preferably less than about 5 wt. %, for example, less than about 1 wt. % of paraffins.

Similar to the isomerization of alkene starting materials, as previously described, paraffin raw material also can undergo skeletal isomerization before dehydrogenation. The paraffin material can contain varying amounts of other materials, such as isoparaffins or alkenes, as long as such materials do not materially interfere with the isomerization of the paraffins. If paraffin raw materials contain unacceptable impurities, such as materials which cause poisoning or other difficulties with the isomerization catalyst, the linear paraffin can be purified by known techniques, such as distillation or catalytic hydrogenolysis to remove sulfur-containing impurities. In general, any catalyst suitable for alkyl branching, preferably methyl branching, of a linear paraffin is useful in the isomerization process. Preferred isomerization catalysts for this step include (i) zeolites having ferrierite isotypic framework structure (more preferably H-ferrierites); (see, e.g., U.S. Pat. No. 5,510,306, incorporated herein by reference) and (ii) ALPO-31, SAPO-11, SAPO-31 and SAPO-41.

SAPO-11 containing catalyst systems are preferred and can include both Pt-SAPO-11 and Pd-SAPO-11, though the platinum form is preferred. See U.S. Pat. No. 5,246,566 and S. J. Miller, Microporous Materials, Vol. 2 (1994) 439-449, each incorporated herein by reference. The latter reference also provides a comparison with several other useful linear paraffin isomerization catalysts.

Renewable short chain alkenes also can be produced from alkanes that are produced from cellulose, as described in Serrano-Ruiz et al., Applied Catalysis B: Environmental 100 (1-2):184-189 (2010) incorporated herein by reference. In this process, solid cellulose is deconstructed to produce glucose using aqueous sulfuric acid. The glucose is subsequently dehydrated under acidic conditions to generate an equimolar mixture of levulinic acid and formic acid. The formic acid is decomposed to hydrogen and carbon dioxide, and the hydrogen is used to reduce the levulinic acid to GVL over a Ru/C catalyst. The GVL product is more hydrophobic than levulinic acid, thereby enabling selected separation of sulfuric acid from GVL, and allowing most of the acid to be recycled back to the cellulose deconstruction reactor. An aqueous solution of GVL containing smaller amounts of sulfuric acid is then passed over a sulfur-tolerant niobia-supported palladium catalyst in the presence of hydrogen to produce pentanoic acid, followed by conversion to 5-nonanone by ketonization over a ceria-zirconia catalyst. The hydrophobic stream of 5-nonane can be further processed to liquid alkanes with controlled structures by means of well-established hydrogenation, dehydration and/or isomerization reactions. The alkanes can be converted to alkenes by any method known to one skilled in the art.

Another source of alkanes that can be converted to the alkenes of the invention is described in U.S. Patent Application Publication No. 2009/0124839, incorporated herein by reference. In this process, a feedstock solution comprising a carbohydrate is dehydrated in the presence of an acid to yield at least one furan derivative compound. The furan derivative compound is subjected to at least one self-aldol condensation reaction or a crossed-aldol condensation reaction with another carbonyl compound to yield a beta-hydroxy carbonyl compound and/or an alpha-beta unsaturated carbonyl compound. The beta-hydroxy carbonyl and/or alpha-beta unsaturated compounds are then hydrogenated to yield a saturated or partially saturated compound, which undergoes hydrodeoxygenation (e.g., dehydration and hydrogenation) to yield a composition comprising $C_8$-$C_{15}$ alkanes.

Other renewable sources for the production of alkanes are disclosed in Lennen et al., Biotechnology and Bioengineering 106(2):193-202 (2010), West et al., Catalysis Communications 10(13):1743-1746 (2009), Kunkes et al., Science 322 (5900):417-412 (2008), West et al., ChemSusChem 1(5):417-424 (2008), Huber et al., Angewandte Chemie, International Edition 43(12):1549-1551 (2004), and Huber et al., Science 308(5727:1446-1450 (2005), each incorporated herein by reference.

Metabolically Engineered Microorganisms

The mixtures of $C_{10}$-$C_{13}$ alkenes having a particular distribution also can be prepared using metabolically engineered organisms. The preparation of fatty alcohols, fatty aldehydes, fatty acids, and derivatives thereof from genetically-modified cells and microorganisms for use in applications such as biofuels, polymers, surfactants, lubricating oil additives, and intermediates for the production of derivatives such as acrylates used in paints, coatings, and adhesive applications, is described in U.S. Patent Application Publication Nos. 2010/0105955 and 2010/0105963; and International Patent Application Publication Nos. WO 2007/136752, WO 2008/119082, and WO 2009/111672, which are incorporated by reference.

For example, Ladygina et al., Process Biochemistry 41:1001-1014 (2006) discloses the microbial production of intracellular, straight chain and branched chain hydrocarbons having different chain lengths from different microorganisms (e.g., cyanobacteria, aerobic bacteria, anaerobic bacteria, yeasts, mycelia fungi). Alvarez et al., Appl. Microbiol. Biotechnol 60:367-376 (2002), incorporated herein by reference, discloses the biosynthesis of high amounts of triacylglycerols, which can be converted into fatty acids, in bacteria (e.g., *Mycobacterium, Streptomyces, Rhodococcus, Nocardia*). The compositions and structures of the triacylglycerols vary depending on the microorganism and the carbon source. Magnuson et al., Microbiol. Mol. Biol. Rev. 57(3):522-542 (1993), incorporated herein by reference, discloses the regulation of fatty acid biosynthesis in *E. coli* (e.g., the level of expression of the fabA and fabB genes appear to establish a basal ratio of unsaturated to saturated fatty acid synthesis in the absence of thermal regulation).

U.S. Provisional Application No. 61/289,039 ("the '039 application," Procter & Gamble), which is incorporated by reference, describes methods for the biological production of anteiso and iso branched fatty acids, and methods for improving the biological production of such anteiso and/or iso branched fatty acids. Specifically, the '039 application describes a method of producing anteiso and/or iso branched-chain fatty acids using bacteria. In general, the method features incorporating a polynucleotide encoding a branched-chain α-keto acid dehydrogenase, or a biologically active fragment or variant thereof, into a suitable cell, such as, for example, by transfecting or transforming the cell with such a polynucleotide. The method can include incorporating a polynucleotide encoding a 3-ketyoacyl-ACP synthase that uses anteiso and/or iso branched-CoA primers as substrates into a suitable cell. In addition, the method can include incorporating a polynucleotide encoding a thioesterase into a suitable cell. Depending on the activity and substrate specificity of the thioesterase, such recombinant cells can produce anteiso and/or iso branched-chain fatty acids having a desired chain length. Any suitable vectors, expression constructs, strains, and cell lines can be used to construct cells having exogenous BCDH, FabH, and/or thioesterase polynucleotides encoding an exogenous branched-chain α-keto acid dehydrogenase, 3-ketoacylACP synthase, and/or thioesterase, respectively. The '039 application also describes methods of engineering cells to produce anteiso and/or iso branched-chain fatty acids, and methods of modifying cells or organisms that naturally produce anteiso and/or iso branched chain fatty acids to produce higher levels of anteiso and/or iso branched chain fatty acids compared to an unmodified cell or organism.

U.S. Patent Application Publication No. 2009/0275097 and PCT Patent Application Publication No. WO 2009/111672, each incorporated herein by reference, disclose routes to producing long chain primary alcohols. In these routes, acyl-CoAs are produced and then converted to the corresponding aldehydes using fatty acyl Co-A reductase. The aldehydes are reduced to long chain primary alcohols. Specifically, a non-naturally occurring microbial organism comprising a malonyl-CoA-independent fatty acid synthesis pathway and an acyl-reduction pathway is cultured. The malonyl-CoA-independent fatty acid synthesis pathway comprises exogenous nucleic acids encoding ketoacyl-CoA acyltransferase or ketoacyl CoA thioase, 3-hydroxyacyl-CoA dehydrogenase, enoyl-CoA hydratase and enoyl-CoA reductase. The acyl-reduction pathway comprises one or more exogenous nucleic acids encoding an acyl-CoA reductase and an alcohol dehydrogenase.

U.S. Patent Application Publication No. 2009/061493, incorporated herein by reference, discloses methods of cultivating microorganisms (e.g., microalgae cell, oleaginous yeast, fungus) containing an exogenous genes that codes a protein selected from the group consisting of a lipase, sucrose transporter, sucrose invertase, fructokinase, polysaccharide-degrading enzyme, a fatty acyl-ACP thioesterase, a fatty acyl-CoA/aldehyde reductase, a fatty aldehyde decarbonylase, and an acyl carrier protein (ACP) for the production of lipids, fatty acids, fatty esters, aldehydes, alcohols, and straight chain alkanes.

PCT Application Publication Nos. WO 2009/085278, WO 2009/140695 and WO 2009/140696, each incorporated herein by reference, describe methods of producing hydrocarbons, fatty acids, fatty aldehydes, fatty alcohols, fatty esters, acyl-CoAs, acyl-ACPs, and/or fatty acid derivatives by engineering microorganisms. The hydrocarbon can be an alkane or an alkene. The alkene can be a terminal $C_3$-$C_{25}$ alkene, straight chain or branched chain, and/or cyclic. The alkane can be a $C_3$-$C_{25}$ alkane, straight chain or branched chain, and/or cyclic. The fatty acid, fatty aldehyde, fatty alcohol, and/or fatty ester, can comprise $C_6$-$C_{26}$ carbon atoms, and can be unsaturated or saturated, straight chain or branched chain, and can include a cyclic moiety. In the '278 application, the alkanes and alkenes are produced by the reduction of fatty acyl-ACP to aldehydes, followed by decarbonylation. In the '696 application, alkanes and alkenes are produced by the direct decarboxylation of fatty acids.

Other references that disclose the production of fatty acids and derivatives thereof using engineering microorganisms include PCT Application Publication Nos. WO 2010/075483, WO 2010/062480, WO 2010/042664, WO 2010/022090, WO 2010/021711, WO 2009/042950, WO 2009/009391, WO 2008/147781, WO 2008/119082, WO 2008/113041, WO 2008/100251, WO 2007/136762, and U.S. Patent Application Publication Nos. 2010/0221798, 2010/0199548, 2010/0170826, 2010/0105963, 2010/0105955, 2010/0071259, 2008/0293060, each incorporated herein by reference.

U.S. Provisional Patent Application No. 61/364,530 ("the '530 application," Procter & Gamble), which is incorporated herein by reference, describes methods for the biological production of fatty alcohols or derivatives thereof having specific chain lengths and degrees of unsaturation. Fatty acid synthase (FAS) is a group of polypeptides that catalyze the initiation and elongation of acyl chains (Marrakchi et al., Biochemical Society, 30:1050-1055 (2002), incorporated herein by reference). The acyl carrier protein (ACP) along with the enzymes in the FAS pathway control the length, degree of saturation, and branching of the fatty acid derivatives produced. The steps in this pathway are catalyzed by enzymes of the fatty acid biosynthesis (fab) and acetyl Co-A carboxylase (acc) gene families (see, e.g, Heath et al., Prog. Lipid Res., 40(6):467-497 (2001), incorporated herein by reference).

The '530 application discloses that host cells can be engineered to express fatty acid derivative substrates by recombinantly expressing or overexpressing one or more fatty acid synthase genes, such as acetyl-CoA and/or malonyl-CoA synthase genes. In addition, inhibiting PlsB can lead to an increase in the levels of long chain acyl-ACP, which will inhibit early steps in the pathway (e.g, accABCD, fabH, and fabI). The plsB (e.g., accession number AAC77011) D311E mutation can be used to increase the amount of available fatty acids. Host cells also can be engineered to overexpress a sfa gene (suppressor of fabA, e.g., accession number AAN79592) to increase production of monounsaturated fatty acids (Rock et al., J. Bacteriology 178:5382-5387 (1996), incorporated herein by reference).

The '530 application further discloses that the chain length of a fatty acid derivative substrate can be selected for by modifying the expression of selected thioesterases. Thioesterase influences the chain length of fatty acids expressed by selected thioesterases. Therefore, host cells can be engineered to express, overexpress, have attenuated expression, or not to express one or more selected thioesterases to increase the production of a preferred fatty acid substrate. For example, $C_{10}$ fatty acids can be produced by expressing a thioesterase that has a preference for producing $C_{10}$ fatty acids and attenuating thioesterases that have a preference for producing fatty acids other than $C_{10}$ fatty acids (e.g., a thioesterase that prefers to produce $C_{14}$ fatty acids). This would result in a relatively homogeneous population of fatty acids that have a carbon chain length of 10. In some situations, $C_{12}$ fatty acids can be produced by expressing thioesterases that have a preference for $C_{12}$-ACP and attenuating thioesterases that preferentially produce non-$C_{12}$ fatty acids. Acetyl-CoA, malonyl-CoA, and fatty acid overproduction can be verified using methods known in the art, for example, by using radioactive precursors, HPLC, or GC-MS subsequent to cell lysis. Nonlimiting examples of thioesterases that can be used in the above described methods are disclosed in the '530 application.

Still further, the '530 application discloses the expression of a fatty aldehyde biosynthetic polypeptide, variant, or a fragment thereof in a host cell that contains a naturally occurring mutation that results in an increased level of fatty acids in the host cell. In some instances, the host cell is genetically engineered to increase the level of fatty acids in the host cell relative to a corresponding wild-type host cell. In some embodiments, the level of expression of one or more genes is reduced by genetically engineering a "knock out" host cell.

Even further, the '530 application discloses that biofermentation methods also can be used to produce fatty acids that contain branch points. For example, although *E. coli* naturally produces straight chain fatty acids, *E. coli* can be engineered to produce branched chain fatty acids by introducing and expressing or overexpressing genes that provide branched precursors in *E. coli*(e.g., by expressing genes from the following gene families: bkd, ilv, icm, and fab). Additionally, a host cell can be engineered to express or overexpress genes encoding proteins for the initiation (e.g., FabH) and elongation of branched chain fatty acids (e.g., ACP, FabF, etc.) and/or to delete or attenuate the corresponding host cells genes that normally lead to straight chain fatty acids.

The first step in forming branched chain fatty acids is the production of the corresponding α-keto acids by a branched-chain amino acid aminotransferase. Host cells may endogenously include genes encoding such enzymes or such genes can be recombinantly introduced. *E. coli*, for example, endogenously expresses such an enzyme, IlvE (EC 2.6.1.42; GenBank accession YP_026247). In some host cells, a heterologous branched-chain amino acid aminotransferase may not be expressed. However, *E. coli* IlvE or any other branched-chain amino acid aminotransferase (e.g., IlvE from *Lactococcus lactis* (GenBank accession AAF34406), IlvE from *Pseudomonas putida* (GenBand accession NP_745648), or IlvE from *Streptomyces coelicolor* (GenBank accession NP_629657)), if not endogenous, can be introduced. In another embodiment, the production of α-keto acids can be achieved by using methods described in Park et al., PNAS, 104:7797-7802 (2007) and Atsumi et al., Nature 451:86-89 (2008), each incorporated herein by reference.

The second step is the oxidative decarboxylation of the α-keto acids to the corresponding branched-chain acyl-CoA. This reaction can be catalyzed by a branched-chain α-keto acid dehydrogenase comples (bkd; EC 1.2.4.4) (Denoya et al., J. Bacteriol., 177:3504 (1995), incorporated herein by reference), which consists of E1α/β (decarboxylase), E2 (dihydrolipoyl transacylase), and E3 (dihydrolipolyl dehydrogenase) subunits. These branched-chain α-keto acid dehydrogenase complexes are similar to pyruvate dehydrogenase complexes and α-ketoglutarate dehydrogenase complexes. Any microorganism that possesses branched chain fatty acids and/or grows on branched-chain fatty acids can be used to isolate bkd genes for expression in host cells, for example, *E. coli*. Furthermore, *E. coli* has the E3 component as part of its pyruvate dehydrogenase complex (lpd, EC 1.8.1.4, GenBank accession NP_414658). Thus, it may be sufficient to express only the E1α/β and E2 bkd genes. Nonlimiting examples of such bkd genes from several microorganisms that can be recombinantly introduced and expressed in a host cell to provide branched-chain acyl-CoA precursors can be found in the '530 application.

The '530 application also discloses that isobutyryl-CoA can be made in a host cell, for example in *E. coli*, through the coexpression of crotonyl-CoA reductase (Ccr, EC 1.6.5.5, 1.1.1.1) and isobutyryl-CoA mutase (large subunit IcmA, EC 5.4.99.2; small subunit IcmB, EC 5.4.99.2) (Han and Reynolds, J. Bacteriol., 179:5157 (1997), incorporated herein by reference). Crotonyl-CoA is an intermediate in fatty acid biosynthesis in *E. coli* and other microorganisms. Nonlimiting examples of ccr and icm genes from selected microorganisms are disclosed in the '530 application. In addition to expression of the bkd genes, a β-ketoacyl-acyl-carrier-protein-synthase 111 (FabH, EC 2.3.1.41) with preferred specificity for branched chain acyl-CoAs (Li et al., J. Bacteriol., 187:37953799 (2005) can be heterologously overexpressed to increase branched-chain fatty acid biosynthesis. Nonlimiting examples of such FabH enzymes can be found in the '530 application. fabH genes that are involved in fatty acid biosynthesis of any branched-chain fatty acid-containing microorganism can be expressed in a host cell. The Bkd and FabH enzymes from host cells that do not naturally make branched-chain fatty acids may not support branched-chain fatty acid production. Therefore, bkd and fabH can be expressed recombinantly. Vectors containing the bkd and fabH genes can be inserted into such a host cell. Similarly, the endogenous level of Bkd ad FabH production may not be sufficient to produce branched-chain fatty acids. In this case they can be overexpressed. Additionally, other components of the fatty acid biosynthesis pathway can be expressed or overexpressed, such as acyl carrier proteins (ACPs) and β-ketoacyl-acyl-carrier-protein synthase II (fabF, EC 2.3.1.41). Nonlimiting examples of candidates can be found in the '530 application. In addition to expressing these genes, some genes in the endogenous fatty acid biosynthesis pathway can be attenuated in a host cell (e.g., the *E. coli* genes fabH (GenBank accession # NP_415609) and/or fabF (GenBank accession # NP_415613)).

The '530 application also discloses that the degree of saturation in biosynthetic fatty acids also can be controlled. The sfa, gns, and fab families of genes can be expressed or overexpressed to control the saturation of fatty acids. Nonlimiting examples of genes in these gene families are disclosed in the '530 application. Host cells can be engineered to produce unsaturated fatty acids by engineering the production host to overexpress fabB or by growing the production host at low temperatures (e.g., less than about 37° C.). FabB has preference to cis-δ3decenoyl-ACP and results in unsaturated fatty acid production in *E. coli*. Overexpression of fabB results in the production of a significant percentage of unsaturated fatty acids (de Mendoza et al., J. Biol. Chem., 258:2098-2101 (1983), incorporated herein by reference). The gene fabB may be inserted into and expressed in host cells not naturally having the gene. In other instances, a repressor of fatty acid biosynthesis, for example, fabR (GenBank accession NP_418398), can be deleted, which also will result in increased unsaturated fatty acid production in *E. coli* (Zhang et al., J. Biol. Chem., 277:15558 (2002), incorporated herein by reference). Similar deletions may be made in other host cells. A further increase in unsaturated fatty acids may be achieved, for example, by overexpressing fabM (trans-2, cis-3-decenoyl-ACP isomerase, GenBank accession DAA05501) and controlled expression of fabK (trans-2-enoyl-ACP reductase II, GenBank accession NP_357969) from *Streptococcus pneumonia* (Marrakchi et al., J. Biol. Chem., 277:44809 (2002), incorporated herein by reference), while deleting *E. coli* fabI (trans-2-enoyl-ACP reductase, GenBank accession NP_415804).

According to the '530 application, various host cells can be used to produce fatty acids. A host cell can be any prokaryotic or eukaryotic cell. For example, a gene, as described herein, can be expressed in a bacterial cell (e.g., *E. coli*), insect cells, yeast or mammalian cells (e.g., Chinese hamster ovary cells (CHO) cells, COS cells, VERO cells, BHK cells, HeLa cells, Cv1 cells, MDCK cells, 293 cells 3T3 cells, or PC12 cells.

Other exemplary host cells include cells from the members of the genus *Escherichia*, *Bacillus*, *Lactobacillus*, *Rhodococcus*, *Tseudomonas*, *Aspergillus*, *Trichoderma*, *Neurospora*, *Fusarium*, *Humicola*, *Rhizomucor*, *Kluyveromyces*, *Pichia*, *Mucor*, *Myceliophtora*, *Penicillium*, *Phanerochaete*, *Pleurotus*, *Trametes*, *Chrysosporium*, *Saccharomyces*, *Schizosaccharomyces*, *Tarrowia*, or *Streptomyces*. Yet other exemplary host cells can be a *Bacillus lentus* cell, a *Bacillus brevis* cell, a *Bacillus stearothermophilus* cell, a *Bacillus licheniformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, a *Bacillus amyloliquefaciens* cell, a *Trichoderma koningii* cell, a *Trichoderma viride* cell, a *Trichoderma reesei* cell, a *Trichoderma longibrachiatum* cell, an *Aspergillus awamori* cell, an *Aspergillus fumigates* cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhizomucor miehei* cell, a *Mucor michei* cell, a *Streptomyces lividans* cell, a *Streptomyces murinus* cell, or an Actinomycetes cell. Other host cells are cyanobacterial cells. In a preferred embodiment, the host cell is an *E. coli* cell, a *Saccharomyces cerevisiae* cell, or a *Bacillus subtilis* cell. In a more preferred embodiment, the host cell is from *E. coli* strain B, C, K, or W. Other suitable host cells are known to those in the art.

The mixtures of $C_{10}$-$C_{13}$ alkenes having a particular distribution can be produced using the previously described methods that utilize engineered microorganisms. In these methods, various host cells can be used, as previously described. In some embodiments, exogenous acyl-ACP reductase and exogenouse decarbonylase are expressed in a microorganism (e.g., *E. coli*) to generate alkanes and/or alkenes with particular chain lengths via the fatty acid synthesis pathway, as previously described. In alternative embodiments, fatty acids can be fermented in two different organisms with their maximum production each at a particular chain length. The products then can be combined.

Using microorganisms to produce the mixtures of $C_{10}$-$C_{13}$ alkenes having a particular distribution is advantageous. These methods allow complete tunability to produce mixtures of alkenes having different distributions. They minimizes the requirement of chemically oxidizing paraffins because the product that is produced as a higher alkene to paraffin ratio than traditional processes. They allow the production of linear, branched, or a mixture of linear and branched alkenes. Further, a variety of gene sources can be used to produce the fatty acid precursors and to convert fatty acids, fatty acyl-ACP, fatty acyl-CoAs into alkanes and alkenes. Further still the process uses low cost, renewable feedstocks (i.e., sugar) instead of petroleum-based feedstocks.

The fatty acids or esters or triglycerides prepared either from such microorganisms or from standard plant based fats and oils or fatty acids can be decarboxylated to alkenes as described in PCT Patent Application No. WO 2007/136873, incorporated herein by reference. Fatty alcohols derived from microbial production either directly via bioengineering or via microbial production of the methyl ester or fatty acid can be converted into fatty alcohols by standard reduction practices in the industry. Plant derived fats and oils can also be trans-esterified and reduced to fatty alcohols. Both types of fatty alcohols can also become alkene feedstock for production of alkylbenzenes as described herein by means of industry standard practices for alcohol dehydration such as practiced by WO09905084A1 or other industrially relevant processes used for alcohol dehydration. Furthermore, the fatty alcohols can also be converted directly to a bio LAB without the need for dehydration using as described in WO09905084A1.

Alkylation of Benzene with the Mixture of Optionally Renewable $C_{10}$-$C_{13}$ Alkenes The mixture of optionally renewable $C_{10}$-$C_{13}$ alkenes produced by any method described herein or known in the art can be used to alkylate benzene to form a mixture of $C_{10}$-$C_{13}$ alkylbenzenes having particular alkyl chain distributions, as described in the section "Mixtures of Optionally Renewable $C_{10}$-$C_{13}$ Alkylbenzenes."

The benzene used for alkylation can be derived from a renewable resource, a petroleum resource, or a mixture thereof. In some optional embodiments, benzene has a bio-based content of at least about 50%, more preferably at least about 75%, even more preferably at least about 95%, for example about 100%, as determined by ASTM D6866. Renewable benzene can be produced by the metathesis of any C18-3 component of oil/fat (e.g., linoleic type) to generate 1,4,7-decatriene. The 1,4,7-decatriene is cyclized in situ, in the presence of a metathesis catalyst, to form 1,3-cyclohexadiene, and then the cyclohexadiene is dehydrogenated to form bio-benzene. Renewable benzene also can be produced from the hydrocracking of lignin, which results in renewable benzene and phenol. The bio-phenol can be subsequently dehydroxylated to produce the renewable benzene, as described in U.S. Pat. No. 4,420,644, which is incorporated herein by reference. Bio-based benzene can also be produced by treating carbohydrates in an aqueous phase with catalytic chemistry to reduce the oxygen content; this aqueous mixture can then be treated with conventional petrochemical catalysts to produce mixtures of benzene, toluene and xylenes. The bio-based benzene can be separated by conventional processes and used in the alkylation process. The process to produce this catalytically derived benzene is described in U.S. Pat. No. 7,977,517, which is incorporated herein by reference.

Alkylation of benzene by the mixture of optionally renewable $C_{10}$-$C_{13}$ alkenes can be accomplished by any method known to one skilled in the art, see, e.g., U.S. Pat. Nos. 6,583,096, 6,514,926, and PCT Patent Application Publication No. WO 2009/079213, each incorporated herein by reference. For example, alkylation can be performed at a temperature of about 125° C. to about 230° C., preferably about 175° C. to about 215° C., and at a pressure of about 50 psig to about 1000 psig, preferably about 100 psig about 250 psig. The reaction time for this alkylation can vary; however, it is preferred that the reaction is about 0.01 hour to about 18 hours, more preferably, as rapidly as possible, more typically about 0.1 hour to about 5 hours, or about 0.1 hour to about 3 hours.

Generally, it is preferable to couple together the use of relatively low temperatures (e.g., about 175° C. to about 215° C.) with reaction times of medium duration (e.g., 1 hour to about 8 hours) in the above-indicated ranges. Moreover, it is contemplated that the alkylation of the benzene be "staged" so that two or more reactors operating under different conditions in the defined ranges may be useful.

In some embodiments, the $C_{10}$-$C_{13}$ alkylbenzenes of the invention can be produced directly from fatty acids, fatty esters, fats, and/or oils by combining the fatty acids, fatty esters, fats, and/or oils with benzene in the presence of a good decarboxylation catalyst/weak alkylation catalyst at 300-400° C. and simulataneously decarboxylating to alkenes and alkylating the aromatic mixture, as described in U.S. Pat. No. 7,683,224, incorporated herein by reference.

Alkylation Catalyst

Alkylation of benzene can be carried out using mineral acids (e.g., solid phosphoric acid) and Friedel-Crafts catalysts (e.g, $AlCl_3$-HCl). Benzene can be alkylated with linear alkenes using DETAL® process catalysts, HF, aluminum chloride, HF on zeolites, fluoridated zeolites, non-acidic calcium mordenite, and amorphous silica/aluminua. Such process that use these catalysts include the DETAL® process of UOP and CEPSA (Petresa) and processes described in U.S. Pat. Nos. 6,602,840; 5,344,997; 5,196,574; 5,334,793; 5,245,094, each of which is incorporated herein by reference.

Benzene can be alkylated with branched alkenes using a zeolite beta catalyst comprising a medium-pore size, which may be fluoridated or non-fluoridated. In some embodiments, the zeolite beta catalyst is an acidic zeolite beta catalyst. The preferred acidic zeolite beta catalysts are HF-treated calcined zeolite beta catalysts. A particularly preferred alkylation catalyst comprises at least partially dealuminized acidic nonfluoridated or at least partially dealuminized acidic fluoridated zeolite beta. Examples and use of these zeolite catalysts (e.g., zeolite beta, HZSM-4, HZSM20, HZSM-38) are disclosed in U.S. Pat. Nos. 6,583,096, and 6,514,926, each incorporated herein by reference, and are supplied by, for example, Zeochem or UOP Chemical Catalysts and Zeolyst International.

Optionally, depending on feedstock and the precise sequence of steps used, the present process can include distillation of the alkylbenzenes to remove impurities and by-products, such as unreacted starting materials, paraffins, and excesses of benzene. Any conventional distillation apparatus can be used. The general practice for distillation is similar to that used for distillation of commercial linear alkylbenzenes (LAB), and suitable distillation steps are described in Surfactant Science Series, Marcel Dekker, New York, 1996, including in particular Chapter 2 entitled "Alkylarylsulfonates: History, Manufacture, Analysis and Environmental Properties", pages 39-108 which includes 297 literature references and is incorporated herein by reference.

The mixture of optionally renewable $C_{10}$-$C_{13}$ alkylbenzenes having particular chain length distributions can be made in one pot. In these methods, the alkene reactants are selected to result in alkylbenzene products having particular alkyl chain distributions (e.g., bimodal distribution having an average total carbon number of 10.9). In some embodiments, the mixture of $C_{10}$-$C_{13}$ alkylbenzenes having particular chain length distributions is made by synthesizing separate batches of alkylbenzenes, each having alkyl chains with a particular number of total carbon atoms (e.g., a $C_{10}$ batch, a $C_{11}$ batch, a $C_{12}$ batch, and a $C_{13}$ batch), and then combining the batches in particular concentrations to form a mixture having a particular alkyl chain distribution.

Sulfonation of Alkylbenzene

Sulfonation of the alkylbenzenes can be accomplished using any sulfonation system, including those described in "Detergent Manufacture Including Zeolite Builders and Other New Materials," Ed. M. Sittig, Noyes Data Corporation, 1979, incorporated herein by reference, as well as in the hereinabove-referenced Surfactant Science Series review. Common sulfonation systems include sulfuric acid, chlorosulfonic acid, oleum, sulfur trioxide with and without air. Sulfur trioxide/air is especially preferred, and details of this process are provided in U.S. Pat. No. 3,427,342, and de Groot, "Sulfoantion Technology in the Detergent Industry" Kluwer Academic Publishers, Boston, 1991, each incorporated herein by reference.

Any convenient workup steps may be used in the present process. In some embodiments, the product is neutralized after sulfonation using any suitable alkali metal (e.g., sodium, potassium, ammonium, magnesium substituted ammonium alkalis, and mixtures thereof). Potassium can assist solubility, magnesium can promote soft water performance and substituted ammonium can be helpful for formulating specialty variations of the instant surfactants. Sodium-form alkali, such as sodium hydroxide, is most commonly used. In some preferred embodiments, the alkali metals are selected from the group consisting of sodium hydroxide, potassium hydroxide, ammonium hydroxide, sodium carbonate, potassium carbonate, and mixtures thereof. If the alkylphenyl sulfonate is to be mixed with cleaning components, it can be added in the acid form directly to the cleaning composition and then neutralized.

The mixture of $C_{10}$-$C_{13}$ alkylphenyl sulfonates having particular chain length distributions can be made in one pot. In these methods, the alkylbenzenes that are being sulfonated are selected to result in alkylphenyl sulfonate products having particular alkyl chain distributions (e.g., bimodal distribution having an average total carbon number of 10.9). In some embodiments, the mixture of $C_{10}$-$C_{13}$ alkylphenyl sulfonates having particular chain length distributions is made by synthesizing separate batches of alkylphenyl sulfonates, each having a particular number of total carbon atoms on its alkyl chain (e.g., a $C_{10}$ batch, a $C_{11}$ batch, a $C_{12}$ batch, and a $C_{13}$ batch), and then combining the batches in particular concentrations to form a mixture of alkylphenyl sulfonates having a particular alkyl chain distribution.

Blended Embodiments

Prior to the sulfonation step, the optionally renewable $C_{10}$-$C_{13}$ alkylbenzene of the invention can blended with petroleum-based alkylbenzene. Further, in any step subsequent to said sulfonation step, the optionally renewable $C_{10}$-$C_{13}$ alkylphenyl sulfonate of the invention (acid-form or neutralized-form) can be blended with a petroleum-derived alkylphenyl sulfonate. In these blended embodiments, blends can be made at a weight ratio of the bio-based compounds to the petroleum-based compounds, or their derivatives, of 100:1 to 1:100, 10:90 to 50:50, or 51:49 to 92:8

Assessment of the Biobased Content of Materials

A suitable method to assess materials derived from renewable resources is through ASTM D6866, which allows the determination of the biobased content of materials using radiocarbon analysis by accelerator mass spectrometry, liquid scintillation counting, and isotope mass spectrometry. When nitrogen in the atmosphere is struck by an ultraviolet light produced neutron, it loses a proton and forms carbon that has a molecular weight of 14, which is radioactive. This $^{14}C$ is immediately oxidized into carbon dioxide, which represents a small, but measurable fraction of atmospheric carbon. Atmospheric carbon dioxide is cycled by green plants to make organic molecules during the process known as photosynthesis. The cycle is completed when the green plants or other forms of life metabolize the organic molecules producing carbon dioxide, which causes the release of carbon dioxide back to the atmosphere. Virtually all forms of life on Earth depend on this green plant production of organic molecules to produce the chemical energy that facilitates growth and reproduction. Therefore, the $^{14}C$ that exists in the atmosphere becomes part of all life forms and their biological products. These renewably based organic molecules that biodegrade to carbon dioxide do not contribute to global warming because no net increase of carbon is emitted to the atmosphere. In contrast, fossil fuel-based carbon does not have the signature radiocarbon ratio of atmospheric carbon dioxide. See WO 2009/155086, incorporated herein by reference.

The application of ASTM D6866 to derive a "biobased content" is built on the same concepts as radiocarbon dating, but without use of the age equations. The analysis is performed by deriving a ratio of the amount of radiocarbon ($^{14}C$) in an unknown sample to that of a modern reference standard. The ratio is reported as a percentage with the units "pMC" (percent modern carbon). If the material being analyzed is a mixture of present day radiocarbon and fossil carbon (containing no radiocarbon), then the pMC value obtained correlates directly to the amount of biomass material present in the sample.

The modern reference standard used in radiocarbon dating is a NIST (National Institute of Standards and Technology) standard with a known radiocarbon content equivalent approximately to the year AD 1950. The year AD 1950 was chosen because it represented a time prior to thermo-nuclear weapons testing, which introduced large amounts of excess radiocarbon into the atmosphere with each explosion (termed "bomb carbon"). The AD 1950 reference represents 100 pMC.

"Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. The distribution of bomb carbon has gradually decreased over time, with today's value being near 107.5 pMC. As a result, a fresh biomass material, such as corn, could result in a radiocarbon signature near 107.5 pMC.

Petroleum-based carbon does not have the signature radiocarbon ratio of atmospheric carbon dioxide. Research has noted that fossil fuels and petrochemicals have less than about 1 pMC, and typically less than about 0.1 pMC, for example, less than about 0.03 pMC. However, compounds derived entirely from renewable resources have at least about 95 percent modern carbon (pMC), preferably at least about 99 pMC, for example, about 100 pMC.

Combining fossil carbon with present day carbon into a material will result in a dilution of the present day pMC content. By presuming that 107.5 pMC represents present day biomass materials and 0 pMC represents petroleum derivatives, the measured pMC value for that material will reflect the proportions of the two component types. A material derived 100% from present day soybeans would give a radiocarbon signature near 107.5 pMC. If that material was diluted with 50% petroleum derivatives, it would give a radiocarbon signature near 54 pMC.

A biobased content result is derived by assigning 100% equal to 107.5 pMC and 0% equal to 0 pMC. In this regard, a sample measuring 99 pMC will give an equivalent biobased content result of 93%.

Assessment of the materials described herein were done in accordance with ASTM D6866, particularly with Method B. The mean values quoted in this report encompasses an absolute range of 6% (plus and minus 3% on either side of the biobased content value) to account for variations in end-component radiocarbon signatures. It is presumed that all materials are present day or fossil in origin and that the desired result is the amount of biobased component "present" in the material, not the amount of biobased material "used" in the manufacturing process.

Other techniques for assessing the biobased content of materials are described in U.S. Pat. Nos. 3,885,155, 4,427,884, 4,973,841, 5,438,194, and 5,661,299, and WO 2009/155086, each incorporated herein by reference.

Determination of Alkene and Alkyl Chain Distribution

The $C_{10}$-$C_{13}$ alkenes, $C_{10}$-$C_{13}$ alkylbenzenes, and $C_{10}$-$C_{13}$ alkylphenyl sulfonates of the invention (e.g., chain length, phenyl isomer content of alkylbenzenes, impurity content, such as tetralins) can be characterized using gas chromatography and NMR, as described in PCT Application No. WO 2008/046106, for example, on pages 42-45.

For example, analytical analysis of the mixtures of the invention can be performed using gas chromatography. A calibration solution is prepared by weighing 5 grams of pure hexadecane to the nearest 0.0001 g and adding it to a 100 mL volumetric flask. The flask is filled to volume with methylene chloride, stoppered, and mixed well. A sample solution is prepared in the following way. The mixture of the invention is passed through a PTFE syringe filter (0.45 μm) and a 2 mL GC vial is tared. 50 μL of the mixture is dispensed into the GC vial using a micro-pipette and the vial is weighed. 1000 μL of the calibration solution is added to the GC vial and the weight is recorded to the nearest 0.1 mg. The vial is crimp-sealed and the contents of the vial are shaken. The sample is injected into a GC that has the following parameters.

| Fast GC Method Instrument Operation<br>Column: Restek RTX-5 (10244) 105 m × 0.25 mm × 0.50um df<br>Oven: Maximum temp.: 330° C. | |
|---|---|
| Total run time: | 35 min |
| Initial temp: | 180° C. |
| Initial time: | 0.0 min |
| Rate: | 5.0 C.°/min |
| Final temp: | 320° C. |
| Final time: | 7.0 min |
| Inlet: | |
| Mode: | Split |
| Split Ratio: | 50:1 |
| Inlet temp: | 300° C. |
| Carrier gas: | He |
| Linear velocity: | 20 cm/sec. |
| Injector: | |
| Injection volume: | 0.2 μL |
| Sample washes: | 3 |
| Sample pumps: | 5 |
| Solvent A&B: | DCM ($CH_2Cl_2$) |
| Solvent washes (A): | 3 |
| Solvent washes (B): | 3 |
| Detector (FID): | |
| Temp. | 320° C. |
| Hydrogen flow: | 40 mL/min |
| Air flow: | 450 mL/min |
| Makeup gas: | $N_2$ |
| Makeup flow: | 45 mL/min |

Commercial Uses

The mixtures of renewable $C_{10}$-$C_{13}$ alkylphenyl sulfonates of the invention that have particular distributions can be included in consumer product cleaning or personal care compositions for improved performance and superior properties, as previously described. Thus, in another aspect, the invention relates to a composition comprising about 0.001 wt. % to about 99.999 wt. %, preferably about 0.1 wt. % to about 80 wt. % of the mixture of renewable $C_{10}$-$C_{13}$ alkylphenyl sulfonates of the invention, as previously described, and about 0.001 wt. % to about 99.999 wt. % of one or more additional cleaning components or about 0.001 wt. % to about 99.999 wt. % of one or more additional personal care components.

In some alternative embodiments, the mixture of the invention comprises optionally renewable alkylphenyl sulfonates having alkyl groups with 10, 11, and/or 12 carbon atoms. In these embodiments, alkylphenyl sulfonates having alkyl groups with 13 carbon atoms are present in an amount of no more than about 30 wt. %, preferably no more than about 20 wt. %, more preferably no more than about 10 wt. %. This mixture of alkylphenyl sulfonates having $C_{10}$-$C_{12}$ alkyl groups is useful for, for example, laundry detergents. In other alternative embodiments, the mixture of the invention comprises optionally renewable alkylphenyl sulfonates having alkyl groups with 10 and/or 11 carbon atoms. In these embodiments, alkylphenyl sulfonates having alkyl groups with 12 carbon atoms are present in an amount of no more than about 30 wt. %, preferably no more than about 20 wt. %, more preferably no more than about 10 wt. %, and alkylphenyl sulfonates having alkyl groups with 13 carbon atom are present in an amount of no more than about 5 wt. %. This mixture of alkylphenyl sulfonates having $C_{10}$-$C_{11}$ alkyl groups is useful for, for example, increasing the sudsing of dishwashing liquids.

Consumer Product Cleaning Compositions

Consumer product cleaning compositions are described in the "Surfactant Science Series", Marcel Dekker, New York, Volumes 1-67 and higher, which is incorporated herein by reference. In particular, liquid compositions are described in detail in Volume 67, "Liquid Detergents," Ed. Kuo-Yann Lai, 1997, ISBN 0-8247-9391-9, incorporated herein by reference. More classical formulations, especially granular type formulations, are described in "Detergent Manufacture including Zeolite Builders and Other New Materials", Ed. M. Sittig, Noyes Data Corporation, 1979, incorporated herein by reference. See also Kirk Othmer's Encyclopedia of Chemical Technology. Nonlimiting examples of consumer product cleaning compositions include light duty liquid detergents (LDL), heavy duty liquid detergents (HDL), heavy duty granular detergents (HDG), softergents (STW), hard surface cleaners (HSC), bar soaps, fabric softeners (FS), and special purpose cleaners (SPC). Any of the aforementioned examples of consumer product cleaning compositions can optionally include perfume, as described in U.S. Pat. No. 5,500,154 and WO 96/02490, each incorporated herein by reference.

Light duty liquid detergents include compositions having surfactancy improving magnesium ions (see, e.g., WO 97/00930A; GB 2,292,562A; U.S. Pat. Nos. 5,376,310; 5,269,974; 5,230,823; 4,923,635; 4,681,704; 4,316,824; 4,133,779, each incorporated herein by reference), organic diamines, various foam stabilizers, foam boosters such as amine oxides (see, e.g., U.S. Pat. No. 4,133,779, incorporated herein by reference), skin feel modifiers of surfactant, emollient, and enzymatic types including proteases, antimicrobial agents, and mixtures thereof (see, e.g., Surfactant Science Series, Vol. 67, pages 240-248, incorporated herein by reference).

Heavy duty liquid detergents include both "structured" (i.e., multi-phase) liquid types (see, e.g., U.S. Pat. Nos. 4,452,717; 4,526,709; 4,530,780; 4,618,446; 4,793,943; 4,659,497; 4,871,467; 4,891,147; 5,006,273; 5,021,195; 5,147,576; 5,160,655, each incorporated herein by reference) and "non-structured" (i.e., isotropic) liquid types, and can be aqueous or nonaqueous (see, e.g., EP 738,778A; WO 97/00937A; WO 97/00936A; EP 752,466A; DE 19623623A; WO 96/10073A;

WO 96/10072A; EP 225,654; WO 94/23009; U.S. Pat. Nos. 4,647,393; 4,648,983; 4,655,954; 4,661,280; 4,690,771; 4,744,916; 4,753,750; 4,950,424; 5,004,556; and 5,102,574, each incorporated herein by reference). The HDLs can optionally comprise bleach (see, e.g., U.S. Pat. Nos. 4,470, 919; 5,250,212; 5,264,143; 5,275,753; 5,288,746; 5,431,848; and 5,445,756; EP 564,250; WO 94/11483; EP 598,170; EP 598,973; and EP 619,368, each incorporated herein by reference). Additionally or alternatively, the HDLs can optionally comprise enzymes (see, e.g., U.S. Pat. Nos. 3,944,470; 4,111, 855; 4,261,868; 4,287,082; 4,305,837; 4,404,115; 4,462,922; 4,529,5225; 4,537,706; 4,537,707; 4,670,179; 4,842,758; 4,900,475; 4,908,150; 5,082,585; 5,156,773; 5,269,960; 5,422,030; 5,431,842; and 5,442,100; WO 92/19709; EP 583, 534; EP 583,535; EP 583,536; WO 94/04542; and EP 633, 311, each incorporated herein by reference). Also see Surfactant Science Series, Vol. 67, pages 309-324, incorporated herein by reference.

Heavy duty granular detergents include both the "compact" (i.e., agglomerated or otherwise non-spray-dried) type, and the "fluffy" (i.e., spray-dried) type. The compact and fluffy types of HDGs either can be phosphated or nonphosphated. The HDGs can include the anionic-surfactant based type or the "high-nonionic surfactant" type (i.e., the nonionic surfactant is held in or on an absorbent, such as zeolites or other porous inorganic salts). Manufacture of HDGs is disclosed in, e.g., EP 753,571A; WO 96/38531A; U.S. Pat. Nos. 5,576,285; 5,573,697; 5,569,645; 5,565,422; 5,496,487; 5,489,392; and 5,554,587; U.S. Patent Application NO. 96/34082A; EP 739,977A; EP 737,739A; WO 96/27655A; WO 96/25482A; WO 96/23048A; WO 96/22352A; EP 709, 449A; WO 96/09370A; and EP 694,608A, each incorporated herein by reference.

Softergents include various granular or liquid softening-through-the wash types of product and can include organic (e.g., quaternary) or inorganic (e.g., clay) softeners (see, e.g., U.S. Pat. Nos. 4,140,641; 4,639,321; 4,751,008; 4,844,821; 4,844,824; 4,873,001; 4,911,852; and 5,017,296; EP 753, 569A; EP 315,126; and EP 422,787, each incorporated herein by reference).

Hard surface cleaners include all-purpose cleaners, such as, for example, cream cleansers, liquid cleaners, and spray cleaners (e.g., glass cleaners, tile cleaners, bleach spray cleaners); and bathroom cleaners (e.g., mildew-removing, bleach-containing, antimicrobial, acidic type, neutral type, basic types). See, for example, EP 743,280A; EP 743,279A, and WO 96/34938 A, each incorporated herein by reference.

Bar soaps include laundry bars. The bar soaps encompass both the synthetic detergent (i.e., syndet) type, the soap-based type, and types with softener (see, e.g., WO 96/35772A; U.S. Pat. No. 5,500,137; and WO 96/01889A, each incorporated herein by reference). These compositions can include those made by common soap-making techniques, such as plodding, and/or more unconventional techniques, such as casting, absorption of surfactant into a porous support, or the like. Other bar soaps, such as those described in BR 9502668; WO 96/04361A; WO 96/04360A; and U.S. Pat. No. 5,540,852, each incorporated herein by reference are also included, as well as other handwash detergents, such as those described in GB 2,292,155 A and WO 96/01306 A, each incorporated herein by reference.

Fabric softeners include both the conventional liquid and liquid concentrate types (see, e.g., EP 754,749A; WO 96/21715A; EP 705,900A; U.S. Pat. Nos. 5,531,910 and 5,500,138, each incorporated herein by reference), as well as dryer-added or substrate-supported types (see, e.g., U.S. Pat. Nos. 5,562,847 and 5,559,088; and EP 704,522A, each incorporated herein by reference). Other fabric softeners include solids, as described in, for example, U.S. Pat. No. 5,505,866, which is incorporated herein by reference.

Special purpose cleaners include home dry cleaning systems (see, e.g., WO 96/30583A; WO 96/30472A; WO 96/30471A; U.S. Pat. No. 5,547,476; WO 96/37652 A); bleach pretreatment products for laundry (see, e.g., EP 751, 210 A); fabric care pretreatment products (see, e.g., EP 752, 469 A); liquid fine fabric detergent types, especially the high-foaming variety; rinse-aids for dishwashing; liquid bleaches including both chlorine type and oxygen bleach type; disinfecting agents; car or carpet cleaners or shampoos (see, e.g., EP 751,213A; WO 96/15308A); metal cleaners; cleaning auxiliaries (e.g., bleach additives, stain-sticks, pre-treatments including special foam type cleaners, as described in EP 753,560A; EP 753,559A; EP 753,558A; EP 753,557A; EP 753,556A, each incorporated herein by reference); and anti-sunfade treatments (see, e.g., WO 96/03486A; WO 96/03481A; WO 96/03369A, each incorporated herein by reference).

Consumer product cleaning compositions, can be formulated into a wide range of forms including, for example, powders, liquids, granules, gels, pastes, tablets, pouches, bars, types delivered in dual-compartment containers, spray or foam detergents and other homogeneous or multiphasic consumer cleaning product forms.

The consumer product compositions of the invention can be applied by hand in unitary or freely alterable dosage, or by automatic dispensing means. The consumer product compositions of the invention are useful in appliances, (e.g., washing machines, dishwashers), in institutional cleaning contexts (e.g., personal cleansing in public facilities), for bottle washing, for surgical instrument cleaning, and/or for cleaning electronic components. The consumer product compositions of the invention can have a wide pH range (e.g., about 2 to about 12, or higher), and a wide range of alkalinity reserve. For example, the consumer product compositions of the invention can be used in very high alkalinity reserves, such as drain unblocking, in which tens of grams of NaOH equivalent can be present per 100 grams of formulation. These mixtures can also be used in medium alkalinity reserves having 1 to 10 grams of NaOH equivalent, and mild or low-alkalinity ranges (e.g, liquid hand cleaners; acidic, hard-surface cleaners). Both high-foaming and low-foaming detergent types are encompassed.

Cleaning Components

A cleaning component is a material required to transform a composition containing only the minimum essential ingredients into a composition useful for laundry or cleaning purposes. The cleaning components are easily recognizable to those of skill in the art as being characteristic of laundry or cleaning products. The precise nature of these cleaning components, and levels of incorporation thereof, depends on the physical form of the composition and the nature of the cleaning operation for which it is to be used.

If the cleaning component is used with bleach, it should have good stability. In some embodiments, the cleaning compositions of the invention should be boron-free and/or phosphate-free, as required by legislation. The cleaning component(s) can be present in the cleaning composition in an amount of about 0.001 wt. % to about 99.999 wt. %, typically about 70 wt. % to about 95 wt. %, based on the total weight of the cleaning composition. When used for a particular application, the concentration of the cleaning composition of the invention can vary widely ranging, for example, from a few parts per million solution to direct application of the neat cleaning composition.

Common cleaning components include, for example, a builder, a surfactant, an enzyme, an enzyme stabilizing system, a polymer, bleach, a bleach activator, a catalytic material, a polymeric soil release agent, a clay soil removal/anti-redeposition agent, a polymeric dispersing agent, a brightener, a dyes or a fabric hueing agent, a dye transfer inhibiting agent, a chelating agent, a thickener, a fabric softener, a perfume, an active ingredient, a carrier, a hydrotrope, a processing aid, a dye or a pigment, a solvent for liquid formulations, a solid filler for bar compositions, color speckles, silvercare, an anti-tarnish and/or anti-corrosion agent, a germicide, an alkalinity source, an anti-oxidant, a pro-perfumes, a solubilizing agent, and mixtures thereof.

In some embodiments, the cleaning compositions of the invention (e.g., laundry detergents, laundry detergent additives, hard surface cleaners, synthetic and soap-based laundry bars, fabric softeners and fabric treatment liquids, solids and treatment articles of all kinds) include several cleaning components. In some embodiments, the cleaning compositions of the invention include only one or two cleaning components, such as a bleach additive and a surfactant. A comprehensive list of suitable cleaning components and methods is described in U.S. Pat. No. 6,593,285, incorporated herein by reference.

Builders

Detergent builders selected from aluminosilicates and silicates are can be included in the compositions herein, for example to assist in controlling mineral, especially calcium and/or magnesium hardness in wash water, or to assist in the removal of particulate soils from surfaces. Also suitable for use herein are synthesized crystalline ion exchange materials or hydrates thereof, an anhydride form: $x(M_2O).ySiO_2.zM'O$ wherein M is Na and/or K, M' is Ca and/or Mg; y/x is 0.5 to 2.0 and z/x is 0.005 to 1.0 as taught in U.S. Pat. No. 5,427,711, incorporated herein by reference. Detergent builders in place of or in addition to the silicates and aluminosilicates described hereinbefore can optionally be included in the compositions herein, for example to assist in controlling mineral, especially calcium and/or magnesium hardness in wash water or to assist in the removal of particulate soils from surfaces.

Builder level can vary widely depending upon end use and physical form of the composition. Built detergents typically comprise at least about 1 wt. % builder, based on the total weight of the detergent. Liquid formulations typically comprise about 5 wt. % to about 50 wt. %, more typically 5 wt. % to 35 wt. % of builder to the total weight of the detergent. Granular formulations typically comprise from about 10% to about 80%, more typically 15% to 50% builder by weight of the detergent composition. Lower or higher levels of builders are not excluded. For example, certain detergent additive or high-surfactant formulations can be unbuilt.

Suitable builders herein can be selected from the group consisting of phosphates and polyphosphates, especially the sodium salts; carbonates, bicarbonates, sesquicarbonates and carbonate minerals other than sodium carbonate or sesquicarbonate; organic mono-, di-, tri-, and tetracarboxylates especially water-soluble nonsurfactant carboxylates in acid, sodium, potassium or alkanolammonium salt form, as well as oligomeric or water-soluble low molecular weight polymer carboxylates including aliphatic and aromatic types; and phytic acid. These may be complemented by borates, e.g., for pH-buffering purposes, or by sulfates, especially sodium sulfate and any other fillers or carriers which may be important to the engineering of stable surfactant and/or builder-containing detergent compositions.

Detersive Surfactants

In some embodiments, the cleaning compositions of the invention can further comprise additional surfactants, herein also referred to as co-surfactants. The cleaning composition of the present invention typically comprise about 0.1% to about 55%, preferably from about 0.5% to about 15%, by weight of co-surfactants. (e.g., anionic co-surfactants, nonionic co-surfactants, cationic co-surfactants). It is to be understood that the mixtures of $C_{10}$-$C_{13}$ alkylphenyl sulfonate prepared in the manner of the present invention may be used singly in cleaning compositions or in combination with other detersive surfactants. Typically, fully-formulated cleaning compositions will contain a mixture of surfactant types in order to obtain broad-scale cleaning performance over a variety of soils and stains, and under a variety of usage conditions. One advantage of the $C_{10}$-$C_{13}$ alkylphenyl sulfonates herein is their ability to be readily formulated in combination with other known surfactant types. Nonlimiting examples of additional surfactants which may be used herein typically at levels from about 1% to about 55%, by weight, include the unsaturated sulfates, the $C_{10}$-$C_{18}$ alkyl alkoxy, $C_{10}$-$C_{18}$ alkyl alkoxy carboxylates, the $C_{10}$-$C_{18}$ glycerol ether sulfates, the $C_{10}$-$C_{18}$ alkyl polyglycosides and their corresponding sulfated polyglycosides, and $C_{12}$-$C_{18}$ alpha-sulfonated fatty acid esters. Nonionic surfactants such as the ethoxylated $C_{10}$-$C_{18}$ alcohols and alkyl phenols can also be used. If desired, other conventional surfactants such as the $C_{12}$-$C_{18}$ betaines and sulfobetaines ("sultaines"), $C_{10}$-$C_{18}$ amine oxides, and the like, can also be included in the overall compositions. The $C_{10}$-$C_{18}$ N-alkyl polyhydroxy fatty acid amides can also be used. See WO 9,206,154, incorporated herein by reference. Other sugar-derived surfactants include the N-alkoxy polyhydroxy fatty acid amides. The N-propyl through N-hexyl $C_{12}$-$C_{18}$ glucamides can be used for low sudsing. $C_{10}$-$C_{20}$ conventional soaps may also be used. If high sudsing is desired, the branched-chain $C_{10}$-$C_{16}$ soaps may be used.

A wide range of these co-surfactants can be used in the detergent compositions of the present invention. A typical listing of anionic, nonionic, ampholytic and zwitterionic classes, and species of these co-surfactants, is given in U.S. Pat. No. 3,664,961, incorporated herein by reference. Amphoteric surfactants are also described in detail in "Amphoteric Surfactants, Second Edition", E. G. Lomax, Editor (published 1996, by Marcel Dekker, Inc.), incorporated herein by reference.

Amine-Neutralized Anionic Surfactants

Anionic surfactants of the present invention and adjunct anionic cosurfactants may be neutralized by amines or, preferably, alkanolamines, and alkanolamines are preferred. Suitable non-limiting examples including monoethanolamine, triethanolamine, and other alkanolamines known in the art.

Enzymes

Enzymes can be included in the present cleaning compositions for a variety of purposes, including removal of protein-based, carbohydrate-based, or triglyceride-based stains from substrates, for the prevention of refugee dye transfer in fabric laundering, and for fabric restoration. Suitable enzymes include proteases, amylases, lipases, cellulases, peroxidases, and mixtures thereof of any suitable origin, such as vegetable, animal, bacterial, fungal and yeast origin. Preferred selections are influenced by factors such as pH-activity and/or stability optima, thermostability, and stability to active detergents, builders and the like. In this respect bacterial or fungal enzymes are preferred, such as bacterial amylases and proteases, and fungal cellulases.

Enzymes are normally incorporated into cleaning compositions at levels sufficient to provide a "cleaning-effective amount." The term "cleaning effective amount" refers to any amount capable of producing a cleaning, stain removal, soil removal, whitening, deodorizing, or freshness improving effect on substrates such as fabrics, dishware and the like. In practical terms for current commercial preparations, typical amounts are up to about 5 mg by weight, more typically 0.01 mg to 3 mg, of active enzyme per gram of the consumer product cleaning composition. Stated otherwise, the compositions herein will typically comprise from 0.001% to 5%, preferably 0.01%-1% by weight of a commercial enzyme preparation.

A range of enzyme materials and means for their incorporation into synthetic detergent compositions is disclosed in WO 9307263 A; WO 9307260 A; WO 8908694 A; U.S. Pat. Nos. 3,553,139; 4,101,457; and 4,507,219, each incorporated herein by reference. Enzyme materials useful for liquid detergent formulations, and their incorporation into such formulations, are disclosed in U.S. Pat. No. 4,261,868, incorporated herein by reference.

Enzyme Stabilizing System

Enzymes for use in detergents can be stabilized by various techniques. Enzyme stabilization techniques are disclosed and exemplified in U.S. Pat. Nos. 3,600,319 and 3,519,570; EP 199,405, EP 200,586; and WO 9401532 A, each incorporated herein by reference. Thus, the enzyme-containing compositions herein may optionally also comprise from about 0.001% to about 10%, preferably from about 0.005% to about 8%, most preferably from about 0.01% to about 6%, by weight of an enzyme stabilizing system. The enzyme stabilizing system can be any stabilizing system which is compatible with the detersive enzyme. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, and mixtures thereof, and are designed to address different stabilization problems depending on the type and physical form of the cleaning composition.

Bleaching Compounds, Bleaching Agents, Bleach Activators, and Bleach Catalysts

In some embodiments, the cleaning compositions can further contain bleaching agents or bleaching compositions containing a bleaching agent and one or more bleach activators. Bleaching agents will typically be present at levels of about 1 wt. % to about 30 wt. %, more typically from about 5 wt. % to about 20 wt. %, based on the total weight of the composition, especially for fabric laundering. If present, the amount of bleach activators will typically be about 0.1 wt. % to about 60 wt. %, more typically about 0.5 wt. % to about 40 wt. % of the bleaching composition comprising the bleaching agent-plus-bleach activator.

Examples of bleaching agents include oxygen bleach, perborate bleach, percarboxylic acid bleach and salts thereof, peroxygen bleach, persulfate bleach, percarbonate bleach, and mixtures thereof. Examples of bleaching agents are disclosed in U.S. Pat. No. 4,483,781, U.S. patent application Ser. No. 740,446, European Patent Application 0,133,354, U.S. Pat. No. 4,412,934, and U.S. Pat. No. 4,634,551, each incorporated herein by reference.

Examples of bleach activators (e.g., acyl lactam activators) are disclosed in U.S. Pat. Nos. 4,915,854; 4,412,934; 4,634,551; 4,634,551; and 4,966,723, each incorporated herein by reference.

In some embodiments, a laundry detergent composition comprises a transition metal catalyst. Preferably, the transition metal catalyst may be encapsulated. The transition metal bleach catalyst typically comprises a transition metal ion, preferably selected from transition metal selected from the group consisting of Mn(II), Mn(III), Mn(IV), Mn(V), Fe(II), Fe(III), Fe(IV), Co(I), Co(II), Co(III), Ni(I), Ni(II), Ni(III), Cu(I), Cu(II), Cu(III), Cr(II), Cr(III), Cr(IV), Cr(V), Cr(VI), V(III), V(IV), V(V), Mo(IV), Mo(V), Mo(VI), W(IV), W(V), W(VI), Pd(II), Ru(II), Ru(III), and Ru(IV), more preferably Mn(II), Mn(III), Mn(IV), Fe(II), Fe(III), Cr(II), Cr(III), Cr(IV), Cr(V), and Cr(VI). The transition metal bleach catalyst typically comprises a ligand, preferably a macropolycyclic ligand, more preferably a cross-bridged macropolycyclic ligand. The transition metal ion is preferably coordinated with the ligand. Preferably, the ligand comprises at least four donor atoms, at least two of which are bridgehead donor atoms. Suitable transition metal bleach catalysts are described in U.S. Pat. No. 5,580,485, U.S. Pat. No. 4,430,243; U.S. Pat. No. 4,728,455; U.S. Pat. No. 5,246,621; U.S. Pat. No. 5,244,594; U.S. Pat. No. 5,284,944; U.S. Pat. No. 5,194,416; U.S. Pat. No. 5,246,612; U.S. Pat. No. 5,256,779; U.S. Pat. No. 5,280,117; U.S. Pat. No. 5,274,147; U.S. Pat. No. 5,153,161; U.S. Pat. No. 5,227,084; U.S. Pat. No. 5,114,606; U.S. Pat. No. 5,114,611, EP 549,271 A1; EP 544,490 A1; EP 549,272 A1; and EP 544,440 A2, each incorporated herein by reference. A suitable transition metal bleach catalyst is a manganese-based catalyst, for example disclosed in U.S. Pat. No. 5,576,282, incorporated herein by reference. Suitable cobalt bleach catalysts are described, for example, in U.S. Pat. No. 5,597,936 and U.S. Pat. No. 5,595,967, each incorporated herein by reference. Such cobalt catalysts are readily prepared by known procedures, such as taught for example in U.S. Pat. No. 5,597,936, and U.S. Pat. No. 5,595,967, each incorporated herein by reference. A suitable transition metal bleach catalyst is a transition metal complex of ligand such as bispidones described in WO 05/042532 A1, incorporated herein by reference.

Bleaching agents other than oxygen bleaching agents are also known in the art and can be utilized herein (e.g., photoactivated bleaching agents such as the sulfonated zinc and/or aluminum phthalocyanines (U.S. Pat. No. 4,033,718, incorporated herein by reference), or pre-formed organic peracids, such as peroxycarboxylic acid or salt thereof, or a peroxysulphonic acid or salt thereof. A suitable organic peracid is phthaloylimidoperoxycaproic acid. If used, consumer product cleaning compositions will typically contain from about 0.025% to about 1.25%, by weight, of such bleaches, especially sulfonate zinc phthalocyanine.

Polymeric Soil Release Agent

Known polymeric soil release agents, hereinafter "SRA" or "SRA's", can optionally be employed in the present cleaning compositions. If utilized, SRA's will generally comprise about 0.01% to about 10.0%, typically about 0.1% to about 5%, preferably about 0.2% to about 3.0% by weight, of the composition.

Preferred SRA's typically have hydrophilic segments to hydrophilize the surface of hydrophobic fibers, such as polyester and nylon, and hydrophobic segments to deposit upon hydrophobic fibers and remain adhered thereto through completion of washing and rinsing cycles, thereby serving as an anchor for the hydrophilic segments. This can enable stains occurring subsequent to treatment with SRA to be more easily cleaned in later washing procedures.

SRA's can include, for example, a variety of charged, e.g., anionic or even cationic (see U.S. Pat. No. 4,956,447, incorporated herein by reference), as well as noncharged monomer units, and structures may be linear, branched or even star-shaped. They may include capping moieties which are especially effective in controlling molecular weight or altering the physical or surface-active properties. Structures and charge distributions may be tailored for application to different fiber or textile types and for varied detergent or detergent additive products. Examples of SRAs are described in U.S. Pat. Nos. 4,968,451; 4,711,730; 4,721,580; 4,702,857; 4,877,896; 3,959,230; 3,893,929; 4,000,093; 5,415,807; 4,201,824; 4,240,918; 4,525,524; 4,201,824; 4,579,681; and 4,787,989; European Patent Application 0 219 048; 279,134 A; 457,205 A; and DE 2,335,044, all of which are incorporated herein by reference.

Clay Soil Removal/Anti-Redeposition Agents

The compositions of the present invention can also optionally contain water-soluble ethoxylated amines having clay soil removal and antiredeposition properties. Granular detergent compositions which contain these compounds typically contain about 0.01% to about 10.0%, by weight, of the water-soluble ethoxylates amines; liquid detergent compositions typically contain about 0.01% to about 5% by weight of these compounds.

Exemplary clay soil removal and antiredeposition agents are described in U.S. Pat. Nos. 4,597,898; 548,744; 4,891, 160; European Patent Application Nos. 111,965; 111,984; 112,592; and WO 95/32272, which are all incorporated herein by reference.

Polymeric Dispersing Agents

Polymeric dispersing agents can advantageously be utilized at levels of about 0.1% to about 7%, by weight, in the compositions herein, especially in the presence of zeolite and/or layered silicate builders. Suitable polymeric dispersing agents include polymeric polycarboxylates and polyethylene glycols, although others known in the art can also be used. It is believed, though it is not intended to be limited by theory, that polymeric dispersing agents enhance overall detergent builder performance, when used in combination with other builders (including lower molecular weight polycarboxylates) by crystal growth inhibition, particulate soil release peptization, and anti-redeposition. Examples of polymeric dispersing agents are found in U.S. Pat. No. 3,308,067, European Patent Application No. 66915, EP 193,360, and EP 193,360, each incorporated herein by reference.

Alkoxylated Polyamines

Soil suspension, grease cleaning, and particulate cleaning polymers may include the alkoxylated polyamines Such materials include but are not limited to ethoxylated polyethyleneimine, ethoxylated hexamethylene diamine, and sulfated versions thereof. A useful example is 600 g/mol polyethyleneimine core ethoxylated to 20 EO groups per NH and is available from BASF.

Brightener

Any optical brighteners or other brightening or whitening agents known in the art can be incorporated at levels typically of about 0.01% to about 1.2%, by weight, into the cleaning compositions herein. Commercial optical brighteners which may be useful in the present invention can be classified into subgroups, which include, but are not necessarily limited to, derivatives of stilbene, pyrazoline, coumarin, carboxylic acid, methinecyanines, dibenzothiophene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982), incorporated herein by reference. Specific examples of optical brighteners which are useful in the present compositions are those identified in U.S. Pat. No. 4,790,856 and U.S. Pat. No. 3,646,015, each incorporated herein by reference.

Fabric Hueing Agents

The compositions of the present invention my include fabric hueing agents. Non-limiting examples include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof. In another aspect, suitable polymeric dyes include polymeric dyes selected from the group consisting of fabric-substantive colorants sold under the name of LIQUITINT® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of LIQUITINT t® (Milliken, Spartanburg, S.C., USA) Violet CT, carboxymethyl cellulose (CMC) conjugated with a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

Dye Transfer Inhibiting Agents

The compositions of the present invention may also include one or more materials effective for inhibiting the transfer of dyes from one fabric to another during the cleaning process. Generally, such dye transfer inhibiting agents include polyvinyl pyrrolidone polymers, polyamine N-oxide polymers, copolymers of N-vinylpyrrolidone and N-vinylimidazole, manganese phthalocyanine, peroxidases, and mixtures thereof. If used, these agents typically comprise about 0.01% to about 10% by weight of the composition, preferably from about 0.01% to about 5%, and more preferably from about 0.05% to about 2%.

Chelating Agents

The detergent compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein. If utilized, these chelating agents will generally comprise about 0.1% to about 15% by weight of the detergent compositions herein. More preferably, if utilized, the chelating agents will comprise from 0.1% to about 3.0% by weight of such compositions.

Structurant/Thickeners

Structured liquids can either be internally structured, whereby the structure is formed by primary ingredients (e.g. surfactant material) and/or externally structured by providing a three dimensional matrix structure using secondary ingredients (e.g. polymers, clay and/or silicate material). The composition may comprise a structurant in an amount of about 0.01 wt. % to 5 wt. %, preferably about 0.1 wt. % to 2.0 wt. %, based on the total weight of the composition. The structurant is typically selected from the group consisting of diglycerides and triglycerides, ethylene glycol distearate, microcrystalline cellulose, cellulose-based materials, microfiber cellulose, biopolymers, xanthan gum, gellan gum, and mixtures thereof. A suitable structurant includes hydrogenated castor oil, and non-ethoxylated derivatives thereof. A suitable structurant is disclosed in U.S. Pat. No. 6,855,680, incorporated herein by reference. Such structurants have a thread-like structuring system having a range of aspect ratios. Other suitable structurants and the processes for making them are described in WO2010/034736, incorporated herein by reference.

Alkoxylated Polycarboxylates

Alkoxylated polycarboxylates, such as those prepared from polyacrylates, are useful herein to provide additional grease removal performance. Such materials are described in WO 91/08281 and PCT 90/01815, incorporated herein by reference. Chemically, these materials comprise polyacrylates having one ethoxy side-chain per every 7-8 acrylate units. The side-chains are of the formula —$(CH_2CH_2O)_m(CH_2)_nCH_3$ wherein m is 2-3 and n is 6-12. The side-chains are ester-linked to the polyacrylate "backbone" to provide a "comb" polymer type structure. The molecular weight can vary, but is typically in the range of about 2000 to about 50,000. Such alkoxylated polycarboxylates can comprise about 0.05% to about 10%, by weight, of the compositions herein.

Amphiphilic Graft Co-Polymer

The mixtures of $C_{10}$-$C_{13}$ alkylphenylsulfonates of the present invention, and their mixtures with other cosurfactants and other adjunct ingredients, can be used with an amphilic graft co-polymer, preferably the amphilic graft co-polymer comprises (i) polyethyelene glycol backbone; and (ii) and at least one pendant moiety selected from polyvinyl acetate, polyvinyl alcohol and mixtures thereof. A preferred amphilic graft co-polymer is Sokalan HP22, supplied from BASF.

Fabric Softeners

Various through-the-wash fabric softeners, especially the impalpable smectite clays of U.S. Pat. No. 4,062,647, incorporated herein by reference, as well as other softener clays known in the art, can optionally be used typically at levels of about 0.5% to about 10%, by weight in the present compositions to provide fabric softener benefits concurrently with fabric cleaning. Clay softeners can be used in combination with amine and cationic softeners as disclosed, for example, in U.S. Pat. No. 4,375,416, and U.S. Pat. No. 4,291,071, which are incorporated herein by reference.

Perfumes

Perfumes and perfumery ingredients useful in the present compositions and processes comprise a wide variety of natural and synthetic chemical ingredients, including, but not limited to, aldehydes, ketones, esters, and the like. Also included are various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. Finished perfumes typically comprise about 0.01% to about 2%, by weight, of the detergent compositions herein, and individual lay softeners can be used in combination with amine and cationic softeners perfumery ingredients can comprise about 0.0001% to about 90%, by weight, of a finished perfume composition.

Other Ingredients

A wide variety of other ingredients useful in the cleaning compositions can be included in the compositions herein, including other active ingredients, carriers, hydrotropes, processing aids, dyes or pigments, solvents for liquid formulations, solid fillers for bar compositions, etc. If high sudsing is desired, suds boosters such as the $C_{10}$-$C_{16}$ alkanolamides can be incorporated into the compositions, typically at 1%-10% levels. The $C_{10}$-$C_{13}$ monoethanol and diethanol amides illustrate a typical class of such suds boosters. Use of such suds boosters with high sudsing adjunct surfactants such as the amine oxides, betaines and sultaines noted above is also advantageous. If desired, water-soluble magnesium and/or calcium salts such as $MgCl_2$, $MgSO_4$, $CaCl_2$, $CaSO_4$ and the like, can be added at levels of, typically, 0.1%-2%, to provide additional suds and to enhance grease removal performance.

Various detersive ingredients employed in the present compositions optionally can be further stabilized by absorbing said ingredients onto a porous hydrophobic substrate, then coating said substrate with a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

Liquid detergent compositions can contain water and other solvents as carriers. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from 5% to 90%, typically 10% to 50% by weight of such carriers.

The cleaning compositions herein will preferably be formulated such that, during use in aqueous cleaning operations, the wash water will have a pH of between about 6.5 and about 11, preferably between about 7.5 and 10.5. Liquid dishwashing product formulations preferably have a pH between about 6.8 and about 9.0. Laundry products are typically at pH 9-11. Techniques for controlling pH at recommended usage levels include the use of buffers, alkalis, acids, etc., and are well known to those skilled in the art.

Form of the Compositions

The compositions in accordance with the invention can take a variety of physical forms including granular, tablet, bar and liquid forms. Also included are a sachet, a two-in-one pouch containing both solid and liquid compartments. The compositions can be the so-called concentrated granular detergent compositions adapted to be added to a washing machine by means of a dispensing device placed in the machine drum with the soiled fabric load.

The mean particle size of the components of granular compositions in accordance with the invention should preferably be such that no more that 5% of particles are greater than 1.7 mm in diameter and not more than 5% of particles are less than 0.15 mm in diameter.

The term mean particle size as defined herein is calculated by sieving a sample of the composition into a number of fractions (typically 5 fractions) on a series of Tyler sieves. The weight fractions thereby obtained are plotted against the aperture size of the sieves. The mean particle size is taken to be the aperture size through which 50% by weight of the sample would pass.

The bulk density of granular detergent compositions in accordance with the present invention typically have a bulk density of at least 600 g/liter, more preferably from 650 g/liter to 1200 g/liter. Bulk density is measured by means of a simple funnel and cup device consisting of a conical funnel moulded rigidly on a base and provided with a flap valve at its lower extremity to allow the contents of the funnel to be emptied into an axially aligned cylindrical cup disposed below the funnel. The funnel is 130 mm high and has internal diameters of 130 mm and 40 mm at its respective upper and lower extremities. It is mounted so that the lower extremity is 140 mm above the upper surface of the base. The cup has an overall height of 90 mm, an internal height of 87 mm and an internal diameter of 84 mm. Its nominal volume is 500 mm.

To carry out a measurement, the funnel is filled with powder by hand pouring, the flap valve is opened and powder allowed to overfill the cup. The filled cup is removed from the frame and excess powder removed from the cup by passing a straight edged implement eg; a knife, across its upper edge. The filled cup is then weighed and the value obtained for the weight of powder doubled to provide a bulk density in g/L. Replicate measurements are made as required.

Surfactant Agglomerate Particles

One of the preferred methods of delivering surfactant in consumer products is to make surfactant agglomerate particles, which may take the form of flakes, prills, marumes, noodles, ribbons, but preferably take the form of granules. A preferred way to process the particles is by agglomerating powders (e.g. aluminosilicate, carbonate) with high active surfactant pastes and to control the particle size of the resultant agglomerates within specified limits. Such a process involves mixing an effective amount of powder with a high active surfactant paste in one or more agglomerators such as a pan agglomerator, a Z-blade mixer, or more preferably an in-line mixer, such as those manufactured by Schugi (Holland) BV, 29 Chroomstraat 8211 AS, Lelystad, Netherlands, and Gebruder Lödige Maschinenbau GmbH, D-4790 Paderborn 1, Elsenerstrasse 7-9, Postfach 2050, Germany. Most preferably a high shear mixer is used, such as a Lödige CB (Trade Name).

A high active surfactant paste comprising about 50 wt. % to about 95 wt. %, preferably about 70 wt. % to about 85 wt. % of surfactant is typically used. The paste may be pumped into the agglomerator at a temperature high enough to maintain a pumpable viscosity, but low enough to avoid degradation of the anionic surfactants used. A typical operating temperature of the paste includes about 50° C. to about 80° C.

Compacted Liquid or Powder Detergents

The mixtures of the alkylphenyl sulfonates of the invention, and their mixtures with other cosurfactants and other adjunct ingredients, are suited to compact detergent formulations. For liquid detergents, the composition preferably comprises less than about 20 wt. %, or less than about 10 wt. %, or less than about 5 wt. %, or less than about 4 wt. % or less than about 3 wt. % free water, or less than about 2 wt. % free water, or less than about 1 wt. % free water, and may even be anhydrous, typically comprising no deliberately added free water. Free water is typically measured using Karl Fischer titration. The laundry detergent composition (e.g., 2 g) is extracted into 50 mL of dry methanol at room temperature for about 20 minutes and about 1 mL of the solution is analyzed by Karl Fischer titration. For powder detergents, the amount of filler (e.g., sodium sulfate, sodium chloride, clay, or other inert solid ingredients) preferably comprises less than about 20 wt. %, or less than about 10 wt. %, or less than about 5 wt. %, or less than about 4 wt. % or less than about 3 wt. % free water, or less than about 2 wt. % free water, or less than about 1 wt. % filler.

Laundry Washing Method

In some embodiments, the invention provides a method of laundering soiled fabrics comprising contacting the soiled fabrics with an effective amount of a detergent composition described herein.

Machine laundry methods herein typically comprise treating soiled laundry with an aqueous wash solution in a washing machine having dissolved or dispensed therein an effective amount of a machine laundry detergent composition in accord with the invention. By an effective amount of the detergent composition it is meant from 20 g to 300 g of product dissolved or dispersed in a wash solution of volume from 5 to 65 liters, as are typical product dosages and wash solution volumes commonly employed in conventional machine laundry methods.

As noted, the mixtures of alkylphenyl sulfonates having particular distributions are used herein in cleaning compositions, preferably in combination with other detersive surfactants, at levels which are effective for achieving at least a directional improvement in cleaning performance. In the context of a fabric laundry composition, such "usage levels" can vary depending not only on the type and severity of the soils and stains, but also on the wash water temperature, the volume of wash water and the type of washing machine (e.g., top-loading, front-loading, top-loading, vertical-axis Japanese-type automatic washing machine)

As can be seen from the foregoing, the mixtures of alkylphenyl sulfonates having particular distributions used in a machine-wash laundering context can vary, depending on the habits and practices of the user, the type of washing machine, and the like. In this context, however, one heretofore unappreciated advantage of the mixtures of alkylphenyl sulfonates having particular distributions is their ability to provide at least directional improvements in performance over a spectrum of soils and stains, even when used at relatively low levels with respect to the other surfactants (generally anionics or anionic/nonionic mixtures) in the finished compositions.

In addition, another advantage of the mixtures of alkylphenyl sulfonates having particular distributions and the detergent compositions containing them is their desirable performance in cold water. The invention herein includes methods for laundering of fabrics at reduced wash temperatures. This method of laundering fabric comprises the step of contacting a laundry detergent composition to water to form a wash liquor, and laundering fabric in said wash liquor, wherein the wash liquor has a temperature of above 0° C. to 20° C., preferably to 19° C., or to 18° C., or to 17° C., or to 16° C., or to 15° C., or to 14° C., or to 13° C., or to 12° C., or to 11° C., or to 10° C., or to 9° C., or to 8° C., or to 7° C., or to 6° C., or even to 5° C. The fabric may be contacted to the water prior to, or after, or simultaneous with, contacting the laundry detergent composition with water.

A further method of use of the materials of the present invention involves pretreatment of stains prior to laundering.

Hand Machine Dishwashing Methods

Any suitable methods for machine washing or cleaning soiled tableware, particularly soiled silverware are envisaged.

A preferred liquid hand dishwashing method involves either the dissolution of the detergent composition into a receptacle containing water, or by the direct application of the liquid hand dishwashing detergent composition onto soiled dishware.

A preferred machine dishwashing method comprises treating soiled articles selected from crockery, glassware, hollowware, silverware and cutlery and mixtures thereof, with an aqueous liquid having dissolved or dispensed therein an effective amount of a machine dishwashing composition in accord with the invention. By an effective amount of the machine dishwashing composition it is meant from 8 g to 60 g of product dissolved or dispersed in a wash solution of volume from 3 to 10 liters, as are typical product dosages and wash solution volumes commonly employed in conventional machine dishwashing methods.

Cleansing Hard Surfaces

Any suitable methods for cleaning hard surfaces, such as wood, ceramic, glass, marble, porcelain, grout or concrete using the compositions described herein are envisaged. In some embodiments, an effective amount of a detergent composition of the invention is directly applied to the hard surface.

Packaging for the Compositions

Commercially marketed executions of the bleaching compositions can be packaged in any suitable container including those constructed from paper, cardboard, plastic materials and any suitable laminates. A preferred packaging execution is described in European Application No. 94921505.7, incorporated herein by reference.

Personal Care Compositions

Personal care compositions, which can be aqueous or anhydrous, are described in European Patent No. 1299080, U.S. Patent Application Publication No. 2009/0232873, and U.S. Pat. No. 5,932,202. Nonlimiting examples of personal care products include those intended for use with hair or skin such as a shampoo, a hair conditioner, a hair treatment, a facial soap, a body wash, a body soap (liquid or bar), a foam bath, a make-up remover, a skin care product, an acne control product, a deodorant, an antiperspirant, a shaving aid, a cosmetic, a depilatory, a fragrance, special purpose cleaners and mixtures thereof. See, e.g., WO 96/37595A; WO 96/37592A; WO 96/37591A; WO 96/37589A; WO 96/37588A; GB 2,297,975A; GB 2,297,762A; GB 2,297,761A; WO 96/17916A; WO 96/12468A, each incorporated herein by reference. Personal care cleaning compositions can be formulated into, for example, a wipe, a cloth, a bar, a liquid, a powder, a crème, a lotion, a spray, an aerosol, a foam, a mousse, a serum, a capsule, a gel, an emulsion, a doe foot, a roll-on applicator, a stick, a sponge, an ointment, a paste, an emulsion spray, a tonic, a cosmetic, and mixtures thereof. Products, such as devices, appliances, applicators, implements, combs, brushes, and substrates are also encompassed by the invention. These products can be used alone on the skin or hair, or in combination with the personal care cleaning compositions described herein.

The personal care product of the invention can be applied by hand in unitary or freely alterable dosage, or by automatic dispensing means. The personal care composition of the invention also can be dispensed from an article, such as, for example, a bottle, a jar, a tube, a sachet, a pouch, a container, a tottle, a vial, an ampule, or a compact, or can be integrally contained within a delivery form, such as a wipe.

In some preferred embodiments, the personal care compositions of the present invention may be used in direct application to the skin or in a conventional manner for cleansing, treating or conditioning skin and hair. The compositions herein are useful for cleansing or conditioning the hair and scalp, and other areas of the body and for any other area of skin in need of treatment. The present invention may be used for treating, cleansing, or conditioning of the skin or hair of animals as well. An effective amount of the composition, typically from about 1 g to about 50 g, preferably from about 1 g to about 20 g of the composition, for cleansing and/or conditioning hair, skin or other area of the body, is topically applied to the hair, skin or other area that has preferably been wetted, generally with water, and then rinsed off. Application to the hair typically includes working the composition through the hair.

Personal Care Components

A personal care component is a material required to transform a composition containing only the minimum essential ingredients into a composition useful for personal care purposes. The personal care components are easily recognizable to those of skill in the art as being characteristic of personal care products. The precise nature of these personal care components, and levels of incorporation thereof, depends on the physical form of the composition and the nature of the personal care operation for which it is to be used The personal component(s) can be present in the personal care composition in an amount of about 0.001 wt. % to about 99.999 wt. %, typically about 70 wt. % to about 95 wt. %, based on the total weight of the personal care composition. When used for a particular application, the concentration of the personal care composition of the invention can vary widely ranging, for example, from a few parts per million solution to direct application of the personal care composition.

Common personal care components include, for example, an oil, an emollient, a moisturizer, a carrier, an extract, a vitamin, a mineral, an anti-aging compound, a surfactant, a solvent, a polymer, a preservative, an antimicrobial, a wax, a particle, a colorant, a dye, a fragrance, and mixtures thereof. In some embodiments, the personal care compositions of the invention (e.g.,) include several personal care components. In some embodiments, the personal care compositions include only one or two personal components, such as a detersive surfactant and a hair conditioning active. Lists of personal care components and methods are described in U.S. Patent Application No. 2007/002022 and U.S. Pat. No. 5,932,202, incorporated herein by reference.

In some embodiments, the personal care composition of the present invention further includes a detersive surfactant. The detersive surfactant component is included to provide improved cleaning performance to the composition. The detersive surfactant component in turn comprises anionic detersive surfactant, zwitterionic or amphoteric detersive surfactant, or a combination thereof. Such surfactants should be physically and chemically compatible with the essential components described herein, or should not otherwise unduly impair product stability, aesthetics or performance.

Suitable anionic detersive surfactant components for use in the personal care composition herein include those which are known for use in hair care or other personal care cleansing compositions. The concentration of the anionic surfactant component in the composition should be sufficient to provide the desired cleaning and lather performance, and generally range from about 5 wt. % to about 50 wt. %, preferably from about 8 wt. % to about 30 wt. %, more preferably from about 10 wt. % to about 25 wt. %, even more preferably from about 12 wt. % to about 22 wt. %, based on the total weight of the personal care composition.

Preferred anionic surfactants suitable for use in the personal care composition are the alkyl and alkyl ether sulfates. These materials have the respective formulae $ROSO_3M$ and $RO(C_2H_4O)_xSO_3M$, wherein R is alkyl or alkenyl of about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium.

Preferably, R has about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with about 0 to about 10, preferably about 2 to about 5, more preferably about 3, molar proportions of ethylene oxide, and the resulting mixture of molecular species having, for example, an average of 3 moles of ethylene oxide per mole of alcohol, is sulfated and neutralized.

Other suitable anionic detersive surfactants are the water-soluble salts of organic, sulfuric acid reaction products conforming to the formula $[R^1—SO_3\text{-}M]$ where $R^1$ is a straight or branched chain, saturated, aliphatic hydrocarbon radical having about 8 to about 24, preferably about 10 to about 18, carbon atoms; and M is a cation described hereinbefore.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278.

Other anionic detersive surfactants suitable for use in the compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic detersive surfactants include alkene sulfonates having about 10 to about 24 carbon atoms. In addition to the true alkene sulfonates and a proportion of hydroxy-alkanesulfonates, the alkene sulfonates can contain minor amounts of other materials, such as alkene disulfonates depending upon the reaction conditions, proportion of reactants, the nature of the starting alkenes and impurities in the alkene stock and side reactions during the sulfonation process. A nonlimiting example of such an alpha-alkene sulfonate mixture is described in U.S. Pat. No. 3,332,880, incorporated herein by reference.

Another class of anionic detersive surfactants suitable for use in the compositions are the beta-alkyloxy alkane sulfonates. These surfactants conform to the formula:

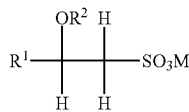

where $R^1$ is a straight chain alkyl group having about 6 to about 20 carbon atoms, $R^2$ is a lower alkyl group having about 1 to about 3 carbon atoms, preferably 1 carbon atom, and M is a water-soluble cation as described hereinbefore.

Preferred anionic detersive surfactants for use in the compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof.

Suitable amphoteric or zwitterionic detersive surfactants for use in the composition herein include those which are known for use in hair care or other personal care cleansing. Concentration of such amphoteric detersive surfactants preferably are about 0.5 wt. % to about 20 wt. %, preferably about 1 wt. % to about 10 wt. %. Nonlimiting examples of suitable zwitterionic or amphoteric surfactants are described in U.S. Pat. Nos. 5,104,646 and 5,106,609, each incorporated herein by reference.

Amphoteric detersive surfactants suitable for use in the composition are well known in the art, and include those surfactants broadly described as derivatives of aliphatic secondary and tertiary amines in which the aliphatic radical can be straight or branched chain and wherein one of the aliphatic substituents contains about 8 to about 18 carbon atoms and one contains an anionic group such as carboxy, sulfonate, sulfate, phosphate, or phosphonate. Preferred amphoteric detersive surfactants for use in the present invention include cocoamphoacetate, cocoamphodiacetate, lauroamphoacetate, lauroamphodiacetate, and mixtures thereof.

Zwitterionic detersive surfactants suitable for use in the composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred.

The personal care compositions of the present invention may further comprise additional surfactants for use in combination with the anionic detersive surfactant component described hereinbefore. Suitable optional surfactants include nonionic and cationic surfactants. Any such surfactant known in the art for use in hair or personal care products may be used, provided that the optional additional surfactant is also chemically and physically compatible with the essential components of the composition, or does not otherwise unduly impair product performance, aesthetics or stability. The concentration of the optional additional surfactants in the composition may vary with the cleansing or lather performance desired, the optional surfactant selected, the desired product concentration, the presence of other components in the composition, and other factors well known in the art.

Nonlimiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; and 2,528,378, each incorporated herein by reference.

The personal care compositions of the present invention can be useful for cleaning and treating a number of mammalian keratinous tissue conditions. Such treatment of keratinous tissue conditions can include prophylactic and therapeutic regulation. More specifically, such treatment methods can be directed to, but are not limited to, preventing, retarding, and/or treating uneven skin tone, reducing the size of pores in mammalian skin, regulating oily/shiny appearance of mammalian skin, thickening keratinous tissue (i.e., building the epidermis and/or dermis and/or subcutaneous layers of the skin and where applicable the keratinous layers of the nail and hair shaft), preventing, retarding, and/or treating uneven skin tone by acting as a lightening or pigmentation reduction cosmetic agent, preventing, retarding, and/or treating atrophy of mammalian skin, softening and/or smoothing lips, hair and nails of a mammal, preventing, retarding, and/or treating itch of mammalian skin, preventing, retarding, and/or treating the appearance of dark under-eye circles and/or puffy eyes, preventing, retarding, and/or treating sallowness of mammalian skin, preventing, retarding, and/or treating sagging (i.e., glycation) of mammalian skin, preventing and/or retarding tanning of mammalian skin, desquamating, exfoliating, and/or increasing turnover in mammalian skin, preventing, retarding, and/or treating hyperpigmentation such as post-inflammatory hyperpigmentation, preventing, retarding, and/or treating the appearance of spider vessels and/or red blotchiness on mammalian skin, preventing, retarding, and/or treating fine lines and wrinkles of mammalian skin, preventing, retarding, and/or treating skin dryness (i.e., roughness, scaling, flaking) and preventing, retarding, and/or treating the appearance of cellulite in mammalian skin. In a preferred embodiment, the personal care composition is used to treat the signs of aging; in one aspect, the composition is used to regulate the signs of aging; in another aspect, the composition is used to reduce or decrease the signs of aging; in yet another aspect the composition is used to prevent the signs of aging in keratinous tissue (e.g., skin, hair, or nails).

For example, the personal care composition can be useful for therapeutically regulating visible and/or tactile discontinuities in mammalian keratinous tissue, including discontinuities in skin texture and color. In some embodiments, the personal care composition can decrease the apparent diameter of pore. In some embodiments, the apparent height of tissue immediately proximate to pore openings can approach that of the interadnexal skin. In other embodiments, the skin tone/color can become more uniform, and/or the length, depth, and/or other dimension of lines and/or wrinkles can be decreased.

Furthermore, the personal care compositions of the present invention can also be useful for cleansing (e.g. hair, body, facial), improving keratinous tissue feel (wet & dry) such as for hair (e.g., improving appearance/look, detangling, shine, gloss, decrease coefficient of friction, increase smoothness, color retention, decrease split ends, prevent hair breakage, prevent environmental damage such as sunlight damage, smoke damage, and damage from pollutants such as nitrogen oxides, sulfur oxides, ozone, and metals such as lead), odor control, oil control, conditioning, hair volume control, hair growth, and hair growth inhibition.

Regulating keratinous tissue conditions can involve topically applying to the keratinous tissue a safe and effective amount of a personal care composition of the present invention. The amount of the composition that is applied, the frequency of application, and the period of use will vary widely depending upon the level of components of a given composition and the level of regulation desired, e.g., in view of the level of keratinous tissue damage present or expected to occur.

Furthermore, regulating keratinous tissue conditions can involve orally ingesting a safe and effective amount of a composition of the present invention. The amount of the composition that is ingested, the frequency of ingestion, and the period of use will vary widely depending upon the level of components of a given composition and the level of regulation desired, e.g., in view of the level of keratinous tissue damage present or expected to occur.

In one embodiment, the personal care composition is chronically applied to the skin, e.g. topically. By "chronic application" is meant continued topical application of the composition over an extended period during the subject's lifetime, preferably for a period of at least about one week, more preferably for a period of at least about one month, even more preferably for at least about three months, even more preferably for at least about six months, and more preferably still for at least about one year. While benefits are obtainable after various maximum periods of use (e.g., five, ten or twenty years), it is preferred that chronic applications continue throughout the subject's lifetime. Typically applications would be on the order of about once per day over such extended periods; however, application rates can vary, and can include from about once per week up to about three times per day or more.

Treating keratinous tissue condition can be practiced, for example, by applying a composition in the form of a skin lotion, clear lotion, milky lotion, cream, gel, foam, ointment, paste, emulsion, spray, aerosol, conditioner, tonic, cosmetic, lipstick, foundation, nail polish, after-shave, roll-on or deodorant stick, powder, oil or the like which is intended to be left on the skin or rinsed off. Any part of the external portion of the face, hair, and/or nails can be treated, (e.g., face, lips, under-eye area, eyelids, scalp, neck, torso, arms, hands, legs, feet, fingernails, toenails, scalp hair, eyelashes, eyebrows, etc.)

EXAMPLES

Example 1a

Synthesis of a Mixture of $C_{10}$-$C_{13}$ Alkenes Having a Bimodal Distribution with an Average Number of Carbon Atoms of 10.9 Via Alkene Metathesis The metathesis synthesis procedure of US 2010/0145086A1 was followed using 1-butene and soybean oil methylester as the starting materials to provide a mixture of $C_{10}$ and $C_{12}$ alkenes that have a bimodal distribution after simple distillation. The ratio of $C_{10}$ and $C_{12}$ alkenes in the product was about 1.28 to about 1.00, corresponding to a chain average of about 10.9.

Example 1b

Synthesis of a Mixture of $C_{10}$-$C_{13}$ Alkylbenzenes Having a Biomodal Distribution with an Average Number of Carbon Atoms of 10.9

The mixture of $C_{10}$ and $C_{12}$ alkenes from Example 1a is alkylated using any of the procedures in known in the art, such as, Alul et al., J. Org. Chem., 32(11):3365-3369 (1967).

Example 1c

Synthesis of a Mixture of Alkyl Benzene Sulfonates of C10-C13 Chain Lengths Having a Biomodal Distribution with an Average Number of Carbon Atoms of 10.9

The mixture of $C_{10}$ and $C_{12}$ alkylbenzenes from Example 1b was sulfonated using following procedure.

The molecular weight of the alkylbenzene was determined by proton nuclear magnetic resonance. A measured amount of alkylbenzene was placed into an NMR tube along with a measured amount of dimethyl carbonate (DMC). The amount of DMC was calculated to provide approximately the same molar quantity of protons as the phenyl protons on the alkylbenzene. The molar quantity of the phenyl protons was determined by comparing the integrations of the alkylbenzene and the DMC. The grams of alkylbenzene per mole of phenyl groups was determined, followed by the molecular weight, which was 237.6. The alkylbenzene should contain less than 1000 ppm of water. If the alkylbenzene contains greater than 1000 ppm of water, it should be dried over 4 Å molecular sieves over night prior to sulfonation. The sieves can be obtained from any chemical catalog such as Aldrich.

The alkylbenzene (8.5 g) was placed in a dry, 3-neck, round-bottom flask with magnetic stirring and a thermometer. Anhydrous methylene chloride (about 40 mL) was added to the flask. The mixture is placed into a cooling bath of ice water/NaCl/ethanol and allowed to cool to about −5° C. A dry addition funnel is charged with chlorosulfonic acid (1.03 equivalents relative to the alkylbenzene), and the HCl that is generated is scrubbed with a trap containing 1N NaOH. Chlorosulfonic acid is dripped into the flask at a rate that does not allow the temperature of the mix to exceed 10° C. After all chlorosulfonic acid was added, the mixture was stirred at −5° C. for about 1 h and then allowed to warm to room temperature. The resulting mixture was transferred to a one-neck round bottom flask and rotavaped (about 40° C.) to remove $CH_2Cl_2$/HCl.

The resulting mixture was placed in a plastic bottle with about 80 mL of methanol and chilled. The mixture was stirred while about 1.08 equivalents of 25% sodium methoxide was added. The mixture was then rotovaped to result in a viscous, oily residue. The residue was dissolved in 300 mL of warm water and freeze dried. The final surfactant was collected from the freeze drier. It was a light, tacky material that can be compressed into a gum-like consistency.

Example 2a

Synthesis of a Mixture of $C_{10}$-$C_{13}$ Alkenes Having a Random Distribution with an Average Number of Carbon Atoms of 12.2-12.3 Via Alkene Metathesis The metathesis synthesis procedure of US 2010/0145086A1 was followed using oleic acid, 2-butene (0.19 mol equiv.), 3-hexene (0.41 mol equiv.), and 4-octene (0.40 mol equiv.) as the starting materials to provide a mixture of $C_{11}$ and $C_{13}$ alkenes that has a random distribution and an average number of total carbon atoms of 12.2-12.3 after simple distillation.

| Chain Length | Commercial Mixture (wt. %) | Inventive Mixture (wt. %) |
| --- | --- | --- |
| 10 | 9.3 | 0 |
| 11 | 21.0 | 17.1 |
| 12 | 25.6 | 40.3 |
| 13 | 30.7 | 42.6 |
| 14 | 13.5 | 0 |

Example 2b

Synthesis of a Mixture of $C_{10}$-$C_{13}$ Alkylbenzenes Having a Random Distribution with an Average Number of Carbon Atoms of 12.2-12.3

The mixture of alkenes from Example 2a is alkylated using any of the procedures in known in the art, such as, Alul et al., J. Org. Chem., 32(11):3365-3369 (1967).

Example 2c

Synthesis of a Mixture of Alkyl Benzene Sulfonates of $C_{10}$-$C_{13}$ Chain Lengths Having a Random Distribution with an Average Number of Carbon Atoms of 12.2-12.3

The mixture of alkylbenzenes from Example 2b is sulfonated using the procedure described in Example 1c.

In some exemplary embodiments, the optionally renewable $C_{10}$-$C_{13}$ alkylphenyl sulfonates have a random alkyl chain distribution with an average total number of carbon atoms in their alkyl chains of 12.2-12.3. Further, these $C_{10}$-$C_{13}$ alkylphenyl sulfonates have less than 5 wt. % of $C_{14}$ alkylphenyl sulfonates, based on the total weight of the mixture. Traditional alkylphenyl sulfonates that have an average total number of carbon atoms of 12.2-12.3 include a much higher weight percentage of $C_{14}$ alkylphenyl sulfonates (e.g., greater than 10 wt. %). The higher the weight percentage of $C_{14}$ alkylphenyl sulfonates, the greater the toxicity of the mixture. Thus, the invention provides for the first time an environmentally improved mixture of optionally renewable $C_{10}$-$C_{13}$ alkylphenyl sulfonates having an average total number of carbon atoms in their alkyl chains of 12.2-12.3, without toxicity issues. Further, the invention provides methods for obtaining this mixture that are not cost prohibitive. A table showing the alkyl chain distributions in commercial alkylphenyl sulfonates having an average number of total carbon atoms of 12.2-12.3 and the mixture of alkylphenyl sulfonates of the invention having an average number of total carbon atoms of 12.2-12.3 is provided below.

Comparison of the Alkyl Chain Distribution in a Commercial Mixture with a Mixture of the Invention Having a Random Distribution.

| Chain Length | Commercial Mixture (mol. equiv.) | Inventive Mixture (mol. equiv.) |
| --- | --- | --- |
| 10 | 9.3 | 0 |
| 11 | 21.0 | 19 |
| 12 | 25.6 | 41 |
| 13 | 30.7 | 40 |
| 14 | 13.5 | 0 |

Example 2

Modified Alkylphenyl Sulfonate Prepared Via Skeletally Isomerized Linear Bio-Alkenes Step (a): Skeletal Isomerization The mixture of $C_{10}$ and $C_{12}$ alkenes from Example 1a is passed over a Pt-SAPO catalyst at 220° C. and any suitable liquid hourly space velocity (LHSV), for example 1.0. The catalyst is prepared as described in Example 1 of U.S. Pat. No. 5,082,956, Example 1 and the specification PCT Application Publication No. WO 1995/21225, each incorporated herein by reference. The product is a skeletally isomerized, lightly branched alkene having a bimodal distribution suitable for making the alkylphenyl sulfonate surfactants of the invention. The temperature in this step can be about 200° C. to about 400° C., preferably about 230° C. to about 320° C. The pressure is typically about 15 psig to about 2000 psig, preferably about 15 psig to about 1000 psig, more preferably about 15 psig to about 600 psig. Hydrogen is a useful pressurizing gas. The liquid hourly space velocity or weight hourly space velocity is about 0.5 to about 20. Low pressure and low hourly space velocity provide improved selectivity, more skeletal isomerization, and less cracking. Any volatile compounds are removed by distillation by boiling at up to about 40° C./10 mmHg Step (b): Alkylation To a glass autoclave liner is added a 1 mole equivalent of the lightly branched alkene mixture produced in step (a), 20 molar equivalents of benzene, and 20 wt. % of a shape selective zeolite catalyst (e.g., acidic mordenite catalyst ZEO- CAT™ FM-8/25H by Zeochem). The glass liner is sealed inside a stainless steel rocking autoclave. The autoclave is purged twice with 250 psig $N_2$, and then charged to 1000 psig $N_2$. With mixing, the mixture is heated to 170-190° C. for about 14-15 hours, at which time it is then cooled and removed from the autoclave. The reaction mixture is filtered to remove the catalyst and is concentrated by distilling off unreacted starting materials and/or impurities (e.g., benzene, alkene, paraffin, trace materials). Any useful material that is distilled off is recycled. A clear, near-colorless liquid product is obtained. The product formed is a desirable modified alkylbenzene mixture which can, as an option, be shipped to a remote manufacturing facility where the additional steps of sulfonation and incorporation into a cleaning composition can be accomplished.

Step (c): Sulfonation

The modified alkylbenzene mixture of step (b) is sulfonated with an equivalent of chlorosulfonic acid using methylene chloride as the solvent. The methylene chloride is then removed by distillation Step (d): Neutralization The product of step (c) is neutralized with sodium methoxide in methanol and the methanol is evaporated to produce a modified alkylphenyl sulfonate, sodium salt mixture.

Example 3

Modified Alkylphenyl Sulfonate Surfactant Prepared Via Skeletally Isomerized Linear Bio-Alkenes Step (a): Skeletal Isomerization A mixture of $C_{10}$ and $C_{12}$ alkenes from Example 1a is passed over a Pt-SAPO catalyst at 220° C. and any suitable liquid hourly space velocity (LHSV), for example 1.0. The catalyst is prepared as described in Example 1 of U.S. Pat. No. 5,082,956, Example 1 and the specification PCT Application Publication No. WO 1995/21225, each incorporated herein by reference. The product is a skeletally isomerized, lightly branched alkene having a bimodal distribution of chain lengths suitable for making alkylphenyl sulfonate surfactants. The temperature in this step can be about 200° C. to about 400° C., preferably about 230° C. to about 320° C. The pressure is typically about 15 psig to about 2000 psig, preferably about 15 psig to about 1000 psig, more preferably about 15 psig to about 600 psig. Hydrogen is a useful pressurizing gas. The liquid hourly space velocity or weight hourly space velocity is about 0.5 to about 20. Low pressure and low hourly space velocity provide improved selectivity, more skeletal isomerization, and less cracking. Any volatile compounds are removed by distillation by boiling at up to about 40° C./10 mmHg Step (b): Alkylation To a glass autoclave liner is added a 1 mole equivalent of the lightly branched alkene mixture produced in step (a), 20 molar equivalents of benzene, and 20 wt. % of a shape selective zeolite catalyst (e.g., acidic mordenite catalyst ZEO-CAT™ FM-8/25H by Zeochem). The glass liner is sealed inside a stainless steel rocking autoclave. The autoclave is purged twice with 250 psig $N_2$, and then charged to 1000 psig $N_2$. With mixing, the mixture is heated to 170-190° C. for about 14-15 hours, at which time it is then cooled and removed from the autoclave. The reaction mixture is filtered to remove the catalyst and is concentrated by distilling off unreacted starting materials and/or impurities (e.g., benzene, alkene, paraffin, trace materials). Any useful material that is distilled off is recycled. A clear, near-colorless liquid product is obtained. The product formed is a desirable modified alkylbenzene mixture which can, as an option, be shipped to a remote manufacturing facility where the additional steps of sulfonation and incorporation into a cleaning composition can be accomplished.

Step (c): Sulfonation

The modified alkylbenzene mixture of step (b) is sulfonated with an equivalent of sulfur trioxide/air (without methylene chloride) as the sulfonating agent, as described in U.S. Pat. No. 3,427,342, incorporated herein by reference.

Step (d): Neutralization

The product of step (c) is neutralized with sodium hydroxide in methanol and the methanol is evaporated to produce a modified alkylphenyl sulfonate, sodium salt mixture.

Example 4

Modified Alkylphenyl Sulfonate Prepared Via Skeletally Isomerized Linear Bio-Alkenes Step (a): Partially Reducing the Linearity of an Alkene A lightly branched alkene mixture is prepared by passing a mixture of $C_{11}$, $C_{12}$, and $C_{13}$ mono-alkenes in a weight ratio of 1:3:1 over H-ferrierite catalyst at 430° C., as described in U.S. Pat. No. 5,510,306, incorporated herein by reference. The resulting solution is distilled to remove any volatile compounds by boiling at up to about 40° C. at 10 mmHg Step (b): Alkylation To a glass autoclave liner is added a 1 mole equivalent of the lightly branched alkene mixture produced in step (a), 20 molar equivalents of benzene, and 20 wt. % of a shape selective zeolite catalyst (e.g., acidic mordenite catalyst ZEO-CAT™ FM-8/25H by Zeochem). The glass liner is sealed inside a stainless steel rocking autoclave. The autoclave is purged twice with 250 psig $N_2$, and then charged to 1000 psig $N_2$. With mixing, the mixture is heated to 170-190° C. for about 14-15 hours, at which time it is then cooled and removed from the autoclave. The reaction mixture is filtered to remove the catalyst and is concentrated by distilling off unreacted starting materials and/or impurities (e.g., benzene, alkene, paraffin, trace materials). Any useful material that is distilled off is recycled. A clear, near-colorless liquid product is obtained. The product formed is a desirable modified alkylbenzene mixture which can, as an option, be shipped to a remote manufacturing facility where the additional steps of sulfonation and incorporation into a cleaning composition can be accomplished.

Step (c): Sulfonation

The modified alkylbenzene mixture of step (b) is sulfonated with an equivalent of chlorosulfonic acid using methylene chloride as the solvent. The methylene chloride is then removed by distillation Step (d): Neutralization The product of step (c) is neutralized with sodium methoxide in methanol and the methanol is evaporated to produce a modified alkylphenyl sulfonate, sodium salt mixture.

Example 5

Consumer Product Cleaning Formulae Having a Renewable Linear Alkylphenyl Sulfonate (LAS) as Primary/Co-Surfactant The mixture of renewable $C_{10}$-$C_{13}$ alkylphenyl sulfonates is added to consumer product cleaning formulations, as shown in the below tables. The LAS can include, for example, a bimodal distribution of linear $C_{10}$-$C_{13}$ alkylphenyl sulfonate having an average chain length of 10.9.

The following detergent compositions A to K suitable for hand-washing soiled fabrics are prepared in accord with the invention:

Granular Laundry Detergents

| Formula | A wt % | B wt % | C wt % | D wt % | E wt % |
|---|---|---|---|---|---|
| C10-12 Linear Alkylbenzene Sulfonic Acid, sodium salt from Example 1c | 5-20 | 5-20 | 5-20 | 5-20 | 5-20 |
| C12-14 alcohol sulfate, sodium salt | 10-20 | 10-20 | 10-20 | 10-20 | 10-20 |
| $C_{12-18}$ Ethoxylate | — | — | 0-3 | — | 0-1 |
| $C_{14-15}$ alkyl ethoxylate (EO = 7) | 0-3 | 0-3 | — | 0-5 | 0-3 |
| Dimethyl hydroxyethyl lauryl ammonium chloride | — | — | 0-2 | 0-2 | 0-2 |
| Sodium tripolyphosphate | 20-40 | — | 18-33 | 12-22 | 0-15 |
| Zeolite | 0-10 | 20-40 | 0-3 | — | — |
| Silicate builder | 0-10 | 0-10 | 0-10 | 0-10 | 0-10 |
| Carbonate | 0-30 | 0-30 | 0-30 | 5-25 | 0-20 |
| Diethylene triamine penta acetate | 0-1 | 0-1 | 0-1 | 0-1 | 0-1 |
| Polyacrylate | 0-3 | 0-3 | 0-3 | 0-3 | 0-3 |
| Carboxy Methyl Cellulose | 0.2-0.8 | 0.2-0.8 | 0.2-0.8 | 0.2-0.8 | 0.2-0.8 |
| Percarbonate | 0-10 | 0-10 | 0-10 | 0-10 | 0-10 |
| Nonanoyloxybenzenesulfonate, sodium salt | — | — | 0-2 | 0-2 | 0-2 |
| Tetraacetylethylenediamine | — | — | 0-0.6 | 0-0.6 | 0-0.6 |
| Zinc Phthalocyanine Tetrasulfonate | — | — | 0-0.005 | 0-0.005 | 0-0.005 |
| Brightener | 0.05-0.2 | 0.05-0.2 | 0.05-0.2 | 0.05-0.2 | 0.05-0.2 |
| $MgSO_4$ | — | — | 0-0.5 | 0-0.5 | 0-0.5 |
| Enzymes | 0-0.5 | 0-0.5 | 0-0.5 | 0-0.5 | 0-0.5 |
| Minors (perfume, dyes, suds stabilizers) | balance | balance | balance | balance | balance |

Liquid Laundry Detergents

| Ingredient | F wt. % | G wt. % | H wt. % | I wt. % | J wt. % | K wt. % |
|---|---|---|---|---|---|---|
| C10-12 Linear Alkylbenzene Sulfonic Acid, sodium salt from Example 1c | 5.5 | 2.7 | 2.2 | 12.2 | 5.2 | 5.2 |
| $C12-14\ EO_3$ sulfate, sodium salt | 16.5 | 20 | 9.5 | 7.7 | 1.8 | 1.8 |
| Sodium C12-14 alkyl sulfate, sodium salt | 8.9 | 6.5 | 2.9 | — | | |
| C12-14 alkyl 7-ethoxylate | | | | | 0.15 | 0.15 |
| C14-15 alkyl 8-ethoxylate | | | | | 3.5 | 3.5 |
| C12-15 alkyl 9-ethoxylate | 1.7 | 0.8 | 0.3 | 18.1 | | |
| C12-18 Detergent acid | 2.2 | 2.0 | — | 1.3 | 2.6 | 2.6 |
| Citric acid | 3.5 | 3.8 | 2.2 | 2.4 | 2.5 | 2.5 |
| Protease enzyme | 1.7 | 1.4 | 0.4 | — | 0.5 | 0.5 |
| Amylase enzyme | 0.4 | 0.3 | — | — | 0.1 | 0.1 |
| Mannanase enzyme | | | | | 0.04 | 0.04 |
| PEG-PVAc Polymer[1] | — | — | — | — | — | 0.3 |
| Ethoxyed Hexamethylene Diamine Dimethyl Quat Disulfate | — | — | — | — | — | 0.7 |
| Diethylenetriamine-penta(methylene-phosphonic) acid | | | | | 0.2 | 0.2 |
| Solvents (1,2 propanediol, ethanol, stabilizers | 7 | 7.2 | 3.6 | 3.7 | 1.9 | 1.9 |
| Hydrogenated castor oil derivative structurant | 0.3 | 0.2 | 0.2 | 0.2 | 0.35 | 0.35 |
| Polyacrylate | — | — | — | 0.1 | — | — |
| Polyacrylate copolymer[2] | — | — | — | 0.5 | — | — |
| Sodium carbonate | — | — | — | 0.3 | — | — |
| Sodium silicate | — | — | — | — | — | — |
| Borax | 3 | 3 | 2 | 1.3 | — | — |
| Boric acid | 1.5 | 2 | 2 | 1.5 | 1.5 | 1.5 |
| Perfume | 0.5 | 0.5 | 0.5 | 0.8 | 0.5 | 0.5 |
| Buffers (sodium hydroxide, monoethanolamine) | | | | | 3.3 | 3.3 |
| Water, dyes and miscellaneous | Balance | | | | | |

[1]PEG-PVA graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[2]Alco 725 (styrene/acrylate)

Example 6

Hand Dishwashing Formulae Having a Renewable Linear Alkylphenyl Sulfonate (LAS) as Primary/Co-Surfactant The mixture of renewable $C_{10}$-$C_{13}$ alkylphenyl sulfonates is added to hand dishwashing formulations, as shown in the below table. The LAS can include, for example, a bimodal distribution of linear $C_{10}$-$C_{13}$ alkylbenzyl sulfonate having an average chain length of 11.3.

| | Formulation | | | |
|---|---|---|---|---|
| Component | A | B | C | D |
| LAS from Example 1c | 5 | 10 | 15 | 25 |
| AE(1)S | 15 | 10 | 5 | 5 |
| AS | 10 | 5 | 2 | 0 |
| MES | 0 | 5 | 0 | 0 |
| CMEA | 0.5 | 0 | 0 | 0 |
| CAPB | 1 | 1 | 0 | 1 |
| C11E9 | 0.5 | 2 | 1 | 0 |
| APG | 0 | 0 | 0 | 1.5 |
| Coco Amine oxide | 1 | 0.25 | 2.0 | 1.5 |

-continued

| | Formulation | | | |
|---|---|---|---|---|
| Component | A | B | C | D |
| Diamine | 0 | 0.6 | 0.6 | 0.4 |
| Magnesium salt | 0.3 | 0.1 | 0 | 0 |
| Perfume | 0.5 | 1.0 | 1.5 | 1.5 |
| Finishing Agents | qs | qs | qs | qs |

LAS—Sodium Linear alkylphenyl sulfonate;
AS—Sodium or potassium or monoethanolamine $C_{12}$ or $C_{12-13}$ or $C_{12-14}$ alkyl sulfate;
AE(1)S—Sodium or potassium or monoethanolamine neutralized $C_{12}$ or $C_{12-13}$ or $C_{12-14}$ alkyl ethoxy(1) Sulfate;
MES—$C_{12-14}$ methyl ester sulfonate;
CAPB—Cocoamidopropyl Betaine;
CMEA—Cocomonoethanolamide;
C11E9—C11 ethoxylate (9);
APG—C12-14 alkyl polyglucoside;
Coco Amine Oxide—$C_{12-14}$ alkyl dimethyl amine oxide;
Diamine—1,3 cyclohexanediamine, 1,3 propane diamine, any C3 to C7 alkyl diamine;
Magnesium salt—magnesium chloride, magnesium hydroxide or magnesium sulfate;
Finishing Agents: preservatives, solvents, salts, dyes, buffers, processing aids, excipients, etc.

Example 7

Shampoo Formulae Having a Renewable Linear Alkylphenyl Sulfonate (LAS) as Primary/Co-Surfactant The mixture of renewable $C_{10}$-$C_{13}$ alkylphenyl sulfonates is added to shampoo formulations, as shown in the below table. The LAS can include, for example, a bimodal distribution of linear $C_{10}$-$C_{13}$ alkylphenyl sulfonate having an average chain length of 10.9.

| | | Formulation | | |
|---|---|---|---|---|
| Component | Typical | A | B | C |
| Surfactants | | | | |
| SLS | 1.5 | 1.5 | 1.5 | 1.5 |
| SLE(1)S | 10 | | 10 | 12 |
| LAS from Example 1c | | 10 | 2 | 2 |
| CMEA | 0.5 | | | |
| CAPB | 2 | 2 | | 1 |
| Benefit Agents | | | | |
| Guar Cationic Polymer | 0.25 | 0.25 | 0.25 | 0.25 |
| LP Silicone | 1.0 | 1.0 | 1.0 | 1.0 |
| ZPT | | | | 1.0 |
| Aesthetics | | | | |
| EGDS | 1.5 | 1.5 | 1.5 | 1.5 |
| Perfume | 1.5 | 1.5 | 1.5 | 1.5 |
| Finishing Agents | qs | qs | qs | qs |

SLS—Sodium Lauryl Sulfate;
SLE(1)S—Sodium Laureth(1) Sulfate;
CAPB—Cocoamidopropyl Betaine;
CMEA—Cocomonoethanolamide;
EGDS—Etheylene Glycol Distearate;
Guar—Hydroxypropyltrimoinum guar (cationic);
LP-Silicone—Large Particle (>20 um) silicone;
PQ-10 Polyquat-10;
ZPT—Zinc pyridinethione;
Finishing Agents: preservatives, salts, buffers, processing aids, excipients, etc.

Example 8

Comparison of $C_{10}$-$C_{13}$ Linear Alkylbenzenes Having a Bimodal Alkyl Chain Distributions Four samples of $C_{10}$-$C_{13}$ linear alkylbenzene (LAB) that have the following alkyl group distributions are prepared by standard synthetic measures published in literature, such as, Alul et al., J. Org. Chem. 32(11):3365-3369 (1967). A bimodal distribution with an average chain length of 10.9 is prepared by blending the peaked $C_{10}$ LAB with the peaked $C_{12}$ LAB, and sulfonating according to procedures described herein. The mixtures of LAB having a skewed distribution are prepared by the alkylation of homogeneous, purified alkenes using standard alkylation procedures, as previously described herein. These non-bioderived LAB samples are compared to standard commercial mixtures that contain $C_{10}$, $C_{11}$, $C_{12}$ and $C_{13}$ chain lengths based on kerosene derived paraffins and olefins.

Alkyl Chain Length Distribution of Linear Alkylbenzene (LAB) and Petresa Supplied LAB Stocks

| Alkyl Chain Length | Commercial LAB (%) | Peaked $C_{10}$ LAB (%) | Peaked $C_{11}$ LAB (%) | Peaked $C_{12}$ LAB (%) | Peaked $C_{13}$ LAB (%) |
|---|---|---|---|---|---|
| 8 | 2.90 | 7.20 | 0.00 | 0.00 | 0.00 |
| 10 | 8.20 | 84.60 | 5.90 | 0.00 | 0.00 |
| 11 | 28.70 | 8.20 | 84.60 | 9.90 | 0.00 |
| 12 | 39.20 | 0.00 | 9.50 | 87.10 | 5.60 |
| 13 | 16.00 | 0.00 | 0.00 | 3.00 | 93.10 |
| 14 | 5.00 | 0.00 | 0.00 | 0.00 | 1.30 |
| Average | 11.69 | 9.94 | 11.04 | 11.93 | 12.96 |

These LABs were sulfonated using 15% oleum and subsequently neutralized using 10 wt. % of sodium hydroxide. The resulting sodium linear alkylphenyl sulfonates (LAS) were added to a mixture of the standard, commercial grate linear alkylphenyl sulfonates having an average chain length of 11.7 (see the above table for the composition) to prepare surfactants of various chain lengths and chain distributions ranging from 12.2 to 10.9. The alkyl chain length distributions for these surfactants are summarized in the below table.

Proportions of Purified Sodium Linear Alkylphenyl Sulfonate (NaLAS) Required to Achieve a Desired Average Chain Length

| Average Chain Length | 11.7 Reference (LAS, standard commercial distribution) | 12.2 (skewed distribution) | 10.9 (bimodal distribution) |
|---|---|---|---|
| Current NaLAS (11.7) | 100.00% | 0.60% | 57.14% |
| $C_{10}$ NaLAS | 0.00% | 0.00% | 42.86% |
| $C_{11}$ NaLAS | 0.00% | 0.00% | 0.00% |
| $C_{12}$ NaLAS | 0.00% | 69.64% | 0.00% |
| $C_{13}$ NaLAS | 0.00% | 29.76% | 0.00% |

These NaLAS surfactants were incorporated into detergent compositions, as shown in the below table.

| Formulation/Component | Concentration (wt. %), 1250 ppm, 4 gpg Consumer Soils |
|---|---|
| NaLAS from the above table | 18.00 |
| N-C12/14-N-(bis-hydroxyethyl)-ammonium chloride | 0.60 |
| $C_{12-14}$ $EO_3$ sulfate, sodium salt | 1.00 |
| Savinase enzyme | 0.70 |
| Protease enzyme | 0.36 |
| Sodiumtripolyphospate | 22.50 |
| $Na_2CO_3$ | 13.00 |
| $Na_2SO_4$ | 23.94 |
| Diethylenetriaminipentaacetic acid | 0.50 |
| acrylic/maleic copolymer | 0.90 |

-continued

| Formulation/Component | Concentration (wt. %), 1250 ppm, 4 gpg Consumer Soils |
|---|---|
| Caboxymethylcellulose | 0.44 |
| Sodium Silicate | 9.06 |
| Water | 9.00 |

Performance data was collected using above detergent compositions on consumer soils and is summarized in the below table.

Cleaning Performance Results Using Consumer Relevant Soils at 1250 ppm of the Powder Detergent, 4 gpg, 25° C. (Surfactant was Incorporated as a LAS Replacement in a Standard Granular Detergent Matrix)

| Soil Type | 11.7 Standard Reference (LAS) | 12.2 (skewed distribution) | 10.9 (bimodal distribution) |
|---|---|---|---|
| Collar soil | 0 | 0.31 | 0.24 |
| Dingy/T-shirt | 0 | 1.09 s | 0.80 s |
| Sock soil | 0 | 0.65 | 0.19 |
| Philippine MCFS | 0 | 1.11 s | 0.06 |
| EMC SCFS | 0 | 0.17 | −0.39 |

Standard consumer fabrics, such as polyester dress shirts, cotton T-shirts, cotton socks, and cotton swatches were soiled with various soil types. All realistic soiled fabrics were worn for 1-2 weeks to provide said soiled fabrics. Dress shirt collars were soiled by exposure to body perspiration. T-shirts and socks were worn while playing athletic sports, such as basketball. Philippine MCFS and EMC SCFS are artificial soils generated in the laboratory and applied to clean fabric swatches. All fabrics were split int to equal soiled pieces and washed in each type of LAS containing detergent system and then dried. Each of the three pieces were compared to their split garment piece and the quality of soil removal was judged by a set of panelists that used a grading scale of 0-4. The data was then compiled. The letter 's' stands for significant difference versus the control.

The detergent compositions comprising the 10.9 LAS provides enhanced performance over the detergent composition comprising the 11.7 LAS, a direct result of increased stability of mixed micelles. The 10.9 LAS is a bimodal distribution, containing a greater quantity of $C_8$-$C_{11}$ LAS than the corresponding LAS with an average chain length of 12.2. Because the solubility of surfactant decreases as chain length increases, there is more frequent participation of $C_8$-$C_{11}$ LAS in mixed micelles when 10.9 LAS is used than when 12.2 LAS is used, providing increased detergency.

Example 9

Comparison of $C_{10}$-$C_{13}$ Linear Bio-Alkylbenzene Sulfonates Having a Peaked Alkyl Chain Distributions The peaked linear bio-alkylbenzenes are prepared according to the procedure used in Example 1 with a mixture of 2-butene, 3-hexene and 1-pentene in the ratio of 1:1:0.2 to provide a peaked distribution (e.g., FIG. 2A), with ratios of C10:C11:C12:C13 of about 0.1:1:1:0.1.

Example 10

Comparison of $C_{10}$-$C_{13}$ Linear Bio-Alkylbenzene Sulfonates Having a Skewed Alkyl Chain Distributions The skewed linear bio-alkylbenzenes are prepared according to the procedure used in Example 1 with a mixture of 3-heptene and propene in the ratio of 9:1 to provide a skewed distribution (e.g., FIG. 3B), with ratios of C10:C11:C12:C13 of about 1:1:9:9.

Example 11

Comparison of $C_{10}$-$C_{13}$ Linear Bio-Alkylbenzene Sulfonates Having a Random Alkyl Chain Distributions A relatively random distribution of linear bio-alkylbenzenes are prepared according to the procedure used in Example 1 with a mixture of 1-butene, propene, and 1-pentene in the ratio of 4:1:1 to provide said random distribution (e.g., FIG. 4).

Example 12

Comparison of $C_{10}$-$C_{13}$ Linear Bio-Alkylbenzene Sulfonates Having a Flat Alkyl Chain Distributions A relatively flat distribution of linear bio-alkylbenzenes are prepared according to the procedure used in Example 1 with a mixture of 1-butene, 2-butene, 1-pentene, 2-pentene in the ratio of 1:1:1:1 to provide said flat distribution (e.g., FIG. 5), with ratios of C10:C11:C12:C13 of about 1:1:1:1.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A composition consisting of:
(a) about 0.001 wt. % to about 99.999 wt. % of a mixture of $C_{10}$-$C_{13}$ alkylphenyl sulfonates, based on the total weight of the composition, wherein the alkyl groups independently have a total of 10-13 carbon atoms, 0-3 $C_1$-$C_2$ alkyl branches; and, wherein the alkyl chain dis- tribution is a bimodal distribution, wherein the mixture comprises $C_{10}$-$C_{13}$ alkylphenyl sulfonates having:
(a) $C_{10}$ and $C_{13}$ alkyl groups to $C_{11}$ and $C_{12}$ alkyl groups; or
(b) $C_{10}$, $C_{11}$, and $C_{13}$ alkyl groups to $C_{12}$ alkyl groups; or
(c) $C_{10}$, $C_{12}$, and $C_{13}$ alkyl groups to $C_{11}$ alkyl groups
in a weight ratio of at least about 60 to about 40; and
wherein the mixture comprises:
(i) less than about 5 wt. % of alkylphenyl sulfonates with alkyl groups having 9 or fewer carbon atoms and alkyl groups having 14 or more carbon atoms, based on the total weight of the mixture;
(ii) less than about 10 wt. % of $C_{10}$-$C_{13}$ alkylphenyl sulfonates having two or more $C_{10}$-$C_{13}$ alkyl groups on the phenyl group, based on the total weight of the mixture; and,
(iii) less than about 10 wt % of $C_{10}$-$C_{13}$ alkylphenyl sulfonates having an alkyl group comprising a quaternary carbon atom, based on the total weight of the mixture; and,
(b) 0.001 wt. % to about 99.999 wt. % of
at least one additional cleaning component comprising an enzyme; and wherein the composition optionally comprises and additional anionic surfactant, and organic polymeric compound and a chelating agent.

2. The composition of claim 1, wherein the mixture of alkylphenyl sulfonates comprises at least about 40 wt. % of $C_{10}$-$C_{13}$ alkylphenyl sulfonates each having a linear alkyl group, based on the total weight of the mixture.

3. The composition of claim 1, wherein the mixture of alkylphenyl sulfonates comprises at least about 40 wt. % of $C_{10}$-$C_{13}$ alkylphenyl sulfonates each having a branched alkyl group, based on the total weight of the mixture.

4. The composition of claim 1, wherein the biobased content of the alkyl groups of the alkylphenyl sulfonates is at least about 5%.

5. The composition of claim 1, wherein the phenyl groups of the alkylphenyl sulfonates have a biobased content of at least about 50%.

6. The composition of claim 1, wherein the composition is selected from the group consisting of a granular detergent, a bar-form detergent, a liquid laundry detergent, a liquid hand dishwashing composition, a hard surface cleaner, a tablet, a disinfectant, an industrial cleaner, a highly compact liquid, a powder, and a decontaminant.

7. The composition of claim 1, wherein the enzyme comprises a protease.

* * * * *